(12) United States Patent
Ross

(10) Patent No.: US 11,179,555 B2
(45) Date of Patent: *Nov. 23, 2021

(54) NANOPATTERNED MEDICAL DEVICE WITH ENHANCED CELLULAR INTERACTION

(71) Applicant: SORRENTO THERAPEUTICS, INC., San Diego, CA (US)

(72) Inventor: Russell Frederick Ross, Jacksonville Beach, FL (US)

(73) Assignee: SORRENTO THERAPEUTICS, INC., San Diego, CA (US)

( * ) Notice: Subject to any disclaimer, the term of this patent is extended or adjusted under 35 U.S.C. 154(b) by 315 days.

This patent is subject to a terminal disclaimer.

(21) Appl. No.: 16/361,484

(22) Filed: Mar. 22, 2019

(65) Prior Publication Data

US 2019/0269897 A1 Sep. 5, 2019

Related U.S. Application Data

(63) Continuation of application No. 13/095,489, filed on Apr. 27, 2011, now Pat. No. 10,245,421.
(Continued)

(51) Int. Cl.
*A61M 37/00* (2006.01)
*A61B 17/20* (2006.01)
(Continued)

(52) U.S. Cl.
CPC ....... *A61M 37/0015* (2013.01); *A61B 17/205* (2013.01); *A61K 9/0021* (2013.01);
(Continued)

(58) Field of Classification Search
CPC .. A61M 2037/0061; A61M 2037/0053; A61M 2037/0046; A61M 2037/0038;
(Continued)

(56) References Cited

U.S. PATENT DOCUMENTS 3,797,494 A 3/1974 Zaffaroni
3,964,482 A 6/1976 Gerstel
(Continued)

FOREIGN PATENT DOCUMENTS

EP 2100850 A1 9/2009
WO 1999045860 A1 9/1999
(Continued)

OTHER PUBLICATIONS

First Examination Report for IN Application No. 9142/CHENP/2012, dated Aug. 16, 2019, 5 pages.
(Continued)

*Primary Examiner* — Nathan R Price
*Assistant Examiner* — Anh Bui
(74) *Attorney, Agent, or Firm* — Armstrong Teasdale LLP

(57) ABSTRACT

A medical device for delivering a drug compound through a stratum corneum includes a support having an aperture, an array of microneedles extending outwardly from the support, a plurality of nanostructures associated with each microneedle, and a reservoir wherein the drug compound is retained. At least one microneedle contains a shaft extending from the support. The shaft includes a tip configured to penetrate the stratum corneum. The shaft defines a channel extending from the support to the tip. The channel is in at least partial alignment with the aperture. At least some of the microneedles of the array of microneedles each have a cross-sectional dimension of from about 1 micrometer to about 1 millimeter. At least some of the nanostructures have a cross-sectional dimension less than about 500 nanometers and greater than about 5 nanometers and an aspect ratio of from about 0.2 to about 5.

20 Claims, 28 Drawing Sheets

Related U.S. Application Data

(60) Provisional application No. 61/328,723, filed on Apr. 28, 2010, provisional application No. 61/411,071, filed on Nov. 8, 2010, provisional application No. 61/435,939, filed on Jan. 25, 2011.

(51) Int. Cl.
  *A61K 9/00* (2006.01)
  *A61K 38/19* (2006.01)
  *A61K 9/70* (2006.01)
  *A61K 38/17* (2006.01)
  *B29C 59/00* (2006.01)
  *B29C 59/02* (2006.01)
  *B29L 31/00* (2006.01)

(52) U.S. Cl.
  CPC ........ *A61K 9/7023* (2013.01); *A61K 38/1793* (2013.01); *A61K 38/191* (2013.01); *B29C 59/002* (2013.01); *B29C 59/026* (2013.01); *A61M 2037/003* (2013.01); *A61M 2037/0023* (2013.01); *A61M 2037/0038* (2013.01); *A61M 2037/0053* (2013.01); *A61M 2037/0061* (2013.01); *B29C 2059/023* (2013.01); *B29K 2995/0056* (2013.01); *B29L 2031/756* (2013.01); *B29L 2031/7544* (2013.01); *Y10T 156/10* (2015.01); *Y10T 156/1039* (2015.01); *Y10T 156/1057* (2015.01)

(58) Field of Classification Search
  CPC .... A61M 2037/003; A61M 2037/0023; A61M 37/0015
  See application file for complete search history.

(56) References Cited

U.S. PATENT DOCUMENTS

| | | |
|---|---|---|
| 4,031,894 A | 6/1977 | Urquhart |
| 4,051,840 A | 10/1977 | Kantrowitz |
| 4,201,211 A | 5/1980 | Chandrasekaran |
| 4,379,454 A | 4/1983 | Campbell |
| 4,436,741 A | 3/1984 | Urquhart |
| 4,588,580 A | 5/1986 | Gale |
| 4,615,699 A | 10/1986 | Gale |
| 4,661,105 A | 4/1987 | Gale |
| 4,681,584 A | 7/1987 | Gale |
| 4,698,062 A | 10/1987 | Gale |
| 4,725,272 A | 2/1988 | Gale |
| 4,832,953 A | 5/1989 | Campbell |
| 4,880,633 A | 11/1989 | Loper |
| 4,908,027 A | 3/1990 | Enscore |
| 5,004,610 A | 4/1991 | Osborne |
| 5,310,559 A | 5/1994 | Shah |
| 5,328,470 A | 7/1994 | Nabel |
| 5,342,623 A | 8/1994 | Enscore |
| 5,344,656 A | 9/1994 | Enscore |
| 5,364,630 A | 11/1994 | Osborne |
| 6,132,755 A | 10/2000 | Eicher |
| 6,334,856 B1 | 1/2002 | Allen |
| 6,375,978 B1 | 4/2002 | Kleiner |
| 6,471,993 B1 | 10/2002 | Shastri |
| 6,569,143 B2 | 5/2003 | Alchas |
| 6,656,147 B1 | 12/2003 | Gertsek |
| 6,663,820 B2 | 12/2003 | Arias |
| 6,767,341 B2 | 7/2004 | Cho |
| 6,881,203 B2 | 4/2005 | Delmore |
| 6,926,953 B2 | 8/2005 | Nealey |
| 6,979,347 B1 | 12/2005 | Wu |
| 6,995,336 B2 | 2/2006 | Hunt |
| 7,048,723 B1 | 5/2006 | Frazier |
| 7,108,681 B2 | 9/2006 | Gartstein |
| 7,115,108 B2 | 10/2006 | Wilkinson |
| 7,129,554 B2 | 10/2006 | Lieber |
| 7,131,987 B2 | 11/2006 | Sherman |
| 7,185,663 B2 | 3/2007 | Koch |
| 7,189,435 B2 | 3/2007 | Tuominen |
| 7,226,439 B2 | 6/2007 | Prausnitz |
| 7,250,037 B2 | 7/2007 | Shermer |
| 7,285,113 B2 | 10/2007 | Yeshurun |
| 7,315,758 B2 | 1/2008 | Kwiatkowski |
| 7,332,339 B2 | 2/2008 | Canham |
| 7,374,864 B2 | 5/2008 | Guo |
| 7,416,541 B2 | 8/2008 | Yuzhakov |
| 7,429,258 B2 | 9/2008 | Angel |
| 7,449,200 B2 | 11/2008 | Sung |
| 7,537,590 B2 | 5/2009 | Santini, Jr. |
| 7,544,770 B2 | 6/2009 | Haynie |
| 7,556,615 B2 | 7/2009 | Pettis |
| 7,563,451 B2 | 7/2009 | Lin |
| 7,572,405 B2 | 8/2009 | Sherman |
| 7,578,954 B2 | 8/2009 | Gartstein |
| 7,582,069 B2 | 9/2009 | Laurent |
| 7,588,552 B2 | 9/2009 | Yeshurun |
| 7,611,481 B2 | 11/2009 | Cleary |
| 7,627,938 B2 | 12/2009 | Kim |
| 7,658,728 B2 | 2/2010 | Yuzhakov |
| 7,753,888 B2 | 7/2010 | Mukerjee |
| 7,785,301 B2 | 8/2010 | Yuzhakov |
| 7,803,574 B2 | 9/2010 | Desai |
| 7,828,827 B2 | 11/2010 | Gartstein |
| 7,846,488 B2 | 12/2010 | Johnson |
| 7,901,387 B2 | 3/2011 | Stemme |
| 7,914,480 B2 | 3/2011 | Cleary |
| 7,914,813 B2 | 3/2011 | Adachi |
| 7,972,616 B2 | 7/2011 | Dubrow |
| 7,981,346 B2 | 7/2011 | Griss |
| 7,997,274 B2 | 8/2011 | Baska |
| 8,052,633 B2 | 11/2011 | Kendall |
| 8,057,842 B2 | 11/2011 | Choi |
| 8,137,697 B1 | 3/2012 | Sung |
| 8,137,736 B2 | 3/2012 | Zhu |
| 8,238,995 B2 | 8/2012 | Chandrasekaran |
| 8,366,677 B2 | 2/2013 | Kaspar |
| 8,389,205 B2 | 3/2013 | Duerig |
| 8,419,708 B2 | 4/2013 | Tokumoto |
| 8,506,530 B2 | 8/2013 | Laermer |
| 8,574,615 B2 | 11/2013 | Tenney |
| 8,690,838 B2 | 4/2014 | Ozawa |
| 8,696,637 B2 | 4/2014 | Ross |
| 8,915,957 B2 | 12/2014 | Arney |
| 8,944,804 B2 | 2/2015 | Robeson |
| 9,522,262 B2 | 12/2016 | Ross |
| 9,522,263 B2 | 12/2016 | Ross |
| 9,526,883 B2 | 12/2016 | Ross |
| 9,545,507 B2 | 1/2017 | Ross |
| 9,550,053 B2 | 1/2017 | Ross |
| 10,029,082 B2 | 7/2018 | Ross |
| 10,245,421 B2 * | 4/2019 | Ross ...................... A61P 37/06 |
| 2002/0082543 A1 | 6/2002 | Park |
| 2002/0133129 A1 | 9/2002 | Arias |
| 2002/0138049 A1 | 9/2002 | Allen et al. |
| 2002/0183688 A1 | 12/2002 | Lastovich |
| 2004/0028875 A1 | 2/2004 | Van Rijn |
| 2004/0063100 A1 | 4/2004 | Wang |
| 2004/0087992 A1 | 5/2004 | Gartstein |
| 2004/0106904 A1 | 6/2004 | Gonnelli |
| 2004/0176732 A1 * | 9/2004 | Frazier .............. A61M 37/0015 604/345 |
| 2005/0049625 A1 | 3/2005 | Shaya |
| 2005/0112135 A1 | 5/2005 | Cormier |
| 2005/0118388 A1 | 6/2005 | Kingsford |
| 2005/0119723 A1 | 6/2005 | Peacock |
| 2005/0124967 A1 | 6/2005 | Kaestner |
| 2005/0137531 A1 | 6/2005 | Prausnitz |
| 2005/0143713 A1 | 6/2005 | Delmore |
| 2005/0178760 A1 | 8/2005 | Chang |
| 2006/0024358 A1 | 2/2006 | Santini |
| 2006/0025848 A1 | 2/2006 | Weber |
| 2006/0051404 A1 | 3/2006 | Yeshurun |
| 2006/0264893 A1 | 11/2006 | Sage, Jr. |
| 2007/0066934 A1 | 3/2007 | Etheredge |
| 2007/0078376 A1 | 4/2007 | Smith |
| 2007/0081977 A1 | 4/2007 | Horstmann |

(56) References Cited

U.S. PATENT DOCUMENTS

| | | |
|---|---|---|
| 2007/0088248 A1 | 4/2007 | Glenn |
| 2007/0110810 A1 | 5/2007 | Smith |
| 2007/0112309 A1 | 5/2007 | Zucker |
| 2007/0112548 A1 | 5/2007 | Dickerson |
| 2007/0191761 A1 | 8/2007 | Boone |
| 2007/0249552 A1 | 10/2007 | Khalili |
| 2007/0250018 A1 | 10/2007 | Adachi |
| 2007/0260201 A1 | 11/2007 | Prausnitz |
| 2007/0276318 A1 | 11/2007 | Henley |
| 2008/0026464 A1 | 1/2008 | Borenstein |
| 2008/0088066 A1 | 4/2008 | Ferguson |
| 2008/0091226 A1 | 4/2008 | Yeshurun |
| 2008/0097352 A1 | 4/2008 | Beck |
| 2008/0102192 A1 | 5/2008 | Johnson |
| 2008/0108958 A1 | 5/2008 | Carter |
| 2008/0139911 A1 | 6/2008 | Chandrasekaran |
| 2008/0195035 A1 | 8/2008 | Frederickson |
| 2008/0200883 A1 | 8/2008 | Tomono |
| 2008/0208076 A1 | 8/2008 | Cho |
| 2008/0214916 A1* | 9/2008 | Yodfat ............... A61M 5/1723 600/347 |
| 2008/0217180 A1* | 9/2008 | Doye .................. C25D 5/18 205/50 |
| 2008/0221408 A1 | 9/2008 | Hoarau |
| 2008/0262416 A1 | 10/2008 | Duan |
| 2008/0269666 A1 | 10/2008 | Wang |
| 2008/0269685 A1 | 10/2008 | Singh |
| 2008/0305989 A1 | 12/2008 | Wen |
| 2008/0311172 A1 | 12/2008 | Schapira |
| 2008/0312610 A1* | 12/2008 | Binks .................. A61P 29/00 604/272 |
| 2009/0012494 A1 | 1/2009 | Yeshurun |
| 2009/0043279 A1 | 2/2009 | Kaspar |
| 2009/0069788 A1 | 3/2009 | Yeshurun |
| 2009/0093776 A1 | 4/2009 | Yue |
| 2009/0093879 A1 | 4/2009 | Wawro |
| 2009/0099502 A1 | 4/2009 | Tokumoto |
| 2009/0118662 A1 | 5/2009 | Schnall |
| 2009/0118672 A1 | 5/2009 | Gonnelli |
| 2009/0137926 A1 | 5/2009 | Srinivasan |
| 2009/0177273 A1 | 7/2009 | Piveteau |
| 2009/0182306 A1 | 7/2009 | Lee et al. |
| 2009/0198189 A1 | 8/2009 | Simons |
| 2009/0232870 A1 | 9/2009 | Srivastava |
| 2009/0234301 A1* | 9/2009 | Tomono .............. B29C 43/021 604/272 |
| 2010/0004733 A1 | 1/2010 | Atanasoska |
| 2010/0021464 A1 | 1/2010 | Archambeau |
| 2010/0028604 A1* | 2/2010 | Bhushan .............. B08B 17/065 428/156 |
| 2010/0076035 A1 | 3/2010 | Carter |
| 2010/0119557 A1 | 5/2010 | Boyden |
| 2010/0121307 A1 | 5/2010 | Lockard |
| 2010/0130958 A1 | 5/2010 | Kang |
| 2010/0168506 A1 | 7/2010 | Moon |
| 2010/0215580 A1 | 8/2010 | Hanes |
| 2010/0256568 A1 | 10/2010 | Frederickson |
| 2010/0274203 A1 | 10/2010 | Lee |
| 2010/0316960 A1 | 12/2010 | Duerig et al. |
| 2011/0021996 A1 | 1/2011 | Lee |
| 2011/0046557 A1 | 2/2011 | Lee |
| 2011/0144591 A1 | 6/2011 | Ross |
| 2011/0160069 A1 | 6/2011 | Corrie |
| 2011/0270221 A1 | 11/2011 | Ross |
| 2011/0276003 A1 | 11/2011 | Luttge |
| 2012/0089117 A1* | 4/2012 | Junginger ......... A61M 37/0015 604/506 |
| 2012/0109065 A1 | 5/2012 | Backes |
| 2012/0128932 A1 | 5/2012 | Veith |
| 2013/0211310 A1 | 8/2013 | Bommarito |
| 2013/0331792 A1 | 12/2013 | Karp |
| 2014/0112921 A1 | 4/2014 | Ross |
| 2014/0287019 A1 | 9/2014 | Ollerenshaw |
| 2014/0343532 A1 | 11/2014 | Ross |
| 2015/0329362 A1 | 11/2015 | Aria |
| 2017/0143949 A1 | 5/2017 | Ross |
| 2017/0157380 A1 | 6/2017 | Ross |
| 2017/0157381 A1 | 6/2017 | Ross |

FOREIGN PATENT DOCUMENTS

| | | |
|---|---|---|
| WO | 2000074764 A1 | 12/2000 |
| WO | 2001075164 A2 | 10/2001 |
| WO | 2002030506 A2 | 4/2002 |
| WO | 2002032480 A2 | 4/2002 |
| WO | 2002091922 A1 | 11/2002 |
| WO | 2003020359 A2 | 3/2003 |
| WO | 2003024508 A2 | 3/2003 |
| WO | 2003059431 A1 | 7/2003 |
| WO | 2003092785 A1 | 11/2003 |
| WO | 2005049128 A1 | 6/2005 |
| WO | 2006062974 A2 | 6/2006 |
| WO | 2006075689 A1 | 7/2006 |
| WO | 2007012114 A1 | 2/2007 |
| WO | 2007112309 A2 | 10/2007 |
| WO | 2008003564 A1 | 1/2008 |
| WO | 2008024141 A2 | 2/2008 |
| WO | 2008115883 A1 | 9/2008 |
| WO | 2009049243 A2 | 4/2009 |
| WO | 2009079589 A2 | 6/2009 |
| WO | 2009079712 A1 | 7/2009 |
| WO | 2009113856 A1 | 9/2009 |
| WO | 2010070628 A1 | 6/2010 |
| WO | 2010087971 A2 | 8/2010 |
| WO | 2010126640 A2 | 11/2010 |
| WO | 2011070457 A2 | 6/2011 |
| WO | 2011116388 A1 | 9/2011 |
| WO | 2011135530 A2 | 11/2011 |
| WO | 2011135531 A2 | 11/2011 |
| WO | 2011135532 A2 | 11/2011 |
| WO | 2012006677 A1 | 1/2012 |
| WO | 2012020332 A2 | 2/2012 |
| WO | 2012046149 A1 | 4/2012 |

OTHER PUBLICATIONS

First Examination Report for IN Application No. 9171/CHENP/2012, dated Sep. 30, 2019, 5 pages.

Madara, JL, "Regulation of the movement of solutes across tight junctions", Annu Rev Physiol, 1998, 60:143-59.

Martinez-Palomo et al., "Experitmental Modulation of Occluding Junctions in a Cultured Transporting Epithelium", J. Cell Biology, 1980, 87: 736-745.

Ojakian, GK, "Tumor promotor-induced changes in the permeability of epithelial cell tight junctions", Cell, 1981, 23(1): 95-103.

Rubin, LL, "Endothelial cells: adhesion and tight junctions", Curr Opin Cell Biol, 1992, 4(5):830-3.

Verma et al., "Development of Transdermal Drug Dosage Fomulation for the Anti-Rheumatic Ayurvedic Medicianal Plants", Ancient Sci. Life, 2007; 11:66-9.

Ainslie, Kristy M., and Tejal A. Desai "Microfabricated implants for applications in therapeutic delivery, tissue engineering, and biosensing." Royal Society of Chemistry. 8. (2008): 1864-1878.

Ainslie, Kristy M., Rachel D. Lowe, Tristan T. Beaudette, Lamar Petty, Eric M. Bachelder, and Tejal A. Desai. "Microfabricated Devices for Enhanced Bioadhesive Drug Delivery: Attachment to and Small-Molecule Release Through a Cell Monolayer Under Flow." Small. (2009).

Bekarde, lil Gercek. "Biomimetic Apatite-coated PCL Scaffolds: Effect of Surface Nanotopography on Cellular Functions." Journal of Bioactive and Compatible Polymers. 24.6 (2009): 507-524.

Berry, C.C., M.J. Dalby, R.O.C. Oreffo, D. McCloy, and S. Affrosman. "The interaction of human bone marrow cells with nanotopographical features in three dimensional constructs." Journal of Biomedical Materials Research Part A. 79A.2 (2006): 431-439.

Biehl, Jesse K., Satoshi Yamanaka , Tejal A, Desai, Keneth R. Boheler, and Brenda Russell. "Proliferation of Mouse Embryonic Stem Cell Progeny and the Spontaneous Contractile Activity of

(56) References Cited

OTHER PUBLICATIONS

Cardiomyocytes Are Affected by Microtopography." Developmental Dynamics. 238. (2009): 1964-1973.
Brunauer, Stephen, P.H. Emmett, and Edward Tellet. "Adsorption of Gases in Multimolecular Layers." Journal of the American Chemical Society 60 (1938): 309-319.
Chandler, David L.. "PhysOrg.com." Harnessing nanopatterns: Tiny textures can produce big differences. N.p., Sep. 24, 2009. Web. Dec. 1, 2009. <http://www.physorg.com/news173004362.html>.
Choi, Chang-Hwan, Sepideh H. Hagvall, Bengamin M. Wu, James C.Y. Dunn, Ramin E. Beygui, and Chang-Jin "CJ" Kim. "cell interaction with three-dimensional sharp-tip nanotopography." Biomaterials. 28.9 (2007): 1672-1679.
Chun, YW, D Khang, KM Haberstroh, and TJ Webster. "The role of polymer nanosurcace roughness and the submicron pores in improving bladder urothelial cell density and inhibiting calcium oxalate stone formation." Nanotechnology. 20.8 (2009): 85104.
Cohn, Abby. "Drug Delivery, Nanoscale." Innovations. 3.4 (2009).
Curtis, Adam SG, Matthew Dalby, and Nikolaj Gadegaard. "Cell signaling arising from nanotopography: implicatinos for nanomedicaldevices." Nanomedicine. 1.1 (2006): 67-72.
Dalby, Matthew J. "Nanostructured surfaces: cell engineering and cell biology." Nanomedicine. 4.3 (2009): 247-248.
Dalby, Matthew J., Catherine C. Berry, Mathis O. Riehle, Doncan S. Sutherland, Hossein Agheli, and Adam S.G. Curtis . "Attempted endocytosis of nano-environment produced by colloidal lithography by human fibroblasts." Experimental Cell Research. 295. (2004): 387-394.
Dalby, Matthew J., Mathis Riehle, Duncan Sutherland, Hossein Agheli, and Adam S.G. Curtis. "Nano-Topography Induces Mechanotransduction in Human Fibroblasts." European Cells and Materials. 6.2 (2003): 31.
Dalby, Matthew J., Stephen J. Yarwood, Mathis O. Riehle, Heather J.H. Johnstone, Stanley Affrossman, and Adam S.G. Curtis . "In -creasing Fibroblast Response to Materials Using Nanotopography: Morphological and Genetic measurements of Cell Response to 13-nm-High Polymer Demixed Islands." Experimental Cell Research. 276.1 (2002): 1-9.
Fischer, Kathleen E., Benjamin J. Aleman, Sarah L. Tao, R. Hugh Daniels, Esther M. Li, Mark D. Bunger, Ganesh Nagaraj, Parminder Singh, et al. "Biomimetic Nanowire Coatings for Next Generation Adhesive Drug Delivery Systems." Nano Letters. 9.2 (2009): 716-720.
Hart, A, N Gadegaard, C.D.W. Wilkinson, R.O.C Oreffo, and M.J. Dalby. "Filapodial Sensing of Nanotopography in Osteoprogenitor Cells." European Cells and Materials. 10.2 (2005): 65.
He, et al., "The anatase phase of nanotopography titania plays an important role on osteoblast cell morphology and proliferation". Journal of Mater. Sci: Mater Med (2008), 19:3465-3472.
Hu, Wenchuang, Fern Yoon, Adam Crouch, Li Tao, Heather Hillebrenner, Jagadeesh Setti Guthi, Moon Kim, and Jinming Gao. "Surface Energy Induced Patterning of Polymer Nanostructures for Cancer Diagnosis and Therapy." IEEE Nano 2007 Conference Paper. (2007).
Lim, Jung Yul, Joshua C Hansen, Christopher A Siedlecki, James Runt, and Henry J Donahue. "Human foetal osteoblastic cell response to polymer-demixed nanotopographic interfaces." Journal of the Royal Society Interface. 2.2 (2005): 97-108.
Mandavi, Alborz, Lino Ferreira, Cathryn Sundback, et al. "A biodegradable and biocompatible gecko-inspired tissue adhesive." PNAS. 105.7 (2008): 2307-2312.
Abstract—Meirelles, L, F Currie, M Jacobsson, T Albrektsson, and A Wennerberg. "The effect of chemical and nanotopographical modifications on the early stages of osseointegration." International Journal of Oral and Maxillofacial Implants. 23.4 (2008): 641-647.
Abstract—Mendelsohn, Adam, and Tejal Desai. "Inorganic Nanoporous Membranes for Immunoisolated Cell-Based Drug Delivery." Therapeutic Applications of Cell Microencapsulation.
Ng, C.K.M., W.L. Poon, W.Y. Li, T. Cheung, S.H. Cheng, and K.N. Yu. "Study of substrate topographical effects on epithelial cell behavior using etched alpha-particle tracks on PADC films." Nuclear Instruments and Methods in Physics Research Section B: Beam Interactions with Materials and Atoms. 266.14 (2008): 3247-3256.
Orr, Galya, David J. Panther, Jaclyn L. Phillips, Barbara J. Tarasevich, Alice Dohnalkova, Justin G. Teeguarden, and Joel G. Pounds . "Submicrometer and Nanoscale Inorganic Particles Exploit the Actin Machinery to Be Propelled along Microvilli-likestructures into Alveolar Cells." American Chemical Society NANO. 1.5 (2007): 463-475.
Peng, Lily, Adam D. Mendelsohn, Thomas J. LaTempa, Sorachon Yoriya, Craig A. Grimes, and Tejal A. Desai. "Long-Term Small Molecule and Protein Elution from TiO2 Nanotubes." Nano Letters. 9.5 (2009): 1932-1936.
Peng, Lily, Matthew G. Eltgroth, Thomas J. Latempa, Craig A. Grimes, and Tejal A. Desai. "The effect of TiO2 nanotubes on endothelial function and smooth muscle proliferation." Journal of Biomaterials. 30. (2009): 1268-1272.
Sapra, Bharti, Subheet Jain, and A.K. Tiwary. "Transdermal Delivery of Carvedilol Containing Glycyrrhizin and Chitosan as Permeation Enhancers:Biochemical, Biophysical, Microscopic and Pharmacodynamic Evaluation." Drug Delivery. 15.7 (2008): 443-454.
Abstract—Sapra, Bharti, Subheet Jain, and A.K. Tiwary. "Transdermal delivery of carvedilol in rats:probing the percutaneous permeation enhancement mechanism of soybean extract-chitosan mixture." Drug Delivery. 35.10 (2009): 1230-1241.
Sapra, Bharti, Subheet Jain, and Ashok K. Tiwary. "Effect of Asparagus racemous Extract on Transdermal Delivery of Carvedilol:A Mechanistic Study." American Association of Pharmaceutical Scientists PharmSciTech. 10.1 (2009): 199.
Teo, Benjamin KK, et al. "The effect of micro and nanotopography on endocytosis in drug and gene delivery systems", Biomaterials, 32 (2011), 9866-9875.
Thakar, Rahul G., Matthew G. Chown, Anuj Patel, Lily Peng, Sanjay Kumar, and Tejal A. Desai. "Contractility-Dependent Modulation of Cell Proliferation and Adhesion by Microscale Topographical Cues." Small. 4.9 (2008): 1416-1424.
Valenta, Claudia, and Barbara G. Auner. "The use of polymers for dermal and transdermal delivery." European Journal of Pharmaceutics and Biopharmaceutics. 58.2 (2004): 279-289.
Wang, Min, and Yan Lu. "Nano patterned PDMS for periodontal ligament fibroblast culture." Surface and Coatings Technology. 204.4 (2009): 525-530.
Wei, Song, and Chen Hong. "Protein adsorption on materials surfaces with nano-topography." Chinese Science Bulletin. 52.23 (2007): 3169-3173.
Wood, M.A. "Colloidal lithography and current fabrication techniques producing in-plane nanotopography for biological applications." Journal of the Royal Society Interface. 4.12 (2007): 1-17.
Abstract—Yao, Chang, and Thomas J Webster. "Nano-Surface Modification on Titanium Implants for Drug Delivery." Materials Research Society. (2007).
Yim, Evelyn K.F., Ron M. Reano, Stella w. Pang, Albert F. Yee, Christopher S. Chen, and Kam W. Leong . "Nanopattern-induced changes in morphology and motility of smooth muscle cells." Journal of Biomaterials. 58.1 (2005).
The Journal of American Chem. Soc., vol. LX, Jan.-Jun. 1938.
Abstract of Japanese Patent—JP2008237673, dated Oct. 9, 2008, 1 page.
Abstract of Japanese Patent—JP2009207733, dated Sep. 17, 2009, 1 page.
Abstract of Japanese Patent—JPH08337521, dated Dec. 24, 1996, 2 pages.
Inkyu Park et al., Towards the silicon nanowire-based sensor for intracellular biochemical detection, 6 pages, Apr. 1, 2007, Biosensors and Bioelectronics, vol. 22, No. 9-10.
Supplementary European Search Report dated Sep. 9, 2013, 12 pages.
Al-Qallaf et al., "Optimizing Microneedle Arrays to Increase Skin Permeability for Transdermal Drug Delivery," Interdisciplinary Transport Phenomena V: Ann. N.Y. Acad. Sci., 2009, pp. 1-12.
Abstract of Japanese Patent—JP2001238964, dated Sep. 4, 2001, 1 page.

(56) References Cited

OTHER PUBLICATIONS

Abstract of Japanese Patent—JP2008511382, dated Apr. 17, 2008, 2 pages.
Berliner et al., "Impact of Transdermal Fentanyl on Quality of Life in Rheumatoid Arthritis", Clinical Journal of Pain, 2007, 23(6): 530-534.
Biggs et al., "Interactions with Nanoscale Topography: Adhesion quantification and signal transduction in cells of osteogenic and multipotent lineage," Journal of Biomedical Materials Research Part A, 2008, pp. 195-208.
Kumar et al. "Transdermal Drug Delivery System: An Overview," International Journal of Pharmaceutical Sciences Review and Research 3.2 (2010): 49-54.
Enbrel (etanercept) FDA safety data, available online at https://www.accessdata.fda.gov/drugsatfda_docs/label/2008/enbrel_pi.pdf (accessed Jul. 22, 2019). (Year: 2008).

\* cited by examiner square packing hexagonal packing

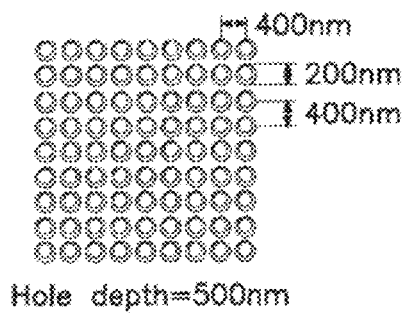 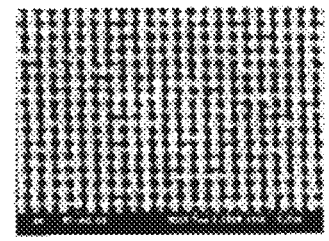
FIG. 25A
FIG. 25A'
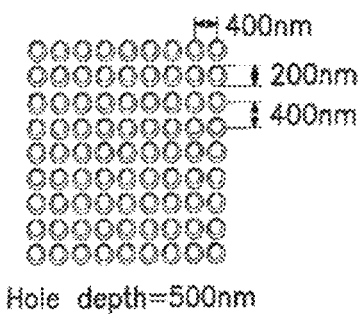 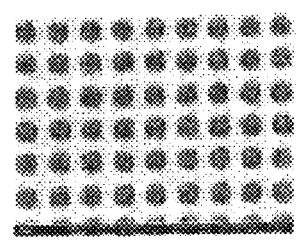
FIG. 25B
FIG. 25B'
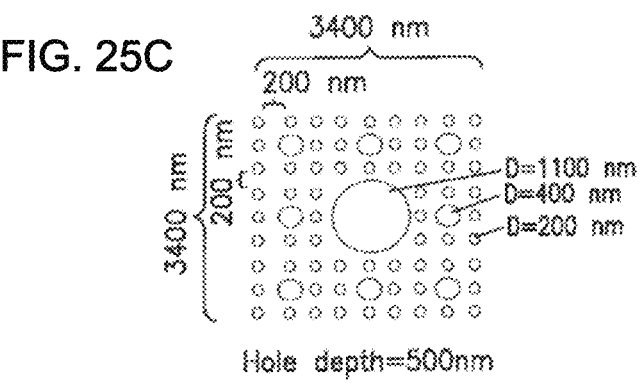 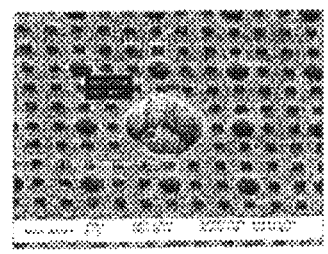
FIG. 25C
FIG. 25C'
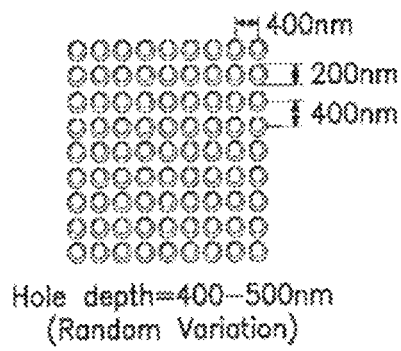 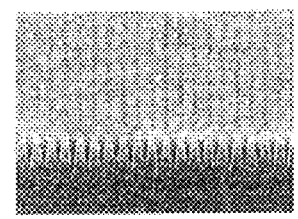
FIG. 25D
FIG. 25D'

FIG. 25E
NTTAT2
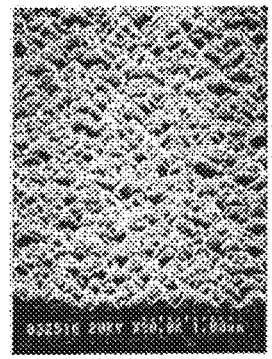
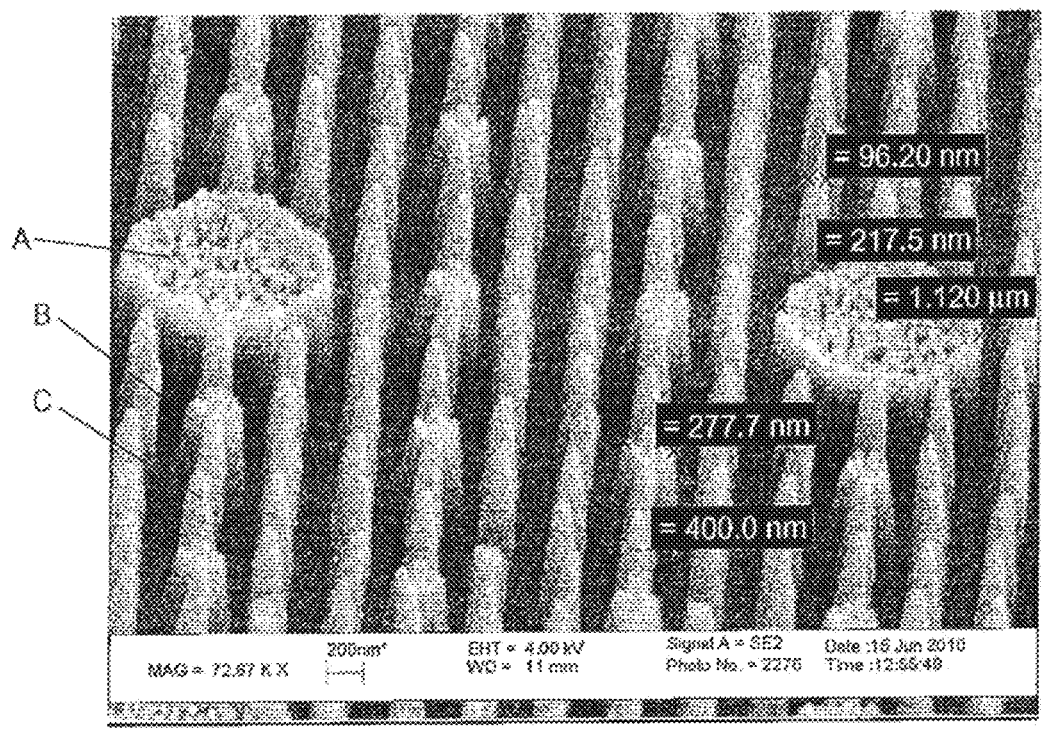
FIG. 26

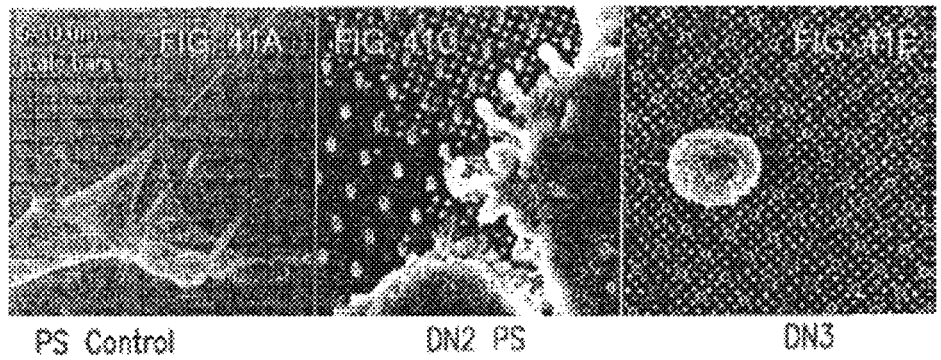
| FIG. 41A | FIG. 41C | FIG. 41E |
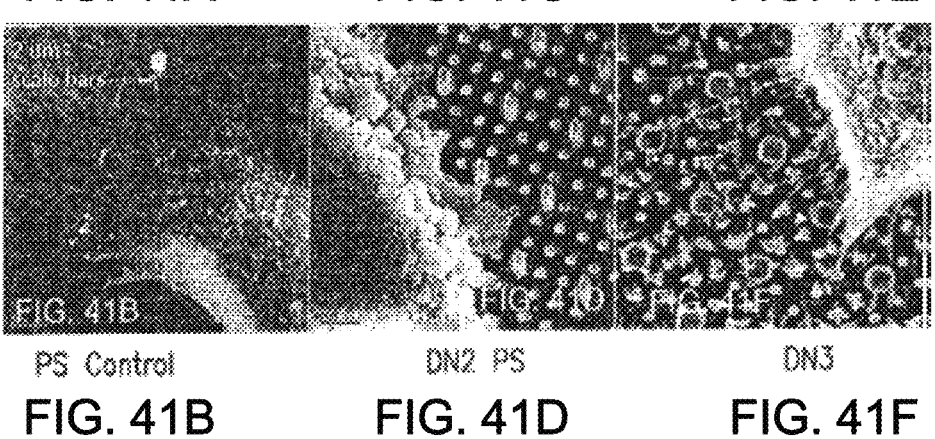
| FIG. 41B | FIG. 41D | FIG. 41F |
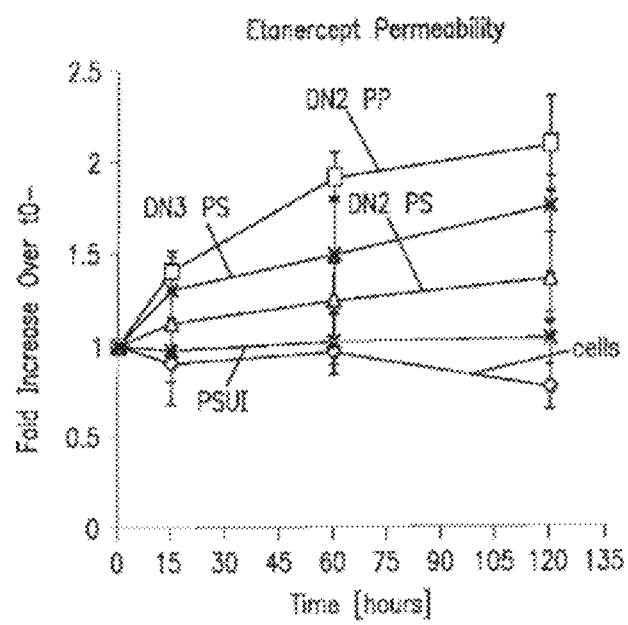
FIG. 42

NANOPATTERNED MEDICAL DEVICE WITH ENHANCED CELLULAR INTERACTION

CROSS-REFERENCE TO RELATED APPLICATION

This application is a continuation application of U.S. patent application Ser. No. 13/095,489, filed on Apr. 27, 2011, the entire contents and disclosure of which are hereby incorporated by reference herein in their entirety. U.S. patent application Ser. No. 13/095,489 claims priority to U.S. Provisional Patent Application No. 61/328,723, filed on Apr. 28, 2010, U.S. Provisional Patent Application No. 61/411,071, filed on Nov. 8, 2010, and U.S. Provisional Patent Application No. 61/435,939, filed on Jan. 25, 2011, the entire contents and disclosure of which are hereby incorporated by reference herein in their entirety.

BACKGROUND

Targeted drug delivery in which an agent (e.g., a drug or a therapeutic) is provided in an active state to a specific cell or tissue type at effective concentrations is a long sought goal. Many difficulties must be overcome to reach this goal. For instance, an agent must first be successfully delivered to the desired target. Primary delivery methods presently used include oral delivery and injections. However, injections are painful and both methods tend to provide bursts of agents rather than a preferred steady-state delivery. Additionally, the human body has developed many systems to prevent the influx of foreign substances such as enzymatic degradation in the gastrointestinal tract, structural components that prevent absorption across epithelium, hepatic clearance, and immune and foreign body response.

Transdermal delivery materials have been developed in an attempt to provide a painless route for delivery of active agents over a sustained period. In order to be successful, a transdermal scheme must deliver an agent across the epidermis, which has evolved with a primary function of keeping foreign substances out. The outermost layer of the epidermis, the stratum corneum, has structural stability provided by overlapping corneocytes and crosslinked keratin fibers held together by coreodesmosomes and embedded within a lipid matrix, all of which provides an excellent barrier function. Beneath the stratum corneum is the stratum granulosum, within which tight junctions are formed between keratinocytes. Tight junctions are barrier structures that include a network of transmembrane proteins embedded in adjacent plasma membranes (e.g., claudins, occludin, and junctional adhesion molecules) as well as multiple plaque proteins (e.g., ZO-1, ZO-2, ZO-3, cingulin, symplekin). Tight junctions are found in internal epithelium (e.g., the intestinal epithelium, the blood-brain barrier) as well as in the stratum granulosum of the skin. Beneath both the stratum corneum and the stratum granulosum lays the stratum spinosum. The stratum spinosum includes Langerhans cells, which are dendritic cells that may become fully functioning antigen-presenting cells and may institute an immune response and/or a foreign body response to an invading agent.

In spite of the difficulties of crossing the natural boundaries, progress has been made in attaining delivery of active agents, e.g., transdermal delivery. Unfortunately, transdermal delivery methods are presently limited to delivery of low molecular weight agents that have a moderate lipophilicity and no charge. Even upon successful crossing of the natural boundary, problems still exist with regard to maintaining the activity level of delivered agents and avoidance of foreign body and immune response.

The utilization of supplementary methods to facilitate transdermal delivery of active agents has improved this delivery route. For instance, microneedle devices have been found to be useful in transport of material into or across the skin. In general, a microneedle device includes an array of needles that may penetrate the stratum corneum of the skin and reach an underlying layer. Examples of microneedle devices have been described in U.S. Pat. No. 6,334,856 to Allen, et al., and in U.S. Pat. No. 7,226,439 to Prausnitz, et al., both of which are incorporated herein by reference. However, as discussed above, transdermal delivery presents additional difficulties beyond the barrier of the stratum corneum. In particular, once an agent has been delivered to a targeted area, it is still necessary that proper utilization take place without destruction of the agent or the instigation of an immune response. For instance, encouraging endocytosis of an active agent targeted to the cell interior presents difficulties.

Researchers have gained understanding of the molecular world in which delivery activities occur in an attempt to overcome such problems. For instance, chitosan has been found to be effective in opening tight junctions in the intestinal epithelium (see, e.g., Sapra, et al., *AAPS Pharm. Sci. Tech.*, 10(1), March, 2009; Kaushal, et al., *Sci. Pharm.*, 2009; 77; 877-897), and delivery of active agents via endocytosis of labeled nanoparticles has been described (see, e.g., U.S. Pat. No. 7,563,451 to Lin, et al., and U.S. Pat. No. 7,544,770 to Haynie). In addition, the nanotopography of a surface adjacent to a cell has been found to affect adhesive characteristics between the two as well as to effect cell behavior including morphology, motility, cytoskeleton architecture, proliferation, and differentiation (see, e.g., Hart, et al., *European Cells and Materials*, Vol. 10, Suppl. 2, 2005; Lim et al., *J R Soc Interface*, Mar. 22, 2005, 2(2), 97-108; Yim, et al., *Biomaterials*, September, 2005, 26(26), 5405-5413). As an extension of this initial research, nanotopography of supporting substrates has been examined for use in tissue engineering (see, e.g., U.S. Patent Application Publication Nos. 2008/0026464 to Borenstein, et al. and 2008/0311172 to Schapira, et al.).

While the above describe improvements in the art, further room for improvement exists. For instance, devices and methods that provide efficient delivery of active agents while decreasing potential immune and foreign body response to both the delivery device and the delivered agents would be beneficial.

SUMMARY

In one aspect, a medical device for delivering a drug compound through a stratum corneum and to a subdermal location generally comprises a support having an aperture, an array of microneedles that extend outwardly from the support, a plurality of nanostructures associated with each microneedle of the array of microneedles, and a reservoir wherein the drug compound is retained. At least one microneedle contains a shaft extending from the support. The shaft includes a tip configured to penetrate the stratum corneum. The shaft defines a channel extending from the support to the tip. The channel is in at least partial alignment with the aperture of the support. At least some of the microneedles each have a cross-sectional dimension of from about 1 micrometer to about 1 millimeter. At least some of the nanostructure have a cross-sectional dimension less than about 500 nanometers and greater than about 5 nanometers as well as an aspect ratio of from about 0.2 to about 5. The reservoir is in fluid communication with the aperture of the support and the channel of the microneedle for delivery of the drug compound to the subdermal location.

In another aspect, a medical device for delivering a drug compound through a stratum corneum and to a subdermal location generally comprises a support having an aperture, an array of microneedles extending outwardly from the support, a plurality of nanostructures associated with each microneedle of the array of microneedles, and a reservoir wherein the drug compound is retained. At least one microneedle contains a shaft extending from the support. The shaft includes a tip configured to penetrate the stratum corneum. The shaft defines a channel extending from the support to the tip. The channel is in at least partial alignment with the aperture of the support. At least some of the microneedles of the array of microneedles each have a cross-sectional dimension of from about 1 micrometer to about 1 millimeter. The plurality of nanostructures are arranged in a pattern having a fractal dimension greater than about 1. At least some of the nanostructures of the plurality of nanostructures have a cross-sectional dimension less than about 500 nanometers and greater than about 5 nanometers as well as an aspect ratio of from about 0.2 to about 5. The reservoir is in fluid communication with the aperture of the support and the channel of the microneedle for delivery of the drug compound to the subdermal location.

In yet another aspect, a medical device for delivering a drug compound through a stratum corneum and to a subdermal location generally comprises a microneedle having an exterior surface, a nanopatterned film disposed on the exterior surface of the microneedle, and a reservoir wherein the drug compound is retained. The microneedle contains a shaft defining a channel extending therethrough. The nanopatterned film comprises a plurality of nanostructures. Each nanostructure has (i) a cross-sectional dimension less than about 500 nanometers and greater than about 5 nanometers and (ii) an aspect ratio from about 0.2 to about 5. The reservoir is in fluid communication with the channel of the microneedle for delivery of the drug compound to the subdermal location.

BRIEF DESCRIPTION OF THE DRAWINGS

A full and enabling disclosure of the subject matter, including the best mode thereof, directed to one of ordinary skill in the art, is set forth more particularly in the remainder of the specification, which makes reference to the appended figures in which:

FIGS. 12A-12B schematically illustrate one embodiment of a device in which FIG. 12A is an exploded perspective view showing the device separate from a release liner and FIG. 12B is a perspective view of the assembled device.

FIGS. 25A-25E illustrate several nanotopography patterns as described herein. FIGS. 25A'-25D' illustrate images that are associated with the schematic representations of FIGS. 25A-25D.

FIG. 26 is an SEM of a film including a nanopatterned surface.

FIGS. 41A-41F are scanning electron microscopy (SEM) images of cells cultured on nanopatterned surfaces as described herein.

FIG. 42 illustrates the effects on permeability to etanercept in a monolayer of cells on polypropylene or polystyrene films patterns with nanopatterns as described herein.

FIG. 47A is a cross section of skin that was in contact with a transdermal device defining a nanotopography thereon, and FIG. 47B is a cross section of skin that was in contact with a transdermal device including no pattern of nanotopography formed thereon.

DETAILED DESCRIPTION OF REPRESENTATIVE EMBODIMENTS

Figure 1:
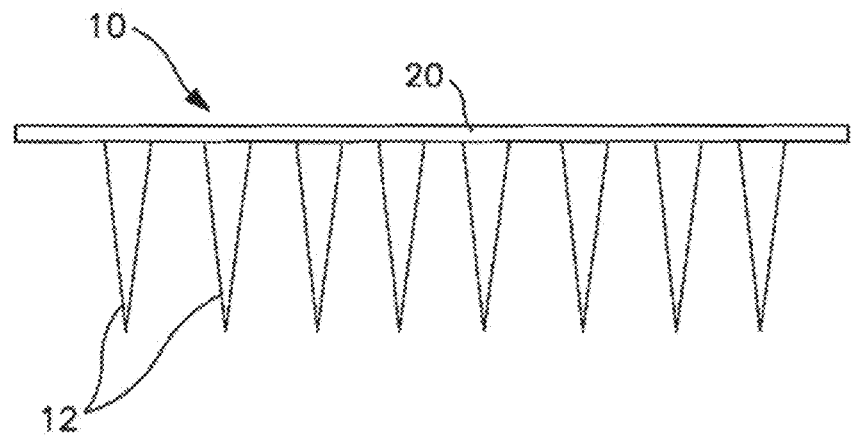
FIG. 1 illustrates one embodiment of a microneedle device.

Reference now will be made in detail to various embodiments of the disclosed subject matter, one or more examples of which are set forth below. Each example is provided by way of explanation, not limitation. In fact, it will be apparent to those skilled in the art that various modifications and variations may be made in the present disclosure without departing from the scope or spirit of the subject matter. For instance, features illustrated or described as part of one embodiment may be used on another embodiment to yield a still further embodiment. Thus, it is intended that the present disclosure covers such modifications and variations as come within the scope of the appended claims and their equivalents.

A medical device is disclosed herein that includes a pattern of structures fabricated on a surface, at least a portion of which are fabricated on a nanometer scale. As utilized herein, the term 'fabricated' generally refers to a structure that has been specifically designed, engineered, and/or constructed so as to exist at a surface of the medical device and is not to be equated with a surface feature that is merely an incidental product of the device formation process. Thus, there will be a predetermined pattern of nanostructures on the surface of the microneedles.

The medical device may be constructed from a variety of materials, including metals, ceramics, semiconductors, organics, polymers, etc., as well as composites thereof. By way of example, pharmaceutical grade stainless steel, titanium, nickel, iron, gold, tin, chromium, copper, alloys of these or other metals, silicon, silicon dioxide, and polymers may be utilized. Typically, the device is formed of a biocompatible material that is capable of carrying a pattern of structures as described herein on a surface. The term "biocompatible" generally refers to a material that does not substantially adversely affect the cells or tissues in the area where the device is to be delivered. It is also intended that the material does not cause any substantially medically undesirable effect in any other areas of the living subject. Biocompatible materials may be synthetic or natural. Some examples of suitable biocompatible materials, which are also biodegradable, include polymers of hydroxy acids such as lactic acid and glycolic acid polylactide, polyglycolide, polylactide-co-glycolide, copolymers with polyethylene glycol, polyanhydrides, poly(ortho)esters, polyurethanes, poly(butyric acid), poly(valeric acid), and poly(lactide-co-caprolactone). Other suitable materials may include, without limitation, polycarbonate, polymethacrylic acid, ethylenevinyl acetate, polytetrafluorethylene, and polyesters. The device may likewise be non-porous or porous in nature, may be homogeneous or heterogeneous across the device with regard to materials, geometry, solidity, and so forth, and may have a rigid fixed or a semi-fixed shape.

Regardless of the materials employed, the medical device may be used for interaction with tissue, such as in delivery of a bioactive agent to a cell. For example, the medical device may be used to deliver an agent to the tissue or to one or more cell types of the tissue, for structural support of a tissue, for removal of a portion or component of the tissue, and so forth. The medical device may be used in one embodiment for transport of a substance across one or more layers of the skin. During use, the device may interact with surrounding biological components and regulate or modulate (i.e., change) intracellular and/or intercellular signal transduction associated with cell/cell interactions, endocytosis, inflammatory response, and so forth. For instance, through interaction between the nanotopography on a surface of the medical device and surrounding biological materials or structures, the device may regulate and/or modulate membrane potential, membrane proteins, and/or intercellular junctions (e.g., tight junctions, gap junctions, and/or desmosomes). The device may be utilized for transdermal delivery of agents or withdrawal of materials without instigating a foreign body or immune response.

Figure 2:
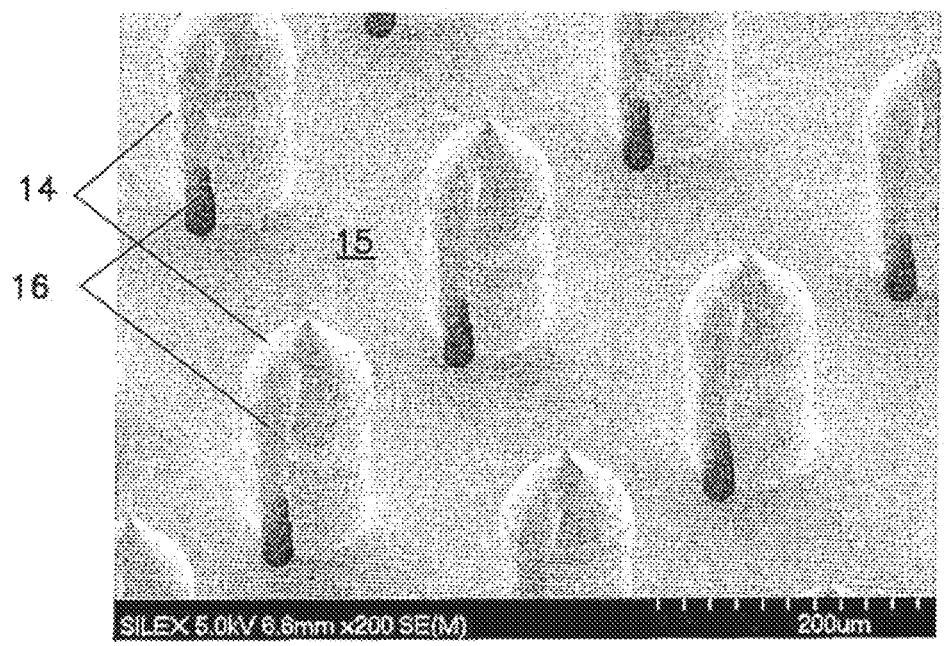
FIG. 2 illustrates another embodiment of a microneedle device.

In one embodiment, the device is a microneedle or a microneedle array, although it should be understood that the devices are not limited to microneedles. Microneedles may be useful in transport of material across biological barriers such as the skin, the blood-brain barrier, mucosal tissues, blood and lymph vessels, and so forth. FIG. 1 illustrates a typical microneedle device 10. As may be seen, the device includes an array of individual needles 12; each formed to a size and shape so as to penetrate a biological barrier without breakage of the individual microneedles. Microneedles may be solid, as in FIG. 1, porous, or may include a hollow portion. A microneedle may include a hollow portion, e.g., an annular bore that may extend throughout all or a portion of the needle, extending parallel to the direction of the needle or branching or exiting at a side of the needle, as appropriate. For example, FIG. 2 illustrates an array of microneedles 14 each including a channel 16 in a side of the needles as may be utilized for, e.g., delivery of an agent to a subdermal location. For instance, a channel 16 may be in at least partial alignment with an aperture in base 15 so as to form a junction between the aperture and channel 16 allowing the passage of a substance through the channel 16.

The dimensions of the channel 16, when present, can be specifically selected to induce capillary flow of a drug compound. Capillary flow generally occurs when the adhesive forces of a fluid to the walls of a channel are greater than the cohesive forces between the liquid molecules. Specifically, capillary pressure is inversely proportional to the cross-sectional dimension of the channel 16 and directly proportional to the surface tension of the liquid, multiplied by the cosine of the contact angle of the fluid in contact with the material forming the channel. Thus, to facilitate capillary flow in the patch, the cross-sectional dimension (e.g., width, diameter, etc.) of the channel 16 may be selectively controlled, with smaller dimensions generally resulting in higher capillary pressure. For example, in some embodiments, the cross-sectional dimension of the channel typically ranges from about 1 micrometer to about 100 micrometers, in some embodiments from about 5 micrometers to about 50 micrometers, and in some embodiments, from about 10 micrometers to about 30 micrometers. The dimension may be constant or it may vary as a function of the length of the channel 16. The length of the channel may also vary to accommodate different volumes, flow rates, and dwell times for the drug compound. For example, the length of the channel may be from about 10 micrometers to about 800 micrometers, in some embodiments from about 50 micrometers to about 500 micrometers, and in some embodiments, from about 100 micrometers to about 300 micrometers. The cross-sectional area of the channel may also vary. For example, the cross-sectional area may be from about 50 square micrometers to about 1,000 square micrometers, in some embodiments from about 100 square micrometers to about 500 square micrometers, and in some embodiments, from about 150 square micrometers to about 350 square micrometers. Further, the aspect ratio (length/cross-sectional dimension) of the channel may range from about 1 to about 50, in some embodiments from about 5 to about 40, and in some embodiments from about 10 to about 20. In cases where the cross-sectional dimension (e.g., width, diameter, etc.) and/or length vary as a function of length, the aspect ratio can be determined from the average dimensions.

It should be understood that the number of microneedles shown in the figures is for illustrative purposes only. The actual number of microneedles used in a microneedle assembly may, for example, range from about 500 to about 10,000, in some embodiments from about 2,000 to about 8,000, and in some embodiments, from about 4,000 to about 6,000.

An individual microneedle may have a straight or a tapered shaft. In one embodiment, the diameter of a microneedle may be greatest at the base end of the microneedle and taper to a point at the end distal the base. A microneedle may also be fabricated to have a shaft that includes both a straight (untapered) portion and a tapered portion.

A microneedle may be formed with a shaft that is circular or non-circular in cross-section. For example, the cross-section of a microneedle may be polygonal (e.g. star-shaped, square, triangular), oblong, or any other shape. The shaft may have one or more bores and/or channels.

The size of individual needles may be optimized depending upon the desired targeting depth, the strength requirements of the needle to avoid breakage in a particular tissue type, etc. For instance, the cross-sectional dimension of a transdermal microneedle may be between about 10 nanometers (nm) and 1 millimeter (mm), or between about 1 micrometer (μm) and about 200 micrometers, or between about 10 micrometers and about 100 micrometers. The outer diameter may be between about 10 micrometers and about 100 micrometers and the inner diameter of a hollow needle may be between about 3 micrometers and about 80 micrometers. The tip typically has a radius that is less than or equal to about 1 micrometer.

The length of a microneedle will generally depend upon the desired application. For instance, a microneedle may be between about 1 micrometer and about 1 millimeter in length, for instance about 500 micrometers or less, or between about 10 micrometers and about 500 micrometers, or between about 30 micrometers and about 200 micrometers.

An array of microneedles need not include microneedles that are all identical to one another. An array may include a mixture of microneedles having various lengths, outer diameters, inner diameters, cross-sectional shapes, nanostructured surfaces, and/or spacings between the microneedles. For example, the microneedles may be spaced apart in a uniform manner, such as in a rectangular or square grid or in concentric circles. The spacing may depend on numerous factors, including height and width of the microneedles, as well as the amount and type of any substance that is intended to be moved through the microneedles. While a variety of arrangements of microneedles is useful, a particularly useful arrangement of microneedles is a "tip-to-tip" spacing between microneedles of about 50 micrometers or more, in some embodiments about 100 to about 800 micrometers, and in some embodiments, from about 200 to about 600 micrometers.

Referring again to FIG. 1, microneedles may be held on a substrate 20 (i.e., attached to or unitary with a substrate) such that they are oriented perpendicular or at an angle to the substrate. In one embodiment, the microneedles may be oriented perpendicular to the substrate and a larger density of microneedles per unit area of substrate may be provided. However, an array of microneedles may include a mixture of microneedle orientations, heights, materials, or other parameters. The substrate 20 may be constructed from a rigid or flexible sheet of metal, ceramic, plastic or other material. The substrate 20 can vary in thickness to meet the needs of the device, such as about 1000 micrometers or less, in some embodiments from about 1 to about 500 micrometers, and in some embodiments, from about 10 to about 200 micrometers.

Figure 3:
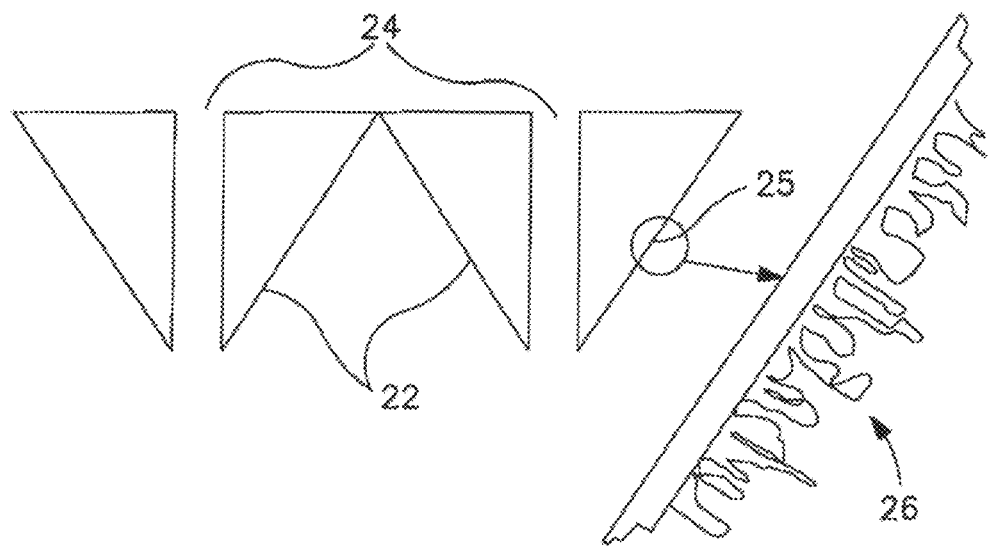
FIG. 3 illustrates one embodiment of a microneedle including a surface that defines a nanotopography that may interact with an extracellular matrix (ECM).

According to the present disclosure, a microneedle surface may define a nanotopography thereon in a random or organized pattern. FIG. 3 schematically illustrates the ends of two representative microneedles 22. Microneedles 22 define a central bore 24 as may be used for delivery of an agent via the microneedles 22. The surface 25 of microneedles 22 define nanotopography 26. In this particular embodiment, the nanotopography 26 defines a random pattern on the surface 25 of the microneedle 22.

A microneedle may include a plurality of identical structures formed on a surface or may include different structures formed of various sizes, shapes and combinations thereof. A predetermined pattern of structures may include a mixture of structures having various lengths, diameters, cross-sectional shapes, and/or spacings between the structures. For example, the structures may be spaced apart in a uniform manner, such as in a rectangular or square grid or in concentric circles. In one embodiment, structures may vary with regard to size and/or shape and may form a complex nanotopography. For example, a complex nanotopography may define a fractal or fractal-like geometry.

As utilized herein, the term "fractal" generally refers to a geometric or physical structure having a fragmented shape at all scales of measurement between a greatest and a smallest scale such that certain mathematical or physical properties of the structure behave as if the dimensions of the structure are greater than the spatial dimensions. Mathematical or physical properties of interest may include, for example, the perimeter of a curve or the flow rate in a porous medium. The geometric shape of a fractal may be split into parts, each of which defines self-similarity. Additionally, a fractal has a recursive definition and has a fine structure at arbitrarily small scales.

As utilized herein, the term "fractal-like" generally refers to a geometric or physical structure having one or more, but not all, of the characteristics of a fractal. For instance, a fractal-like structure may include a geometric shape that includes self-similar parts, but may not include a fine structure at an arbitrarily small scale. In another example, a fractal-like geometric shape or physical structure may not decrease (or increase) in scale equally between iterations of scale, as may a fractal, though it will increase or decrease between recursive iterations of a geometric shape of the pattern. A fractal-like pattern may be simpler than a fractal. For instance, it may be regular and relatively easily described in traditional Euclidean geometric language, whereas a fractal may not.

A microneedle surface defining a complex nanotopography may include structures of the same general shape (e.g., pillars) and the pillars may be formed to different scales of measurement (e.g., nano-scale pillars as well as micro-scale pillars). In another embodiment, a microneedle may include at a surface structures that vary in both scale size and shape or that vary only in shape while formed to the same nano-sized scale. Additionally, structures may be formed in an organized array or in a random distribution. In general, at least a portion of the structures may be nanostructures formed on a nano-sized scale, e.g., defining a cross-sectional dimension of less than about 500 nanometers, for instance less than about 400 nanometers, less than about 250 nanometers, or less than about 100 nanometers. The cross sectional dimension of the nanostructures can generally be greater than about 5 nanometers, for instance greater than about 10 nanometers, or greater than about 20 nanometers. For example, the nanostructures can define a cross sectional dimension between about 5 nanometers and about 500 nanometers, between about 20 nanometers and about 400 nanometers, or between about 100 nanometers and about 300 nanometers. In cases where the cross sectional dimension of a nanostructure varies as a function of height of the nanostructure, the cross sectional dimension can be determined as an average from the base to the tip of the nanostructures, or as the maximum cross sectional dimension of the structure, for example the cross sectional dimension at the base of a cone-shaped nanostructure.

Figure 4:
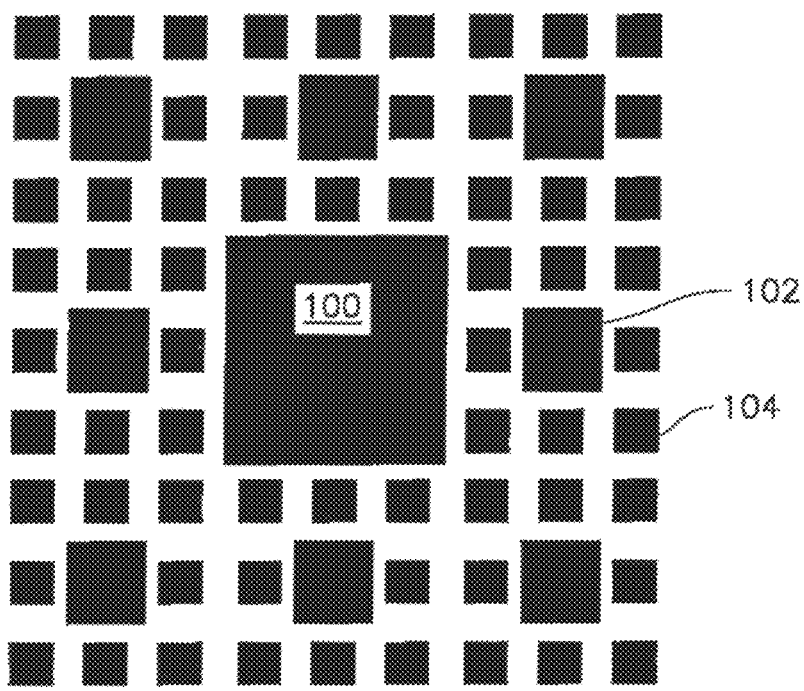
FIG. 4 illustrates one embodiment of a complex pattern that may be formed on a microneedle surface.

FIG. 4 illustrates one embodiment of a complex nanotopography as may be formed on a surface. This particular pattern includes a central large pillar 100 and surrounding pillars 102, 104, of smaller dimensions provided in a regular pattern. As may be seen, this pattern includes an iteration of pillars, each of which is formed with the same general shape, but vary with regard to horizontal dimension. This particular complex pattern is an example of a fractal-like pattern that does not include identical alteration in scale between successive recursive iterations. For example, while the pillars 102 are first nanostructures that define a horizontal dimension that is about one third that of the larger pillar 100, which is a microstructure, the pillars 104 are second nanostructures that define a horizontal dimension that is about one half that of the pillars 102.

A pattern that includes structures of different sizes can include larger structures having a cross-sectional dimension formed on a larger scale, e.g., microstructures having a cross-sectional dimension greater than about 500 nanometers in combination with smaller nanostructures. In one embodiment, microstructures of a complex nanotopography can have a cross-sectional dimension between about 500 nanometers and about 10 micrometers, between about 600 nanometers and about 1.5 micrometers, or between about 650 nanometers and about 1.2 micrometers. For example, the complex nanotopography of FIG. 4 includes micro-sized pillars 100 having a cross sectional dimension of about 1.2 micrometers.

When a pattern includes one or more larger microstructures, for instance, having a cross-sectional dimension greater than about 500 nanometers, determined either as the average cross sectional dimension of the structure or as the largest cross sectional dimension of the structure, the complex nanotopography will also include nanostructures, e.g., first nanostructures, second nanostructures of a different size and/or shape, etc. For example, pillars 102 of the complex nanotopography of FIG. 4 have a cross-sectional dimension of about 400 nanometers, and pillars 104 have a cross-sectional dimension of about 200 nanometers.

A nanotopography can be formed of any number of different elements. For instance, a pattern of elements can include two different elements, three different elements, an example of which is illustrated in FIG. 4, four different elements, or more. The relative proportions of the recurrence of each different element can also vary. In one embodiment, the smallest elements of a pattern will be present in larger numbers than the larger elements. For instance in the pattern of FIG. 4, there are eight pillars 104 for each pillar 102, and there are eight pillars 102 for the central large pillar 100. As elements increase in size, there can generally be fewer recurrences of the element in the nanotopography. By way of example, a first element that is about 0.5, for instance between about 0.3 and about 0.7 in cross-sectional dimension as a second, larger element can be present in the topography about five times or more than the second element. A first element that is approximately 0.25, or between about 0.15 and about 0.3 in cross-sectional dimension as a second, larger element can be present in the topography about 10 times or more than the second element.

The spacing of individual elements can also vary. For instance, center-to-center spacing of individual structures can be between about 50 nanometers and about 1 micrometer, for instance between about 100 nanometers and about 500 nanometers. For example, center-to-center spacing between structures can be on a nano-sized scale. For instance, when considering the spacing of nano-sized structures, the center-to-center spacing of the structures can be less than about 500 nanometers. This is not a requirement of a topography, however, and individual structures can be farther apart. The center-to-center spacing of structures can vary depending upon the size of the structures. For example, the ratio of the average of the cross-sectional dimensions of two adjacent structures to the center-to-center spacing between those two structures can be between about 1:1 (e.g., touching) and about 1:4, between about 1:1.5 and about 1:3.5, or between about 1:2 and about 1:3. For instance, the center to center spacing can be approximately double the average of the cross-sectional dimensions of two adjacent structures. In one embodiment, two adjacent structures each having a cross-sectional dimension of about 200 nanometers can have a center-to-center spacing of about 400 nanometers. Thus, the ratio of the average of the diameters to the center-to-center spacing in this case is 1:2.

Structure spacing can be the same, i.e., equidistant, or can vary for structures in a pattern. For instance, the smallest structures of a pattern can be spaced apart by a first distance, and the spacing between these smallest structures and a larger structure of the pattern or between two larger structures of the pattern can be the same or different as this first distance.

For example, in the pattern of FIG. 4, the smallest structures 104 have a center-to-center spacing of about 200 nanometers. The distance between the larger pillars 102 and each surrounding pillar 104 is less, about 100 nanometers. The distance between the largest pillar 100 and each surrounding pillar 104 is also less than the center-to-center spacing between to smallest pillars 104, about 100 nanometers. Of course, this is not a requirement, and all structures can be equidistant from one another or any variation in distances. In one embodiment, different structures can be in contact with one another, for instance atop one another, as discussed further below, or adjacent one another and in contact with one another.

Structures of a topography may all be formed to the same height, generally between about 10 nanometers and about 1 micrometer, but this is not a requirement, and individual structures of a pattern may vary in size in one, two, or three dimensions. In one embodiment, some or all of the structures of a topography can have a height of less than about 20 micrometers, less than about 10 micrometers, or less than about 1 micrometer, for instance less than about 750 nanometers, less than about 680 nanometers, or less than about 500 nanometers. For instance the structures can have a height between about 50 nanometers and about 20 micrometers or between about 100 nanometers and about 700 nanometers. For example, nanostructures or microstructures can have a height between about 20 nm and about 500 nm, between about 30 nm and about 300 nm, or between about 100 nm and about 200 nm, though it should be understood that structures may be nano-sized in a cross sectional dimension and may have a height that may be measured on a micro-sized scale, for instance greater than about 500 nm. Micro-sized structures can have a height that is the same or different from nano-sized structures of the same pattern. For instance, micro-sized structures can have a height of between about 500 nanometers and about 20 micrometers, or between about 1 micrometer and about 10 micrometers, in another embodiment. Micro-sized structures may also have a cross sectional dimension on a micro-scale greater than about 500 nm, and may have a height that is on a nano-sized scale of less than about 500 nm.

The aspect ratio of the structures (the ratio of the height of a structure to the cross sectional dimension of the structure) can be between about 0.15 and about 30, between about 0.2 and about 5, between about 0.5 and about 3.5, or between about 1 and about 2.5. For instance, the aspect ratio of the nanostructures may fall within these ranges.

Figure 5:
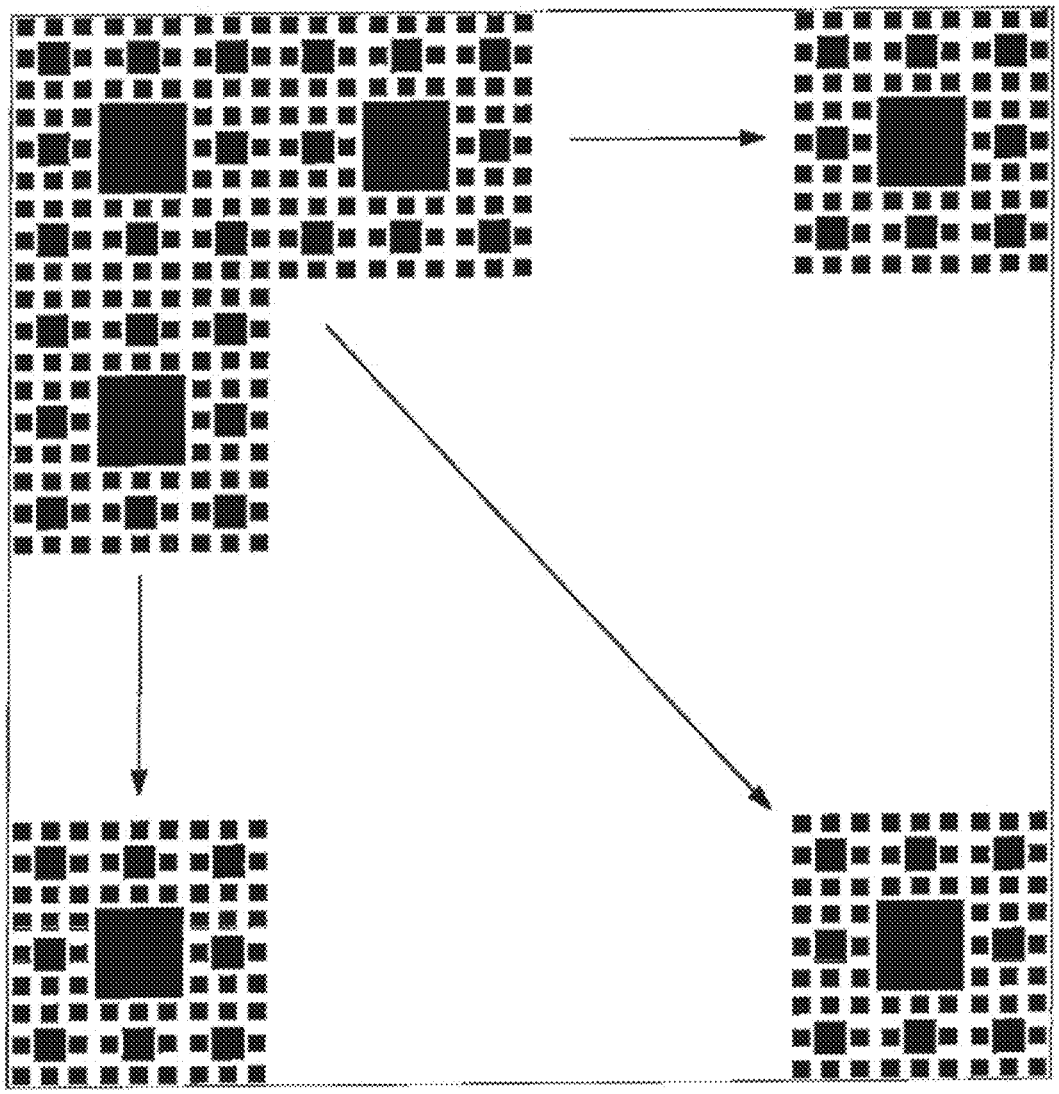
FIG. 5 illustrates a pattern including multiple iterations of the complex pattern of FIG. 4.

The device surface may include a single instance of a pattern, as shown in FIG. 4, or may include multiple iterations of the same or different patterns. For example, FIG. 5 illustrates a surface pattern including the pattern of FIG. 4 in multiple iterations over a surface.

The formation of nanotopography on a surface may increase the surface area without a corresponding increase in volume. Increase in the surface area to volume ratio is believed to improve the interaction of a surface with surrounding biological materials. For instance, increase in the surface area to volume ratio is believed to encourage mechanical interaction between the nanotopography and surrounding proteins, e.g., extracellular matrix (ECM) proteins and/or plasma membrane proteins.

In general, the surface area to volume ratio of the device may be greater than about 10,000 cm$^{-1}$, greater than about 150,000 cm$^{-1}$, or greater than about 750,000 cm$^{-1}$. Determination of the surface area to volume ratio may be carried out according to any standard methodology as is known in the art. For instance, the specific surface area of a surface may be obtained by the physical gas adsorption method (B.E.T. method) with nitrogen as the adsorption gas, as is generally known in the art and described by Brunauer, Emmet, and Teller (J. Amer. Chem. Soc., vol. 60, February, 1938, pp. 309-319), incorporated herein by reference. The BET surface area can be less than about 5 m$^2$/g, in one embodiment, for instance between about 0.1 m$^2$/g and about 4.5 m$^2$/g, or between about 0.5 m$^2$/g and about 3.5 m$^2$/g. Values for surface area and volume may also be estimated from the geometry of molds used to form a surface, according to standard geometric calculations. For example, the volume can be estimated according to the calculated volume for each pattern element and the total number of pattern elements in a given area, e.g., over the surface of a single microneedle.

For a device that defines a complex pattern nanotopography at a surface, the nanotopography may be characterized through determination of the fractal dimension of the pattern. The fractal dimension is a statistical quantity that gives an indication of how completely a fractal appears to fill space as the recursive iterations continue to smaller and smaller scale. The fractal dimension of a two dimensional structure may be represented as:

$$D = \frac{\log N(e)}{\log(e)}$$

where N(e) is the number of self-similar structures needed to cover the whole object when the object is reduced by 1/e in each spatial direction.

Figure 6:
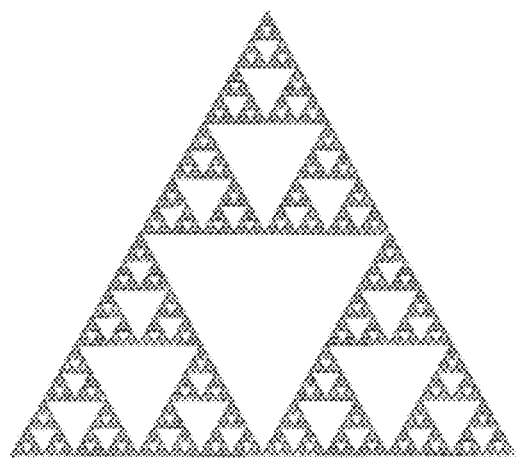
FIG. 6 illustrates a Sierpinski triangle fractal.

For example, when considering the 2 dimensional fractal known as the Sierpenski triangle illustrated in FIG. 6, in which the mid-points of the three sides of an equilateral triangle are connected and the resulting inner triangle is removed, the fractal dimension is calculated as follows:

$$D = \frac{\log N(e)}{\log(e)}$$

$$D = \frac{\log 3}{\log 2}$$

$$D \approx 1.585$$

Thus, the Sierpenski triangle fractal exhibits an increase in line length over the initial two dimensional equilateral triangle. Additionally, this increase in line length is not accompanied by a corresponding increase in area.

The fractal dimension of the pattern illustrated in FIG. 4 is approximately 1.84. In one embodiment, nanotopography of a surface of the device may exhibit a fractal dimension of greater than about 1, for instance between about 1.2 and about 5, between about 1.5 and about 3, or between about 1.5 and about 2.5.

Figure 7A:
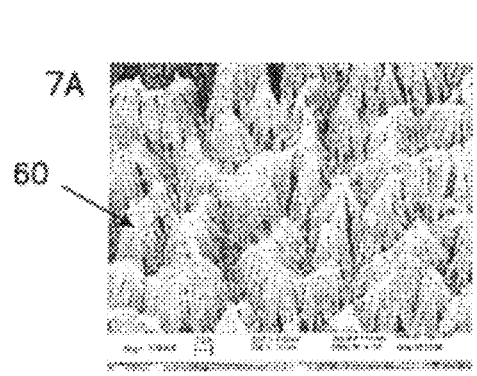
FIGS. 7A-7D illustrate complex fractal and fractal-like nanotopographies.
Figure 7B:
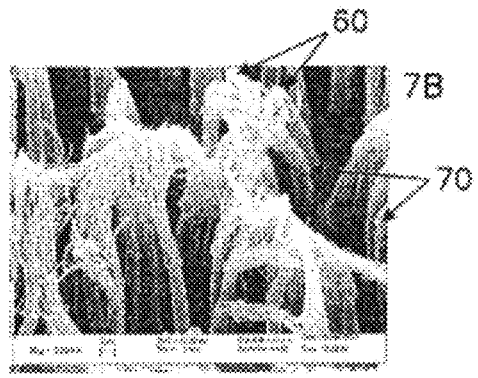

FIGS. 7A and 7B illustrate increasing magnification images of another example of a complex nanotopography. The nanotopography of FIGS. 7A and 7B includes an array of fibrous-like pillars 70 located on a substrate. At the distal end of each individual pillar, the pillar splits into multiple smaller fibers 60. At the distal end of each of these smaller fibers 60, each fiber splits again into multiple filaments (not visible in FIGS. 7A and 7B). Structures formed on a surface that have an aspect ratio greater than about 1 may be flexible, as are the structures illustrated in FIGS. 7A and 7B, or may be stiff.

Figure 7C:
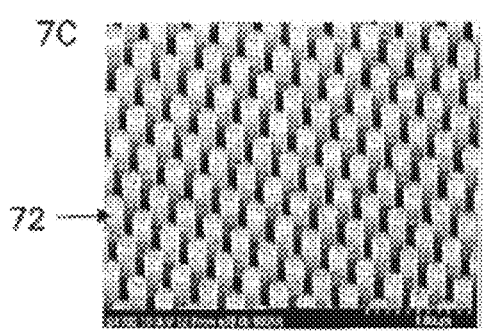
Figure 7D:
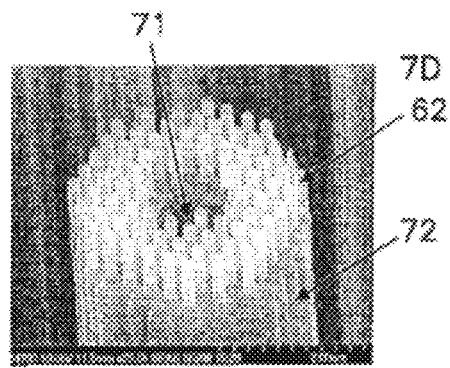

FIGS. 7C and 7D illustrate another example of a complex nanotopography. In this embodiment, a plurality of pillars 72 each including an annular hollow therethrough 71 are formed on a substrate. At the distal end of each hollow pillar, a plurality of smaller pillars 62 is formed. As may be seen, the pillars of FIGS. 7C and 7D maintain their stiffness and upright orientation. Additionally, and in contrast to previous patterns, the smaller pillars 62 of this embodiment differ in shape from the larger pillars 72. Specifically, the smaller pillars 62 are not hollow, but are solid. Thus, nanotopography including structures formed to a different scale need not have all structures formed with the same shape, and structures may vary in both size and shape from the structures of a different scale.

Figure 8:
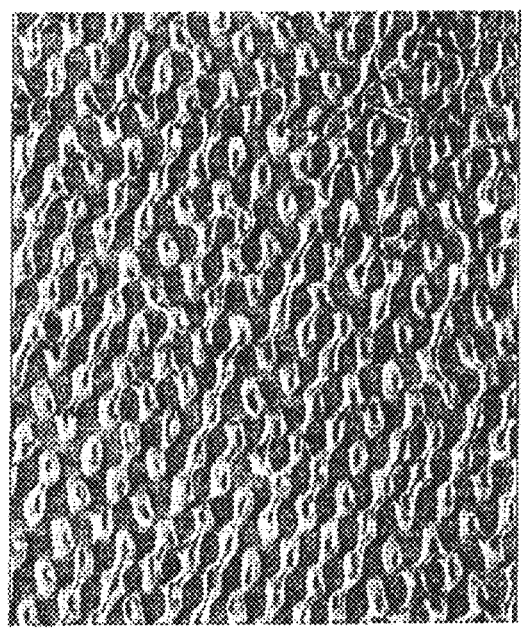
FIG. 8 illustrates another complex pattern that may be formed on a microneedle surface.

FIG. 8 illustrates another pattern including nano-sized structures as may be formed on the device surface. As may be seen, in this embodiment, individual pattern structures may be formed at the same general size, but with different orientations and shapes from one another.

In addition to or alternative to those methods mentioned above, a surface may be characterized by other methods including, without limitation, surface roughness, elastic modulus, and surface energy.

Methods for determining the surface roughness are generally known in the art. For instance, an atomic force microscope process in contact or non-contact mode may be utilized according to standard practice to determine the surface roughness of a material. Surface roughness that may be utilized to characterize a microneedle can include the average roughness ($R_A$), the root mean square roughness, the skewness, and/or the kurtosis. In general, the average surface roughness (i.e., the arithmetical mean height of the surface are roughness parameter as defined in the ISO 25178 series) of a surface defining a fabricated nanotopography thereon may be less than about 200 nanometers, less than about 190 nanometers, less than about 100 nanometers, or less than about 50 nanometers. For instance, the average surface roughness may be between about 10 nanometers and about 200 nanometers, or between about 50 nanometers and about 190 nanometers.

The device may be characterized by the elastic modulus of the nanopatterned surface, for instance by the change in elastic modulus upon the addition of a nanotopography to a surface. In general, the addition of a plurality of structures forming nanotopography on a surface can decrease the elastic modulus of a material, as the addition of nano-sized structures on a surface will lead to a reduction in continuity of the surface and a related change in surface area. As compared to a similar surface formed according to the same process and of the same materials, but for a pattern of nanotopography on the surface, the device including nanotopography thereon can exhibit a decrease in elastic modulus of between about 35% and about 99%, for instance between about 50% and about 99%, or between about 75% and about 80%. By way of example, the effective compression modulus of a nanopatterned surface can be less than about 50 MPa, or less than about 20 MPa. In one embodiment the effective compression modulus can be between about 0.2 MPa and about 50 MPa, between about 5 MPa and about 35 MPa, or between about 10 MPa and about 20 MPa. The effective shear modulus can be less than about 320 MPa, or less than about 220 MPa. For instance, the effective shear modulus can be between about 4 MPa and about 320 MPa, or between about 50 MPa and about 250 MPa, in one embodiment.

The device including nanotopography thereon may also exhibit an increase in surface energy as compared to a similar microneedle that does not have a surface defining a pattern of nanotopography thereon. For instance, a microneedle including a nanotopography formed thereon can exhibit an increase in surface energy as compared to a similar microneedle of the same materials and formed according to the same methods, but for the inclusion of a pattern of nanotopography on a surface. For instance, the water contact angle of a surface including a nanotopography thereon can be greater than about 80°, greater than about 90°, greater than about 100°, or greater than about 110°. For example, the water contact angle of a surface can be between about 80° and about 150°, between about 90° and about 130°, or between about 100° and about 120°, in one embodiment.

Figure 9A:
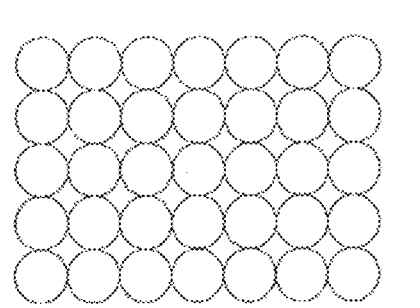
FIGS. 9A-9C illustrate exemplary packing densities as may be utilized for nano-sized structures as described herein including a square packing design (FIG. 9A), a hexagonal packing design (FIG. 9B), and a circle packing design (FIG. 9C).
Figure 9B:
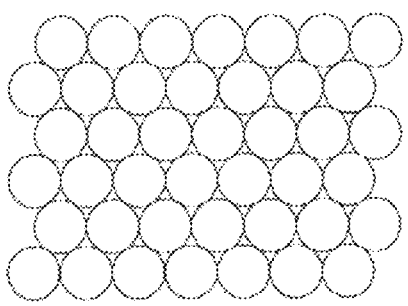
Figure 9C:
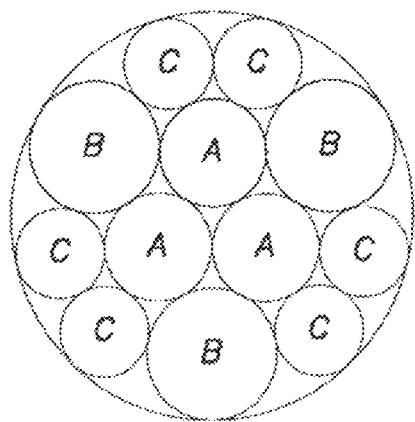

When forming nanostructures on the surface of the device, the packing density of the structures may be maximized. For instance, square packing (FIG. 9A), hexagonal packing (FIG. 9B), or some variation thereof may be utilized to pattern the elements on a substrate. When designing a pattern in which various sized elements of cross sectional areas A, B, and C are adjacent to one another on a substrate, circle packing as indicated in FIG. 9C may be utilized. Of course, variations in packing density and determination of associated alterations in characteristics of a surface are well within the abilities of one of skill in the art.

During use, a microneedle device may interact with one or more components of the dermal connective tissue. Connective tissue is the framework upon which the other types of tissue, i.e., epithelial, muscle, and nervous tissues, are supported. Connective tissue generally includes individual cells held within the ECM. The ECM, in turn, includes the ground substance (e.g., the minerals of bone, the plasma of blood, etc.) and the fibrous component including collagen, fibronectin, laminins, etc. Connective tissue may assume widely divergent architectures, ranging from blood, in which the fibrous component is absent and the ground substance is fluid, to dense connective tissue as is found in the skin, which includes a relatively high proportion of extracellular fibers (e.g., collagen) and may contain little of the other connective tissue components. There are many specialized types of connective tissue in skin, one example being elastic tissue, in which elastic fibers are the major component of the tissue and the amount of factors commonly found in other types of connective tissue, such as collagen and proteoglycans, may be minimal.

The nanotopography of a microneedle surface may provide improved interaction between the microneedle and biological components of the dermal connective tissue of the delivery area. For instance, microneedles of a transdermal device may interact directly with ECM proteins and/or individual cells such as keratinocytes, Langerhans cells of the stratum spinosum or the undifferentiated basal cells of the stratum germinativum. Longer needles on transdermal devices may be utilized to access components of the dermis, for instance blood cells of the capillary bed. Due to the improved interaction between the device and local biological components, the surrounding tissue may be less likely to exhibit a foreign body response, which may decrease local inflammation and improve delivery of active agents. In one embodiment, the device can play a more active roll in agent delivery. For instance, interaction between a nanotopography and the surrounding biological components can encourage delivery of high molecular weight materials, for instance through opening of tight junctions in the stratum granulosum.

While not wishing to be held to any particular theory, it is believed that the nanotopography facilitates improved interaction with biological components through two mechanisms. According to one mechanism, a nanotopography may facilitate the ability of a microneedle to mimic the ECM at a delivery site. For instance, the nanotopography of a microneedle can mimic one or more components of the basement membrane at a delivery site. In use, a cell may contact the nanotopography of a microneedle and react in a similar fashion to typical contact with the natural structure (e.g., the basement membrane protein) that the nanotopography mimics. Accordingly, the device may directly interact with a cell to regulate or modulate (i.e., change) cell behavior, e.g., cell signal transduction, thereby improving delivery of an agent across natural barriers as well as improving endocytosis of agents delivered by the device.

According to a second mechanism, a nanotopography may interact with non-cellular biological components of the local connective tissue such as ECM proteins. For instance, ECM proteins may be adsorbed and desorbed from the surface of a microneedle. The adsorption/desorption of ECM proteins may alter the chemistry of the local environment, which can lead to alterations in cell behavior. According to this second mechanism, the device may indirectly affect the behavior of a cell. For example, the adsorption of one or more ECM proteins at the surface of the device can indirectly regulate or modulate intracellular and/or intercellular signal transduction.

Due to improved interaction with surrounding biological components, the devices can facilitate improved uptake of a delivered agent. For example, the pharmacokinetic (PK) profile (i.e., the profile of absorption through the epithelial membranes) of a protein therapeutic can be enhanced through utilization of a device including a pattern of nanotopography. By way of example, a protein therapeutic having a molecular weight of over 100 kDa, for instance between about 100 kDa and about 200 kDa, or about 150 kDa, can be delivered transdermally via a patch defining a nanotopography thereon. In one embodiment, a patch can be utilized to deliver a single dose of the protein therapeutic, for instance between about 200 and about 500 µL, or about 250 µL. Following attachment of the transdermal patch to the skin, the recipient can exhibit a PK profile that reflects a rapid rise in blood serum concentration up to between about 500 and about 1000 nanograms therapeutic per milliliter per square centimeter of patch area, for instance between about 750 and about 850 nanograms therapeutic per milliliter per square centimeter patch area, within about 1 to about 4 hours of administration. This initial rapid rise in blood serum level, which reflects rapid uptake of the therapeutic across the dermal barrier, can be followed by a less rapid decline of blood serum concentration over between about 20 and about 30 hours, for instance over about 24 hours, down to a negligible blood serum concentration of the therapeutic. Moreover, the rapid uptake of the delivered therapeutic can be accompanied by little or no inflammation. Specifically, in addition to promoting improved delivery of an agent across a transdermal barrier, the devices can also limit foreign body response and other undesirable reactions, such as inflammation. Use of previously known devices, such as transdermal patches with no nanotopography defined at the skin contacting surface, often led to local areas of inflammation and irritation.

Structures of the nanotopography may mimic and/or interact with one or more ECM protein such as collagen, laminin, fibronectin, etc. This may directly or indirectly alter a cell membrane protein with regard to one or more characteristics such as conformation, free energy, local density. Exemplary cell membrane proteins include, without limitation, integrins, viniculin or other focal adhesion proteins, clathrin, membrane receptors such as G protein coupled receptors, etc. This alteration may induce changes at the cell surface and/or within the cell via downstream effects through the cytoskeleton and within the cytoplasm.

Cells in the local area surrounding the device may maintain an anti-inflammatory microenvironment as the device may better mimic the local environment either directly or indirectly due to protein adsorption at the surface. Thus, materials may be delivered by use of the device without development of a foreign body or immune response.

Specific cell types that may be directly or indirectly affected by the presence of a microneedle may include cells of the surrounding dermal connective tissue. For instance, a microneedle surface defining nanotopography may be located in an area that includes Langerhans cells, macrophages, and/or T-cells without triggering a foreign body or immune response. Langerhans cells may take up and process an antigen to become a fully functional antigen presenting cell. Macrophages and T-cells play a central role in the initiation and maintenance of the immune response. Once activated by pathological or immunogenic stimuli, for instance via a Langerhans cell, T-cells may release IL-2, IL-4, INF-γ, and other inflammatory cytokines. Macrophages respond in the process by releasing a host of inflammatory mediators, including TNF-α, IL-1, IL-8, IL-11, IL-12, nitric oxide, IL-6, GM-CSF, G-CSF, M-CSF, IFN-α, IFN-β and others. Released cytokines activate other immune cells and some may also act as independent cytotoxic agents. Excessive release of macrophage and T-cell derived inflammatory mediators may lead to damage of normal cells and surrounding tissues.

Without wishing to be bound to any particular theory, it is believed that through interaction with a nanopatterned substrate, individual cells can up- or down-regulate the production of certain cytokines, including certain chemokines. Through that alteration in expression profile, cellular response to a drug delivery device can be minimized. For example, inflammation and/or foreign body response can be minimized through upregulation of one or more anti-inflammatory cytokines and/or down-regulation of one or more pro-inflammatory cytokines. Many cytokines have been characterized according to effect on inflammation. Pro-inflammatory cytokines that may demonstrate altered expression profiles when expressing cells are affected by the presence of a device including a nanotopography fabricated thereon can include, without limitation, IL-1α, IL-1β, IL-2, IL-6, IL-8, IL-10, IL-12, IL16, MIG, MIP-1α, MIP-1β, KC, MCP-1, TNF-α, GM-CSI, VEGF, and the like. Anti-inflammatory cytokines that may demonstrate an altered expression profile can include, without limitation, IL-1ra, IL-4, IL-10, IL-13, and the like. Cytokines associated with foreign body response that can demonstrate an altered expression profile can include, without limitation, IL-4, IL-10, IL-13, and so forth.

Nitric oxide is recognized as a mediator and regulator of inflammatory responses. By influencing the local environment, a microneedle may limit the release of nitric oxide from surrounding cells. This may be beneficial as nitric oxide may possess toxic properties toward an active agent being delivered and may also have deleterious effects on the subject's own tissue (Korhonen et al., Curr Drug Targets Inflamm Allergy 4(4): 471-9, 2005). Nitric oxide may also interact with molecular oxygen and superoxide anion to produce reactive oxygen species (ROS) that may modify various cellular functions. These indirect effects of nitric oxide have a significant role in inflammation; in which nitric oxide may be produced in high amounts by inducible nitric oxide synthase (iNOS) and ROS may be synthesized by activated inflammatory cells.

Nitric oxide may be produced by keratinocytes, fibroblasts, endothelial cells, and possibly others, any of which may be directly or indirectly affected by the nanotopography of a microneedle. Inhibition of nitric oxide synthesis as may be provided by the nanotopography of a microneedle surface may affect wound contraction, alter collagen organization, and alter neoepidermis thickness. Mast cell migration and angiogenesis in wounds may also be affected by inhibition of nitric oxide. Due to variable pathways of regulation, and without being bound to any particular theory, the device may increase nitric oxide production and/or retard nitric oxide degradation, whereas in another embodiment, the device may decrease nitric oxide production and/or hasten nitric oxide degradation.

Interaction of the device with components of a cell network or layer of the epidermis may modulate (i.e., change) the structure of intercellular junctions therein. An intracellular junction may be at least one junction selected from the group consisting of tight junctions, gap junctions, and desmosomes. By way of example, interaction between biological components and structures of a nanotopography may modulate proteins of a cellular network so as to induce the opening of tight junctions of the stratum granulosum, thereby providing improved delivery of an active agent across the epidermis, and in one particular embodiment, a high molecular weight active agent.

The nanotopography of the device may mimic and/or adsorb one or more components of the ECM. In general, the ECM includes both the interstitial matrix and the basement membrane. The interstitial matrix is composed of complex mixtures of proteins and proteoglycans and, in the case of bone, mineral deposits. The basement membrane includes both basal lamina and reticular lamina and anchors and supports the epithelium and the endothelium. The specific make-up of the ECM may vary depending upon the specific tissue type, but in general will include a variety of collagens, laminins, fibronectin, and elastins. Thus, the nanotopography of the device may be designed to interact with components of a specific location or alternatively may be more generally designed, e.g., to interact with components of the dermal structure common to most skin.

Structures of the nanotopography can interact with collagen, which is a common basement membrane protein found in dermal ECM. Collagens are insoluble, extracellular glycoproteins that are found in all animals and are the most abundant proteins in the human body. They are essential structural components of most connective tissues, including cartilage, bone, tendons, ligaments, fascia and skin. To date, 19 types of collagens have been found in humans. The major types include Type I, which is the chief component of tendons, ligaments, and bones; Type II, which represents more than 50% of the protein in cartilage, and is also used to build the notochord of vertebrate embryos; Type III, which strengthens the walls of hollow structures like arteries, the intestine, and the uterus, and Type IV, which forms the basal lamina of epithelia. A meshwork of Type IV collagens provides the filter for the blood capillaries and the glomeruli of the kidneys. The other 15 types of collagen, while being much less abundant, are no less important to the function of the ECM.

The basic unit of collagens is a polypeptide that often follows the pattern Gly-Pro-Y or Gly-X-Hyp, where X and Y may be any of various other amino acid residues. The resulting polypeptide is twisted into an elongated, left-handed helix. When synthesized, the N-terminal and C-terminal of the polypeptide have globular domains, which keep the molecule soluble.

As utilized herein, the term "polypeptide" generally refers to a molecular chain of amino acids and does not refer to a specific length of the product. Thus, peptides, oligopeptides and proteins are included within the definition of polypeptide. This term is also intended to include polypeptides that have been subjected to post-expression modifications such as, for example, glycosylations, acetylations, phosphorylations and so forth. As utilized herein, the term "protein" generally refers to a molecular chain of amino acids that is capable of interacting structurally, enzymatically or otherwise with other proteins, polypeptides or any other organic or inorganic molecule.

Common amino acid symbol abbreviations as described below in Table 1 are used throughout this disclosure.

TABLE 1

| Amino Acid | One letter symbol | Abbreviation |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Tropocollagen is a subunit of larger collagen aggregates such as fibrils. It is approximately 300 nanometers long and 1.5 nanometers in diameter, made up of three polypeptide strands, each possessing the left-handed helix conformation.

Nanotopography of the device surface can interact with and/or mimic tropocollagen as well as collagen. In one embodiment, a nanotopography may be more complex and can mimic and/or interact with both tropocollagen on a nanoscale and collagen on a microscale. For instance, a larger component of a nanotopography can mimic the three left-handed helices of tropocollagen that are twisted together into a right-handed coiled coil, a triple helix or "super helix", a cooperative quaternary structure stabilized by numerous hydrogen bonds. With type I collagen and possibly all fibrillar collagens if not all collagens, each triple-helix associates into a right-handed super-super-coil that is referred to as the collagen microfibril. Each microfibril is interdigitated with its neighboring microfibrils. In some collagens (e.g., Type II), the three polypeptides that make up the microfibril are identical. In other collagens (e.g., Type I), two polypeptides of one kind (gene product) assemble with a second similar but different polypeptide.

Laminin is another common basement membrane protein of the skin that may be found in the local area of the device. Laminin is one of a family of heterotrimer protein complexes formed from various combinations of different α, β, and γ subunit chains. Laminins in general may be found primarily in the basement membranes of the ECM and interact with other matrix macromolecules to contribute to cell differentiation, movement and maintenance. The different laminin chains, α-1 through α-5, β-1 through β-3, and γ-1 through γ-3 may theoretically form many different trimeric isoforms, but the existence of only 15 of the possible isoforms has been confirmed.

Laminins are in the shape of a cross including three shorter arms and one long arm. The three shorter arms are particularly good at binding to other laminin molecules, leading to formation of sheets in the basement membrane. The long arm generally is the cell binding locale, binding to cell membranes and other ECM molecules, which helps anchor organized tissue cells to the membrane.

Laminins further include subdomains with specific geometries. For instance, the terminal portion of the laminin-332 α3 chain, the G domain, is further subdivided into 5 subdomains, G1, G2, G3, G4, and G5. The G subdomains of the laminin-332 α3 chain have been shown to be necessary for adherence of laminin-332 to cells which have certain receptor integrins on their cell surface. Accordingly, nano-sized structures of a nanotopography may mimic one or more subdomains of laminin. In a more complex pattern, these nano-sized structures may be combined with larger structures that may mimic an entire laminin protein. A nanotopography may also or alternatively adsorb/desorb laminin and thereby affect the local environment.

A nanotopography may interact with fibronectin, which is involved in tissue repair, embryogenesis, blood clotting and cell migration and adhesion. In the ECM fibronectin exists as an insoluble glycoprotein dimer. The structure of fibronectin is rod-like, composed of three different types of homologous, repeating modules, Types I, II, and III. These modules, though all part of the same amino acid chain, are typically envisioned as "beads on a string," each one joined to its neighbors by short linkers.

Twelve Type I modules make up the amino-terminal and carboxy-terminal region of the protein, and are involved mainly in fibrin and collagen binding. Only two type II modules are found in fibronectin. They are instrumental in binding collagen. The most abundant module in fibronectin is Type III, which contains the RGD fibronectin receptor recognition sequence along with binding sites for other integrins and heparin. Depending on the tissue type and/or cellular conditions, the fibronectin molecule is made up of 15-17 type III modules. In addition, there is a module that does not fall into any of these categories, called IIICS. This module, along with EDB and EDA (both type III modules), is regulated through alternative splicing of FN pre-mRNA. Fibronectin molecules may form two disulphide bridges at their carboxy-termini, producing a covalently-linked dimer. A cell in contact with the nanotopography of a microneedle device may interact with the device in similar fashion to the normal interaction of the cell with fibronectin.

Yet another common ECM protein that a device can interact with is elastin and/or a polypeptide fragment of elastin. Elastin is the protein constituent of connective tissue responsible for the elasticity and recoil of the tissue. Moreover, elastin is quite abundant in connective tissue. Tropoelastin chains are naturally cross-linked together to form elastic fibers. Unlike collagen, elastin molecules may uncoil into a more extended conformation when the fiber is stretched and will recoil spontaneously as soon as the stretching force is relaxed. Elastin is primarily composed of Gly, Val, Ala, and Pro. It defines an irregular or random coil conformation.

In addition to the common dermal fibrous proteins, the nanotopography of the device may mimic and/or adsorb other ECM components such as proteoglycans. Proteoglycans are glycoproteins but consist of much more carbohydrate than protein; that is, they are huge clusters of carbohydrate chains often attached to a protein backbone. Several sugars are incorporated in proteoglycans. The most abundant one is N-acetylglucosamine (NAG). The long chains of sugar residues are attached to serine residues in the protein backbone; that is, they are "O-linked". Sulfate groups are also added to the sugars prior to secretion. Examples of common ECM proteoglycans include, without limitation, chondroitin sulfate, heparan sulfate, keratan sulfate, and hyaluronic acid (which has no protein component).

A nanotopography on a surface may directly and/or indirectly affect a cell in the local area of the device. This may include a cell of a barrier layer that lies between the skin surface and the delivery site of an agent to be delivered by a microneedle device as well as a cell to which an agent is to be delivered. Specific effects on a cell due to the presence of the device may include alteration of a conformation, ligand binding activity, or a catalytic activity of a membrane associated protein.

Presence of the device may modulate cellular membrane conductivity, including, in one aspect, whole-cell conductance. Moreover, modulating whole-cell conductance may include modulating at least one of linear and non-linear voltage-dependent contribution of the whole-cell conductance. The device may modulate at least one of cellular membrane potential and cellular membrane conductivity. For instance, the device may directly or indirectly affect a calcium dependent cellular messaging pathway or system.

The nanotopography of the device may affect a component of a plasma membrane, which may affect signaling pathways that are downstream effectors of transcription factors. For instance, through mimicking or interacting with a component of the ECM, the device may affect genetic transcription and/or translation within a local cell. Presence of the device may affect location and/or conformation of membrane proteins. This may in turn affect free energy of the local environment, leading to encouragement of endocytosis of an active agent delivered by the device. Presence of the device may affect the formation of junctions between cells, e.g., tight junctions, leading to improved delivery of agents across a biological barrier.

It is believed that the device may directly or indirectly affect a cell via a membrane associated protein. Membrane associated proteins may include at least one of, without limitation, surface receptors, transmembrane receptors, ion channel proteins, intracellular attachment proteins, cellular adhesion proteins, integrins, etc. According to certain aspects, a transmembrane receptor may be a G-Protein Coupled Receptor (GPCR). For instance, the device may mimic an ECM component that interacts with a GPCR that in turn interacts with a G protein α subunit. A G protein α subunit may be any of a $G\alpha_s$, $G\alpha_i$, $G\alpha_q$, and $G\alpha_{12}$. In interacting with a component of the ECM, the device may affect cadherins, focal adhesions, desmosomes, integrins, clathrin, caveolin, TSLP receptor, β-2 adrenergic receptor, bradykinin receptor, ion channel proteins, and so forth. In one embodiment, presence of a microneedle may modulate junction adhesion molecules including, without limitation, JAM 2 and 3, GJA1, 3, 4 and 5 (junctional adherins), occludin (OCLN), claudins (e.g., CLDN 3, 5, 7, 8, 9, 10), and tight junction protein 1 (TJP1).

The device may influence cellular activity not only at the cell surface, but internally as well. For instance, the device may influence a focal adhesion. Focal adhesions are large assemblies of materials that may include 100 or more different proteins at any one time. They are dynamic in most cell types and provide a route for the transmission of information, both mechanical and chemical, from the ECM to the inner cell. Modification of focal adhesions takes place upon changes in the molecular composition, the physical structure, as well as physical forces present in the ECM.

Focal adhesions allow connection between the cytoskeleton and the ECM and are generally considered to be a signaling hub for both mechanical force and chemical signal transmission. The bulk of focal adhesions are beneath the cellular membrane, with connection to the ECM generally via integrins, though communication may also be via other transmembrane materials including hyaluronan and heparin-sulfate binding proteins.

Integrins are a large family of obligate heterodimeric transmembrane glycoproteins that attach cells to ECM proteins (e.g., laminin) of the basement membrane or to ligands on other cells. The nanotopography of the device can affect integrin at the plasma membrane to affect the cell behavior, for instance via a focal adhesion. Integrins contain large (a) and small (13) subunits of sizes 120-170 kDa and 90-100 kDa, respectively. In mammals, 18 α and β subunits have been characterized. Some integrins mediate direct cell to cell recognition and interactions. Integrins contain binding sites for divalent cations $Mg^{2+}$ and $Ca^{2+}$, which are necessary for their adhesive function. Mammalian integrins form several subfamilies sharing common β subunits that associate with different α subunits. Both the α and β subunits contain two separate tails, both of which penetrate the plasma membrane and possess small cytoplasmic domains. The exception is the β-4 subunit which has a cytoplasmic domain of 1088 amino acids, one of the largest known cytoplasmic domains of any membrane protein. The penetrating portions may interact with proteins within a focal adhesion to communicate information with regard to the ECM to the cytoskeleton and the inner cell. Outside the plasma membrane, the α and β chains lie close together along a length of about 23 nanometers, with the final 5 nanometers N-termini of each chain forming a ligand-binding region for the ECM.

Primary proteins known within focal adhesions that may be affected by the presence of a nanotopography in the area of the cell surface include vinculin, paxilin, talin, α-actinin, and zyxin. The focal adhesion proteins transmit information to the cytoskeleton, for instance via interaction with actin, and throughout the cytoplasm. Focal adhesions are in a constant state of flux, however, and proteins are continually associating and disassociating with the complex, relating information from the ECM to other parts of the cell. The dynamic assembly and disassembly of focal adhesions from the formation of focal complexes at the leading edge of the lamellipodia to the dissolution of the focal adhesion at the trailing edge of the cell is a central role in cell migration. The activation of Src kinase due to extracellular mechanical forces exerted on the inner cell via focal adhesion is an indication of the role focal adhesions play in sensing of mechanical forces of the ECM. Accordingly, the device may modulate activity internal to the cell, including downstream functions involved with cell migration via plasma membrane proteins associated with focal adhesions.

Other cell surface structures that nanotopography of the device may affect include membrane proteins involved in endocytosis. For instance, upon interaction with the cell membrane, the device may exhibit increased adhesion energy due to the nanotopography of the contacting surface. The adhesion energy may mimic that of typical receptor-ligand binding.

While not wishing to be bound to any particular theory, it is believed that upon adhesion between the surface of the device and an endocytosis mediating receptor, other endocytosis mediating receptors in the cell membrane may diffuse from a pre-adhesion uniform distribution on the cell membrane to the adhesion site. These membrane proteins may then adhere to the device surface and thereby lower the free energy of interaction between the cell surface and the device. The lower free energy may encourage endocytosis of agents at the cell surface, e.g., active agents delivered via the device. Specifically, when adhesion occurs between the device surface and a receptor, the released energy, i.e., the increased free energy, may drive wrapping of the membrane around particles at or near the adhesion site. Alternatively, adsorption of non-cellular components of the ECM to the surface of the device may alter the local chemistry, leading to an increase in endocytic activity by cells in the area. Endocytosis pathways as may be mediated due to the presence of the device may be subdivided into four categories including clathrin-mediated endocytosis, caveolae, macropinocytosis, and phagocytosis.

Clathrin-mediated endocytosis is mediated by small vesicles about 100 nanometers in diameter that have a morphologically characteristic crystalline coat of a complex of proteins that mainly associate with the cytosolic protein clathrin. These clathrin-coated vesicles (CCVs) are found in virtually all cells and form clathrin-coated pits on the plasma membrane. Clathrin-coated pits may include increased concentration of large extracellular molecules that have different receptors responsible for the receptor-mediated endocytosis of ligands, e.g. low density lipoprotein, transferrin, growth factors, antibodies and many others.

Nanotopography of the device may affect membrane proteins associated with caveolae. Caveolae are membrane endocytosis formations that are only slightly less common than clathrin-coated pits, and exist on the surface of many, but not all cell types. They consist of the cholesterol-binding protein caveolin (Vip21) with a bilayer enriched in cholesterol and glycolipids. Caveolae are smaller than CCVs, about 50 nanometers in diameter, and form flask-shape pits in the membrane. They may constitute up to a third of the plasma membrane area of the cells of some tissues, being especially abundant in fibroblasts, adipocytes, and endothelial cells as may be found in the skin. Uptake of extracellular molecules is believed to be specifically mediated via receptors in caveolae as may be affected by nanotopography of a microneedle.

Macropinocytosis, which usually occurs from highly ruffled regions of the plasma membrane, describes the pulling in of the cell membrane to form a pocket, which then pinches off into the cell to form a large vesicle (0.5-5 µm in diameter) filled with large volume of extracellular fluid and molecules within it (equivalent to 103 to 106 CCVs). The filling of the pocket occurs in a non-specific manner. The vesicle then travels into the cytosol and fuses with other vesicles such as endosomes and lysosomes.

Phagocytosis describes the binding and internalization of particulate matter larger than around 0.75 µm in diameter, such as small-sized dust particles, cell debris, micro-organisms and even apoptotic cells, which only occurs in specialized cells. These processes involve the uptake of larger membrane areas than clathrin-mediated endocytosis and the caveolae pathway.

Nanotopography of the device may also affect cadherins of a cell surface. Cadherins are a family of receptors generally involved in mediation of calcium-dependent homophilic cell-cell adhesion. Cadherins are of primary importance during embryogenesis, but also play a role in forming stable cell to cell junctions and maintaining normal tissue structure in adults. Cadherins are a superfamily of transmembrane proteins grouped by the presence of one or more cadherin repeats in their extracellular domains. Arrays of these approximately 110 residue domains form the intermolecular surfaces responsible for the formation of cadherin-mediated cell-cell interactions. Structural information from the analysis of several cadherin domains indicates that calcium ions bind at sites between adjacent cadherin repeats (CRs), forming a rigid rod. Cadherins typically include five tandem repeated extracellular domains, a single membrane-spanning segment and a cytoplasmic region.

In one embodiment, the device may affect E-cadherin that is found in epithelial tissue. E-cadherin includes 5 cadherin repeats (EC1˜EC5) in the extracellular domain, one transmembrane domain, and an intracellular domain that binds p120-catenin and β-catenin. The intracellular domain contains a highly-phosphorylated region that is believed to be vital to β-catenin binding and therefore to E-cadherin function. β-catenin may also bind to α-catenin, and α-catenin participates in regulation of actin-containing cytoskeletal filaments. In epithelial cells, E-cadherin-containing cell-to-cell junctions are often adjacent to actin-containing filaments of the cytoskeleton.

Other activities that may be affected due to the presence of the device in a local area include paracellular and transcellular transport. For instance, through adsorption of ECM proteins at the surface of the device, the local chemistry of an area can change, leading to improved paracellular transport of a delivered agent to the local area, which can include not only the immediate area of the device, but also areas deeper in the dermis. For instance, presence of the device can encourage paracellular transport of a delivered agent to the capillary beds of the dermis and across the capillary wall, so as to be delivered to the blood stream for systemic delivery.

During use, the device may interact with one or more components of the contacting epithelial tissue to increase porosity of the tissue via paracellular and/or transcellular transport mechanisms. Epithelial tissue is one of the primary tissue types of the body. Epithelial tissue as may be rendered more porous according to the present disclosure can include both simple and stratified epithelium, including both keratinized epithelium and transitional epithelium. In addition, epithelial tissue encompassed herein can include any cell types of an epithelial layer including, without limitation, keratinocytes, squamous cells, columnar cells, cuboidal cells and pseudostratified cells.

Presence of the device may affect formation and maintenance of cell/cell junctions including tight junctions and desmosomes to encourage paracellular transport. As previously mentioned, tight junctions have been found in the stratum granulosum and opening of the tight junctions may provide a paracellular route for improved delivery of active agents, particularly large molecular weight active agents and/or agents that exhibit low lipophilicity that have previously been blocked from transdermal delivery. The major types of proteins of tight junctions are claudins, occludins, and junctional adhesion molecules.

Interaction between a local component and structures of the nanotopography may open desmosomes in a barrier layer to encourage paracellular transport. Desmosomes are formed primarily of desmoglein and desmocollin, both members of the cadherins, and are involved in cell to cell adhesions. A desmosome includes an extracellular core domain (the desmoglea) where the desmoglein and the desmocollin proteins of adjacent cells bind one another. The adjacent cells are separated by a layer of ECM about 30 nanometers wide. Beneath the membrane, heavy plate-shaped structures are formed known as the outer dense plaque and the inner dense plaque. The plaques are spanned by the desmoplakin protein. The outer dense plaque is where the cytoplasmic domains of the cadherins attach to desmoplakin via plakoglobin and plakophillin. The inner dense plaque is where desmoplakin attaches to the intermediate filaments of the cell.

Interaction between individual cells and structures of the nanotopography may induce the passage of an agent through a barrier cell and encourage transcellular transport. For instance, interaction with keratinocytes of the stratum corneum can encourage the partitioning of an agent into the keratinocytes, followed by diffusion through the cells and across the lipid bilayer again. While an agent may cross a barrier according to both paracellular and transcellular routes, the transcellular route may be predominate for highly hydrophilic molecules, though, of course, the predominant transport path may vary depending upon the nature of the agent, hydrophilicity being only one defining characteristic.

According to one embodiment, the increased permeability of a cellular layer can be determined through determination of the transepithelial electrical resistance (TEER, also referred to herein as transepithelial resistance or TER) across the layer. As in generally known, a decrease in TEER across a cellular layer is a good indication of an increase in the permeability of a cell layer due to, for instance, the lack of formation or the opening of tight junctions of a cell layer. It is clear that in endothelia and certain epithelia, the ability of tight junctions to restrict paracellular flux is not immutable. Rather, this gate function of tight junctions is capable of dynamic regulation (Madara, 1988; Rubin, 1992). In particular, the activation of signal transduction pathways either by receptor ligands or specific membrane-permeant modulators can have striking effects on the permeability of the paracellular pathway. For example, protein kinase C activation causes a substantial increase in the permeability of tight junctions in MDCK cells (Ojakian, 1981), an epithelial cell line. Cyclic AMP elevation decreases permeability in brain endothelial cells in culture, a model system for the study of the blood-brain barrier (Rubin et al., 1991). Cyclic AMP also decreases tight junction permeability in peripheral endothelial cells (Stelzner et al., 1989; Langeier et al., 1991).

The permeability properties of the tight junction also depend upon the integrity of the adherens junction. Disruption of the adherens junction by removal of extracellular $Ca^{2+}$ leads to an opening of tight junctions in MDCK cells (see Martinez-Palomo et al., 1980; Gumbiner and Simons, 1986) and in endothelial cells (Rutten et al., 1987). Protein kinases appear to be involved in this indirect modulation of tight junctional integrity in MDCK cells (Citi, 1992). The $Ca^{2+}$-sensitive components of the adherens junction complex are the cadherins (reviewed by Geiger and Avalon, 1992). These transmembrane proteins mediate intercellular adhesiveness in a $Ca^{2+}$-dependent, homophilic manner via their extracellular domains. The cytoplasmic domain of the cadherins associates with three further proteins termed α-, β- and γ-catenin (Ozawa et al., 1989), which link the cadherins to the actin cytoskeleton and are required for cadherin adhesiveness (Hirano et al., 1987; Nagaruchi and Takeichi, 1988; Ozawa et al., 1990; Kintner, 1992; see Stappert and Kemler, 1993).

According to the present disclosure, contact between an epithelial layer and a device surface that includes a predetermined pattern of structures fabricated on the surface, at least a portion of which are fabricated on a nanometer scale, can increase the permeability and decrease the TEER of the epithelial layer. For instance, the TEER of an epithelial layer can drop to less than about 95%, less than about 85%, or less than about 70% of its initial value following contact between the layer and a nanopatterned surface for a period of time. By way of example, following about 30 minutes of contact between an epithelial layer and a surface including a pattern of nanostructures thereon, the TEER across the layer can be between about 90% and about 95% of its initial value. Following 60 minutes, the TEER across the layer can be between about 80% and about 90% of its initial value, and following 120 minutes, the TEER across the layer can be between about 60% and about 75% of its initial value.

Figure 10:
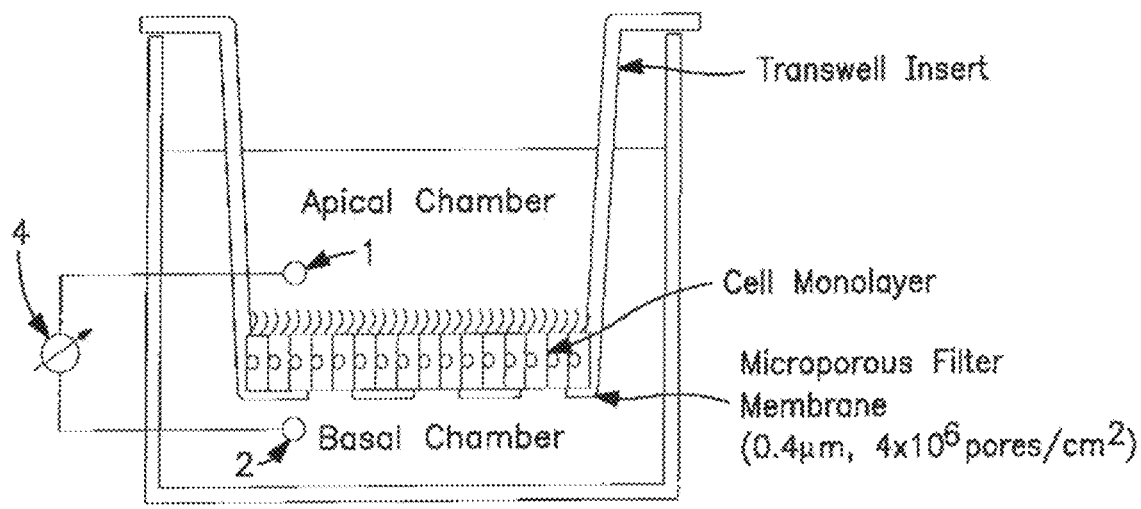
FIG. 10 illustrates a method for determining the TEER of a cellular layer.

FIG. 10 illustrates one method for determining the TEER across an epithelial layer. In this embodiment, a cell layer, for instance an epithelial cell monolayer, can be grown or otherwise located at the base of an apical chamber. The base of the apical chamber can be a microporous filter membrane, as shown, to allow flow between the two chambers and prevent individual cells from passing into the basal chamber. By way of example, the microporous filter membrane can include pores of about 0.4 micrometers at a density of about $4\times10^6$ pores/centimeter. Of course, the specific parameters of the various system components are not critical, and can be varied as is known in the art. The apical chamber can be defined by a transwell insert that can fit into a larger well, as shown, thereby defining the basal chamber of the system. During use a first electrode 1 and a second electrode 2 can be located on either side of the epithelial cell monolayer and an ohmmeter 4 can be connected between the two electrodes. The ohmmeter 4 can provide the TEER across the cell monolayer. Systems for determining the TEER across a cell layer are known, for instance, the Millicell™ electrical resistance system (available from Millipore of Bedford, Mass.) can be utilized.

Contact between an epithelial cell layer and a surface including nanostructures fabricated thereon can lead to a drop in TEER, which indicates an increase in layer permeability. Accordingly, following contact between an epithelial layer and a nanostructured surface, the ability to transport compounds across the layer can be greatly increased. This can improve transdermal delivery of compounds that previously could not be delivered efficiently in this fashion. For example, the transdermal delivery of high molecular weight compounds, lipophilic compounds and/or charged compounds can be improved through utilization of disclosed methods and devices.

Of course, nano-sized structures of the device may directly or indirectly affect other components of a surrounding microenvironment, and provided herein are only a representative sample of such structures.

The device including a fabricated nanotopography on a surface of the device may be formed according to a single-step process. Alternatively, a multi-step process may be used, in which a pattern of nanostructures are fabricated on a pre-formed surface. For example, an array of microneedles may be first formed and then a random or non-random pattern of nanostructures may be fabricated on the surface of the formed microneedles. In either the single-step or two-step process, structures may be fabricated on a surface or on a mold surface according to any suitable nanotopography fabrication method including, without limitation, nanoimprinting, injection molding, lithography, embossing molding, and so forth.

In general, an array of microneedles may be formed according to any standard microfabrication technique including, without limitation, lithography; etching techniques, such as wet chemical, dry, and photoresist removal; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, lamination, stereolithography, laser machining, and laser ablation (including projection ablation).

An electrochemical etching process may be utilized in which electrochemical etching of solid silicon to porous silicon is used to create extremely fine (on the order of 0.01 μm) silicon networks that may be used as piercing structures. This method may use electrolytic anodization of silicon in aqueous hydrofluoric acid, potentially in combination with light, to etch channels into the silicon. By varying the doping concentration of the silicon wafer to be etched, the electrolytic potential during etching, the incident light intensity, and the electrolyte concentration, control over the ultimate pore structure may be achieved. The material not etched (i.e. the silicon remaining) forms the microneedles.

Plasma etching may also be utilized, in which deep plasma etching of silicon is carried out to create microneedles with diameters on the order of 0.1 micrometer or larger. Needles may be fabricated indirectly by controlling the voltage (as in electrochemical etching).

Lithography techniques, including photolithography, e-beam lithography, X-ray lithography, and so forth may be utilized for primary pattern definition and formation of a master die. Replication may then be carried out to form the device including an array of microneedles. Common replication methods include, without limitation, solvent-assisted micromolding and casting, embossing molding, injection molding, and so forth. Self-assembly technologies including phase-separated block copolymer, polymer demixing and colloidal lithography techniques may also be utilized in forming a nanotopography on a surface.

Combinations of methods may be used, as is known. For instance, substrates patterned with colloids may be exposed to reactive ion etching (RIE, also known as dry etching) so as to refine the characteristics of a fabricated nanostructure such as nanopillar diameter, profile, height, pitch, and so forth. Wet etching may also be employed to produce alternative profiles for fabricated nanostructures initially formed according to a different process, e.g., polymer de-mixing techniques.

Structure diameter, shape, and pitch may be controlled via selection of appropriate materials and methods. For example, etching of metals initially evaporated onto colloidal-patterned substrates followed by colloidal lift-off generally results in prism-shaped pillars. An etching process may then be utilized to complete the structures as desired. Ordered non-spherical polymeric nanostructures may also be fabricated via temperature-controlled sintering techniques, which form a variety of ordered trigonal nanometric features in colloidal interstices following selective dissolution of polymeric nanoparticles. These and other suitable formation processes are generally known in the art (see, e.g., Wood, J R Soc interface, 2007 Feb. 22; 4(12): 1-17, incorporated herein by reference).

Figure 11A:
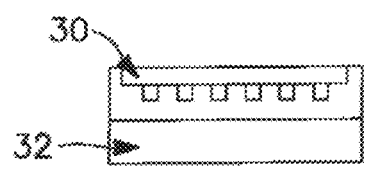
FIGS. 11A-11C schematically illustrate a nanoimprinting method as may be utilized in one embodiment in forming a device.
Figure 11B:
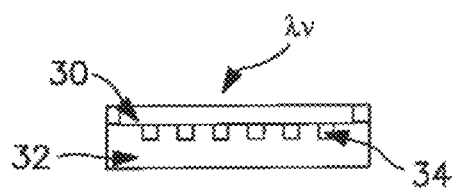
Figure 11C:
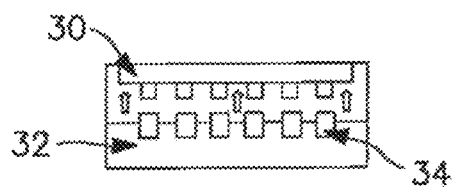

Other methods as may be utilized in forming a microneedle including a fabricated nanotopography on a surface include nanoimprint lithography methods utilizing ultra-high precision laser machining techniques, examples of which have been described by Hunt, et al. (U.S. Pat. No. 6,995,336) and Guo, et al. (U.S. Pat. No. 7,374,864), both of which are incorporated herein by reference. Nanoimprint lithography is a nano-scale lithography technique in which a hybrid mold is utilized which acts as both a nanoimprint lithography mold and a photolithography mask. A schematic of a nanoimprint lithography technique is illustrated in FIGS. 11A-11C. During fabrication, a hybrid mold 30 imprints into a substrate 32 via applied pressure to form features (e.g., microneedles defining nanotopography) on a resist layer (FIG. 11A). In general, the surface of the substrate 32 may be heated prior to engagement with the mold 30 to a temperature above its glass transition temperature ($T_g$). While the hybrid mold 30 is engaged with the substrate 32, a flow of viscous polymer may be forced into the mold cavities to form features 34 (FIG. 11B). The mold and substrate may then be exposed to ultraviolet light. The hybrid mold is generally transmissive to UV radiation save for certain obstructed areas. Thus, the UV radiation passes through transmissive portions and into the resist layer. Pressure is maintained during cooling of the mold and substrate. The hybrid mold 30 is then removed from the cooled substrate 32 at a temperature below $T_9$ of the substrate and polymer (FIG. 11C).

To facilitate the release of the nanoimprinted substrate 32 including fabricated features 34 from the mold 30, as depicted in FIG. 11C, it is advantageous to treat the mold 30 with a low energy coating to reduce the adhesion with the substrate 32, as a lower surface energy of the mold 30 and the resulting greater surface energy difference between the mold 30, substrate 32, and polymer may ease the release between the materials. By way of example, a silicon mold coating may be used such as trideca-(1,1,2,2-tetrahydro)-octytrichloro silane ($F_{13}$-TCS).

A nanoimprinting process is a dynamic one which includes filling a mold followed by detachment of a formed polymer from the mold. To fill the mold features, the polymer temperature must be raised to a level high enough to initiate flow under the applied pressure. The higher the temperature, the lower the polymer viscosity, and the faster and easier the mold will fill. A higher pressure will also improve the fill rate and overall fill for better mold replication. To release the nanoimprinted substrate from the mold, the substrate temperature may be lowered to a point where the yield strength exceeds the adhesional forces exerted by the mold. By varying the temperature it is also possible to draw the polymer features during detachment to obtain different structures, for instance structures as illustrated in FIG. 8.

Structures may also be formed according to chemical addition processes. For instance, film deposition, sputtering, chemical vapor deposition (CVD), epitaxy (vapor phase, liquid phase, and molecular beam), electroplating, and so forth can be utilized for building structures on a surface.

Self-assembled monolayer processes as are known in the art can be utilized to form a pattern of structures on a surface. For instance, the ability of block copolymers to self-organize can be used to form a monolayer pattern on a surface. The pattern can then be used as a template for the growth of desired structures, e.g., colloids, according to the pattern of the monolayer.

By way of example, a two-dimensional, cross-linked polymer network can be produced from monomers with two or more reactive sites. Such cross-linked monolayers have been made using self-assembling monolayer (SAM) (e.g., a gold/alkyl thiol system) or Langmuir-Blodgett (LB) monolayer techniques (Ahmed et al., Thin Solid Films 187: 141-153 (1990)) as are known in the art. The monolayer can be crosslinked, which can lead to formation of a more structurally robust monolayer.

The monomers used to form a patterned monolayer can incorporate all the structural moieties necessary to affect the desired polymerization technique and/or monolayer formation technique, as well as to influence such properties as overall solubility, dissociation methods, and lithographic methods. A monomer can contain at least one, and more often at least two, reactive functional groups.

A molecule used to form an organic monolayer can include any of various organic functional groups interspersed with chains of methylene groups. For instance a molecule can be a long chain carbon structure containing methylene chains to facilitate packing. The packing between methylene groups can allow weak Van der Waals bonding to occur, enhancing the stability of the monolayer produced and counteracting the entropic penalties associated with forming an ordered phase. In addition, different terminal moieties, such as hydrogen-bonding moieties may be present at one terminus of the molecules, in order to allow growth of structures on the formed monolayer, in which case the polymerizable chemical moieties can be placed in the middle of the chain or at the opposite terminus. Any suitable molecular recognition chemistry can be used in forming the assembly. For instance, structures can be assembled on a monolayer based on electrostatic interaction, Van der Waals interaction, metal chelation, coordination bonding (i.e., Lewis acid/base interactions), ionic bonding, covalent bonding, or hydrogen bonding.

When utilizing a SAM-based system, an additional molecule can be utilized to form the template. This additional molecule can have appropriate functionality at one of its termini in order to form a SAM. For example, on a gold surface, a terminal thiol can be included. There are a wide variety of organic molecules that may be employed to effect replication. Topochemically polymerizable moieties, such as dienes and diacetylenes, are particularly desirable as the polymerizing components. These can be interspersed with variable lengths of methylene linkers.

For an LB monolayer, only one monomer molecule is needed because the molecular recognition moiety can also serve as the polar functional group for LB formation purposes. Lithography can be carried out on a LB monolayer transferred to a substrate, or directly in the trough. For example, an LB monolayer of diacetylene monomers can be patterned by UV exposure through a mask or by electron beam patterning.

Monolayer formation can be facilitated by utilizing molecules that undergo a topochemical polymerization in the monolayer phase. By exposing the assembling film to a polymerization catalyst, the film can be grown in situ, and changed from a dynamic molecular assembly to a more robust polymerized assembly.

Any of the techniques known in the art for monolayer patterning may be used for patterning of the monolayer. Techniques useful in patterning a monolayer include, but are not limited to, photolithography, e-beam techniques, focused ion-beam techniques, and soft lithography. Various protection schemes such as photoresist can be used for a SAM-based system. Likewise, block copolymer patterns can be formed on gold and selectively etched to form patterns. For a two-component system, patterning can also be achieved with readily available techniques.

Soft lithography techniques can be utilized to pattern the monolayer in which ultraviolet light and a mask can be used for patterning. For instance, an unpatterned base monolayer may be used as a platform for assembly of a UV/particle beam reactive monomer monolayer. The monomer monolayer may then be patterned by UV photolithography, e-beam lithography, or ion beam lithography, even though the base SAM is not patterned.

Growth of structures on a patterned monolayer can be achieved by various growth mechanisms, such as through appropriate reduction chemistry of a metal salts and the use of seed or template-mediated nucleation. Using the recognition elements on the monolayer, inorganic growth can be catalyzed at this interface by a variety of methods. For instance inorganic compounds in the form of colloids bearing the shape of the patterned organic monolayer can be formed. For instance calcium carbonate or silica structures can be templated by various carbonyl functionalities such as carboxylic acids and amides. By controlling the crystal growth conditions, it is possible to control the thickness and crystal morphology of the mineral growth. Titanium dioxide can also be templated.

Templated electroless plating techniques can be used to synthesize metals using existing organic functional groups. In particular, by chelating metal atoms to the carbonyl moieties of the organic pattern, electroless metal deposition can be catalyzed on the pattern, forming patterned metallic colloids. For instance, Cu, Au, Ni, Ag, Pd, Pt and many other metals plateable by electroless plating conditions may be used to form metal structures in the shape of the organic monolayer. By controlling the electroless plating conditions, it is possible to control the thickness of the plated metal structures.

Other 'bottom-up' type growth methods as are known in the art can be utilized, for example a method as described in U.S. Pat. No. 7,189,435 Tuominen, et al., which is incorporated herein by reference, can be utilized. According to this method, a conducting or semiconducting substrate (for example, a metal, such as gold) can be coated with a block copolymer film (for example, a block copolymer of methylmethacrylate and styrene), where one component of the copolymer forms nanoscopic cylinders in a matrix of another component of the copolymer. A conducting layer can then be placed on top of the copolymer to form a composite structure. Upon vertically orientation of the composite structure, some of the first component can be removed, for instance by exposure to UV radiation, an electron beam, or ozone, degradation, or the like to form nanoscopic pores in that region of the second component.

In another embodiment, described in U.S. Pat. No. 6,926,953 to Nealey, et al., incorporated herein by reference, copolymer structures can be formed by exposing a substrate with an imaging layer thereon, for instance an alkylsiloxane or an octadecyltrichlorosilane self assembled monolayer, to two or more beams of selected wavelengths to form interference patterns at the imaging layer to change the wettability of the imaging layer in accordance with the interference patterns. A layer of a selected block copolymer, for instance a copolymer of polystyrene and poly(methyl methacrylate) can then be deposited onto the exposed imaging layer and annealed to separate the components of the copolymer in accordance with the pattern of wettability and to replicate the pattern of the imaging layer in the copolymer layer. Stripes or isolated regions of the separated components may thus be formed with periodic dimensions in the range of 100 nanometers or less.

The device surface can include a random distribution of fabricated nanostructures. Optionally, the surface can include additional materials, in conjunction with the fabricated nanostructures. For example, a microneedle surface may have fabricated thereon an electrospun fibrous layer, and a random or non-random pattern of structures may be fabricated on this electrospun layer.

Electrospinning includes of the use of a high voltage supplier to apply an electrical field to a polymer melt or solution held in a capillary tube, inducing a charge on the individual polymer molecules. Upon application of the electric field, a charge and/or dipolar orientation will be induced at the air-surface interface. The induction causes a force that opposes the surface tension. At critical field strength, the electrostatic forces will overcome surface tension forces, and a jet of polymer material will be ejected from the capillary tube toward a conductive, grounded surface. The jet is elongated and accelerated by the external electric field as it leaves the capillary tube. As the jet travels in air, some of the solvent may evaporate, leaving behind charged polymer fibers which may be collected on the surface. As the fibers are collected, the individual and still wet fibers may adhere to one another, forming a nonwoven web on the surface. A pattern of nanostructures may then be fabricated on the electrospun surface, for instance through an embossing technique utilizing a mold defining the desired nanostructures. Applying the mold to the microneedle surface at suitable temperature and pressure can transfer the pattern to the microneedle surface. A surface of random electrospun nano-sized fibers may further improve the desirable characteristics of a microneedle surface, e.g., one or more of surface area to volume ratio, surface roughness, surface energy, and so forth, and may provide associated benefits.

The surface of a microneedle surface can be further functionalized for improved interaction with tissues or individual cells during use. For instance, one or more biomolecules such as polynucleotides, polypeptides, entire proteins, polysaccharides, and the like can be bound to a structured surface prior to use.

In some embodiments, a surface including structures formed thereon can already contain suitable reactivity such that additional desired functionality may spontaneously attach to the surface with no pretreatment of the surface necessary. However, in other embodiments, pretreatment of the structured surface prior to attachment of the desired compound may be carried out. For instance, reactivity of a structure surface may be increased through addition or creation of amine, carboxylic acid, hydroxy, aldehyde, thiol, or ester groups on the surface. In one representative embodiment, a microneedle surface including a pattern of nanostructures formed thereon may be aminated through contact with an amine-containing compound such as 3-aminopropyltriethoxy silane in order to increase the amine functionality of the surface and bind one or more biomolecules to the surface via the added amine functionality.

Materials as may be desirably bound to the surface of a patterned device can include ECM proteins such as laminins, tropoelastin or elastin, Tropocollagen or collagen, fibronectin, and the like. Short polypeptide fragments can be bound to the surface of a patterned device such as an RGD sequence, which is part of the recognition sequence of integrin binding to many ECM proteins. Thus, functionalization of a microneedle surface with RGD can encourage interaction of the device with ECM proteins and further limit foreign body response to the device during use.

Devices may be associated with an agent for delivery via the device. For instance, a transdermal microneedle patch may be utilized for delivery of materials beneath the stratum corneum to the stratum spinosum or the stratum germinativum, or even deeper into the dermis. In general, an agent may be transported across the stratum corneum in conjunction with the microneedle, e.g., within the microneedle or at the surface of the microneedle.

The device may include a reservoir, e.g., a vessel, a porous matrix, etc., that may store and agent and provide the agent for delivery. The device may include a reservoir within the device itself. For instance, the device may include a hollow, or multiple pores that may carry one or more agents for delivery. The agent may be released from the device via degradation of a portion or the entire device or via diffusion of the agent from the device.

Figure 12A:
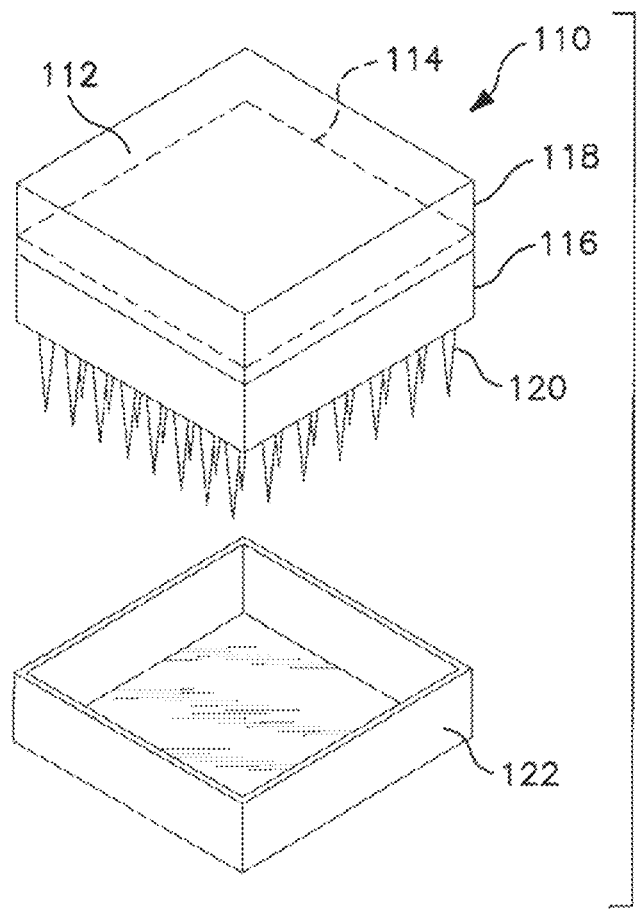
Figure 12B:
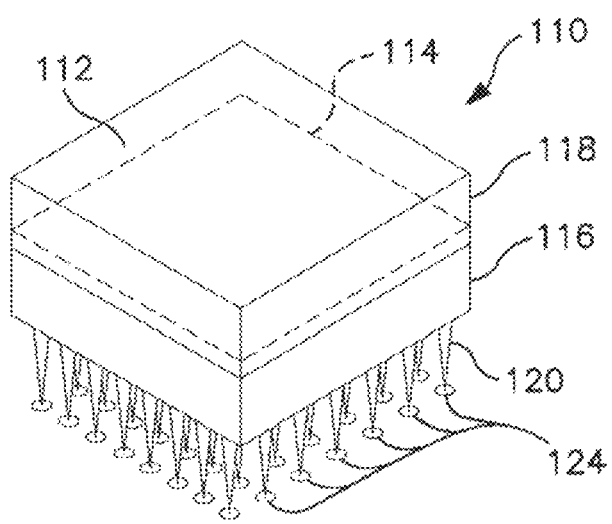

FIGS. 12A and 12B are perspective views of the device including a reservoir. The device 110 includes a reservoir 112 defined by an impermeable backing layer 114 and a microneedle array 116. The backing layer and the microneedle array 116 are joined together about the outer periphery of the device, as indicated at 118. The impermeable backing layer 114 may be joined by an adhesive, a heat seal or the like. The device 110 also includes a plurality of microneedles 120. A release liner 122 can be removed prior to use of the device to expose microneedles 120.

A formulation including one or more agents may be retained within the reservoir 112. Materials suitable for use as impermeable backing layer 114 can include materials such as polyesters, polyethylene, polypropylene and other synthetic polymers. The material is generally heat or otherwise sealable to the backing layer to provide a barrier to transverse flow of reservoir contents.

Reservoir 112, defined by the space or gap between the impermeable backing layer 114 and the microneedle array 116, provides a storage structure in which to retain the suspension of agents to be administered. The reservoir may be formed from a variety of materials that are compatible with an agent to be contained therein. By way of example, natural and synthetic polymers, metals, ceramics, semiconductor materials, and composites thereof may form the reservoir.

In one embodiment, the reservoir may be attached to the substrate upon which the microneedles are located. According to another embodiment, the reservoir may be separate and removably connectable to the microneedle array or in fluid communication with the microneedle array, for instance via appropriate tubing, luer locks, etc.

The device may include one or a plurality of reservoirs for storing agents to be delivered. For instance, the device may include a single reservoir that stores a single or multiple agent-containing formulation, or the device may include multiple reservoirs, each of which stores one or more agents for delivery to all or a portion of the array of microneedles. Multiple reservoirs may each store a different material that may be combined for delivery. For instance, a first reservoir may contain an agent, e.g., a drug, and a second reservoir may contain a vehicle, e.g., saline. The different agents may be mixed prior to delivery. Mixing may be triggered by any means, including, for example, mechanical disruption (i.e. puncturing, degradation, or breaking), changing the porosity, or electrochemical degradation of the walls or membranes separating the chambers. Multiple reservoirs may contain different active agents for delivery that may be delivered in conjunction with one another or sequentially.

In one embodiment, the reservoir may be in fluid communication with one or more microneedles of the transdermal device, and the microneedles may define a structure (e.g., a central or lateral bore) to allow transport of delivered agents beneath the barrier layer.

Figure 13:
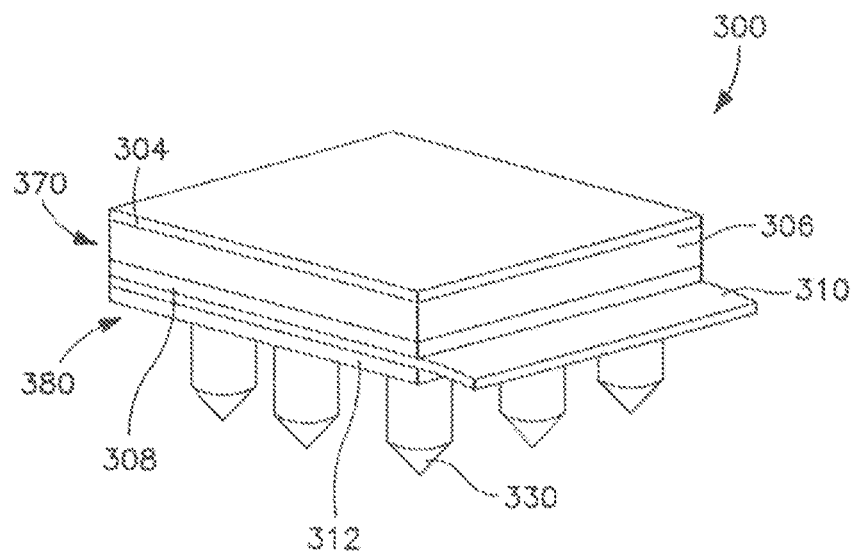
FIG. 13 is a perspective view of one embodiment of a transdermal patch prior to delivery of a drug compound.
Figure 14:
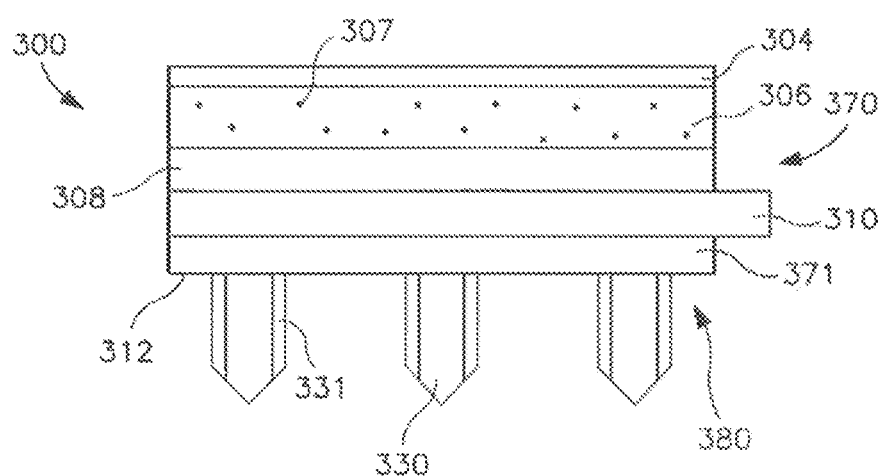
FIG. 14 is a front view of the patch of FIG. 13.

In alternative embodiments, a device may include a microneedle assembly and a reservoir assembly with flow prevention between the two prior to use. For instance, a device may include a release member positioned adjacent to both a reservoir and a microneedle array. The release member may be separated from the device prior to use such that during use the reservoir and the microneedle array are in fluid communication with one another. Separation may be accomplished through the partial or complete detachment of the release member. For example, referring to FIGS. 13-18, one embodiment of a release member is shown that is configured to be detached from a transdermal patch to initiate the flow of a drug compound. More particularly, FIGS. 13-14 show a transdermal patch 300 that contains a drug delivery assembly 370 and a microneedle assembly 380. The drug delivery assembly 370 includes a reservoir 306 positioned adjacent to a rate control membrane 308.

The rate control membrane may help slow down the flow rate of the drug compound upon its release. Specifically, fluidic drug compounds passing from the drug reservoir to the microneedle assembly via microfluidic channels may experience a drop in pressure that results in a reduction in flow rate. If this difference is too great, some backpressure may be created that may impede the flow of the compound and potentially overcome the capillary pressure of the fluid through the microfluidic channels. Thus, the use of the rate control membrane may ameliorate this difference in pressure and allow the drug compound to be introduced into the microneedle at a more controlled flow rate. The particular materials, thickness, etc. of the rate control membrane may vary based on multiple factors, such as the viscosity of the drug compound, the desired delivery time, etc.

The rate control membrane may be fabricated from permeable, semi-permeable or microporous materials that are known in the art to control the rate of drug compounds and having permeability to the permeation enhancer lower than that of drug reservoir. For example, the material used to form the rate control membrane may have an average pore size of from about 50 nanometers to about 5 micrometers, in some embodiments from about 100 nanometers to about 2 micrometers, and in some embodiments, from about 300 nanometers to about 1 micrometer (e.g., about 600 nanometers). Suitable membrane materials include, for instance, fibrous webs (e.g., woven or nonwoven), apertured films, foams, sponges, etc., which are formed from polymers such as polyethylene, polypropylene, polyvinyl acetate, ethylene n-butyl acetate and ethylene vinyl acetate copolymers. Such membrane materials are also described in more detail in U.S. Pat. Nos. 3,797,494, 4,031,894, 4,201,211, 4,379,454, 4,436,741, 4,588,580, 4,615,699, 4,661,105, 4,681,584, 4,698,062, 4,725,272, 4,832,953, 4,908,027, 5,004,610, 5,310,559, 5,342,623, 5,344,656, 5,364,630, and 6,375,978, which are incorporated in their entirety herein by reference for all relevant purposes. A particularly suitable membrane material is available from Lohmann Therapie-Systeme.

Referring to FIGS. 13-14, although optional, the assembly 370 also contains an adhesive layer 304 that is positioned adjacent to the reservoir 306. The microneedle assembly 380 likewise includes a support 312 from which extends a plurality of microneedles 330 having channels 331, such as described above. The layers of the drug delivery assembly 370 and/or the microneedle assembly 380 may be attached together if desired using any known bonding technique, such as through adhesive bonding, thermal bonding, ultrasonic bonding, etc.

Regardless of the particular configuration employed, the patch 300 also contains a release member 310 that is positioned between the drug delivery assembly 370 and the microneedle assembly 380. While the release member 310 may optionally be bonded to the adjacent support 312 and/or rate control membrane 308, it is typically desired that it is only lightly bonded, if at all, so that the release member 310 may be easily withdrawn from the patch 300. If desired, the release member 310 may also contain a tab portion 371 (FIGS. 13-14) that extends at least partly beyond the perimeter of the patch 300 to facilitate the ability of a user to grab onto the member and pull it in the desired direction. In its "inactive" configuration as shown in FIGS. 13-14, the drug delivery assembly 370 of the patch 300 securely retains a drug compound 307 so that it does not flow to any significant extent into the microneedles 330. The patch may be "activated" by simply applying a force to the release member so that it is detached from the patch.

Figure 15:
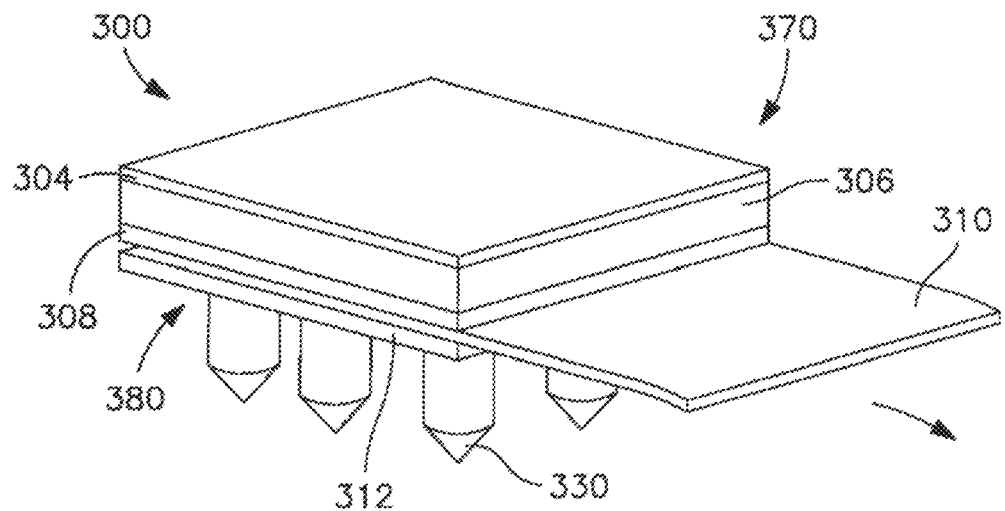
FIG. 15 is a perspective view of the patch of FIG. 13 in which the release member is partially withdrawn from the patch.
Figure 16:
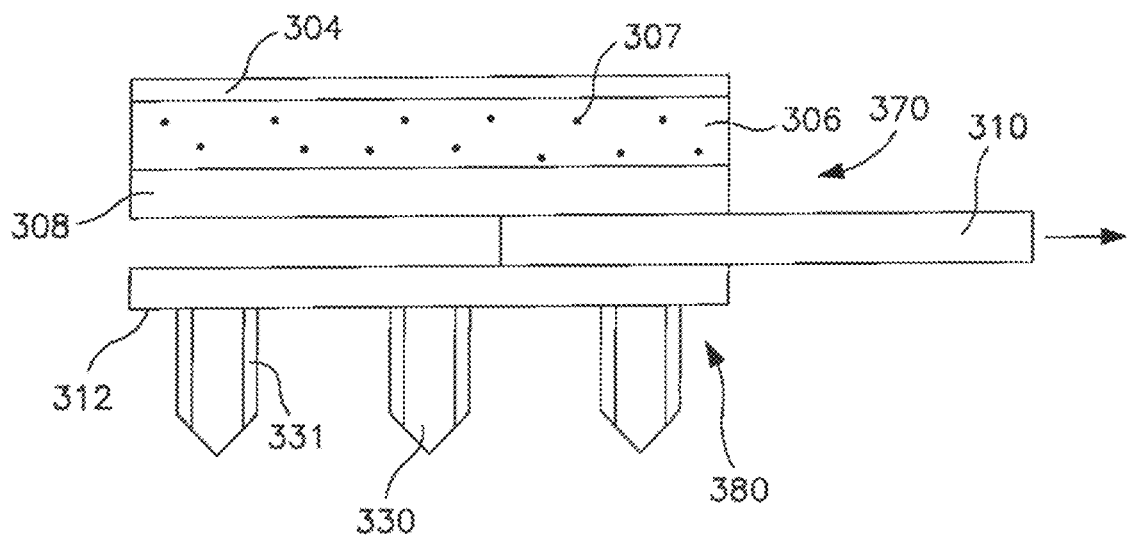
FIG. 16 is a front view of the patch of FIG. 13.
Figure 17:
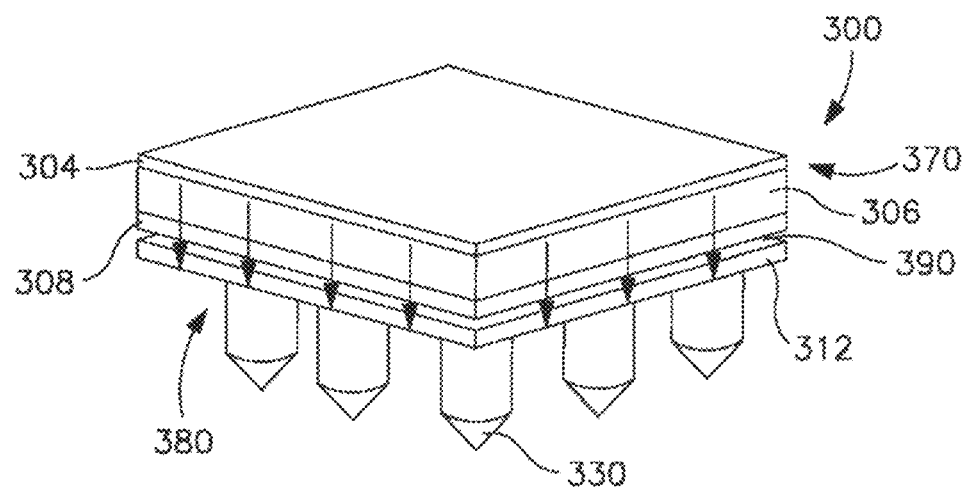
FIG. 17 is a perspective view of the transdermal patch of FIG. 13 after removal of the release member and during use.
Figure 18:
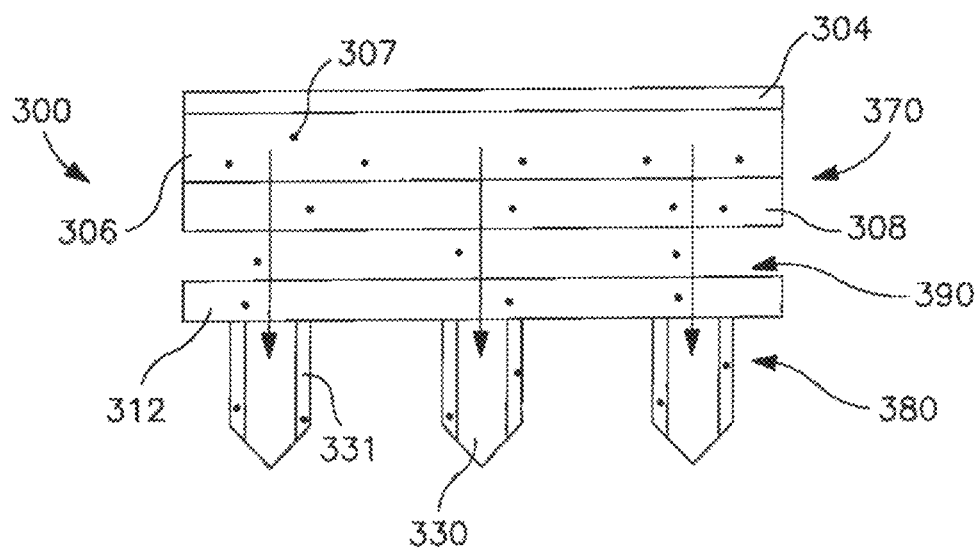
FIG. 18 is a front view of the patch of FIG. 17.

Referring to FIGS. 15-16, one embodiment for activating the patch 300 is shown in which the release member 310 is pulled in a longitudinal direction. The entire release member 310 may be removed as shown in FIGS. 17-18, or it may simply be partially detached as shown in FIGS. 15-16. In either case, however, the seal previously formed between the release member 310 and the aperture (not shown) of the support 312 is broken. In this manner, a drug compound 307 may begin to flow from the drug delivery assembly 370 and into the channels 331 of the microneedles 330 via the support 312. An exemplary illustration of how the drug compound 307 flows from the reservoir 306 and into the channels 331 is shown in FIGS. 17-18. Notably, the flow of the drug compound 307 is passively initiated and does not require any active displacement mechanisms (e.g., pumps).

In the embodiments shown in FIGS. 13-18, the detachment of the release member immediately initiates the flow of the drug compound to the microneedles because the drug delivery assembly is already disposed in fluid communication with the microneedle assembly. In certain embodiments, however, it may be desired to provide the user with a greater degree of control over the timing of the release of the drug compound. This may be accomplished by using a patch configuration in which the microneedle assembly is not initially in fluid communication with the drug delivery assembly. When it is desired to use the patch, the user may physically manipulate the two separate assemblies into fluid communication. The release member may be separated either before or after such physical manipulation occurs.

Figure 19:
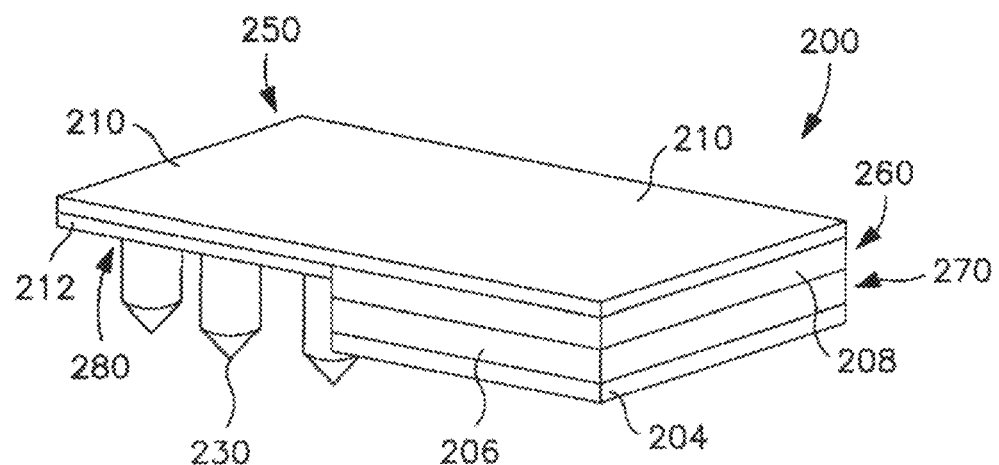
FIG. 19 is a perspective view of another embodiment of a transdermal patch prior to delivery of a drug compound.
Figure 20:
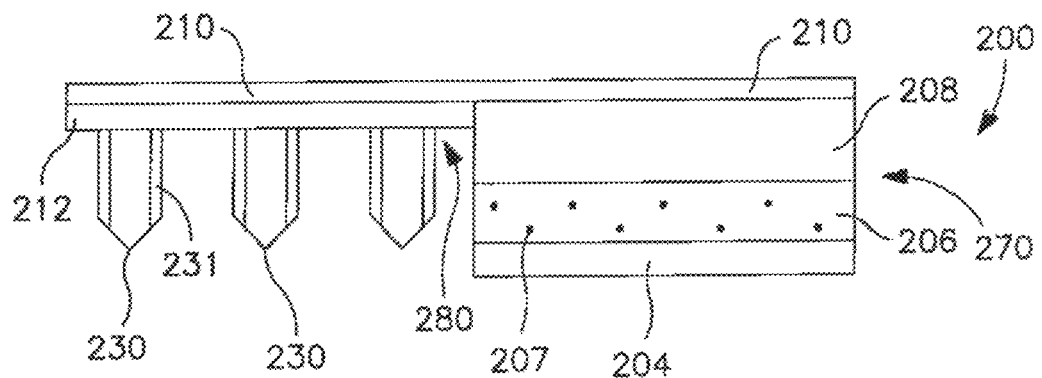
FIG. 20 is a front view of the patch of FIG. 19.

Referring to FIGS. 19-24, for example, one particular embodiment of a patch 200 is shown. FIGS. 19-20 illustrate the patch 200 before use, and shows a first section 250 formed by a microneedle assembly 280 and a second section 260 formed by a drug delivery assembly 270. The drug delivery assembly 270 includes a reservoir 206 positioned adjacent to a rate control membrane 208 as described above. Although optional, the assembly 270 also contains an adhesive layer 204 that is positioned adjacent to the reservoir 206. The microneedle assembly 280 likewise includes a support 212 from which extends a plurality of microneedles 230 having channels 231, such as described above.

Figure 21:
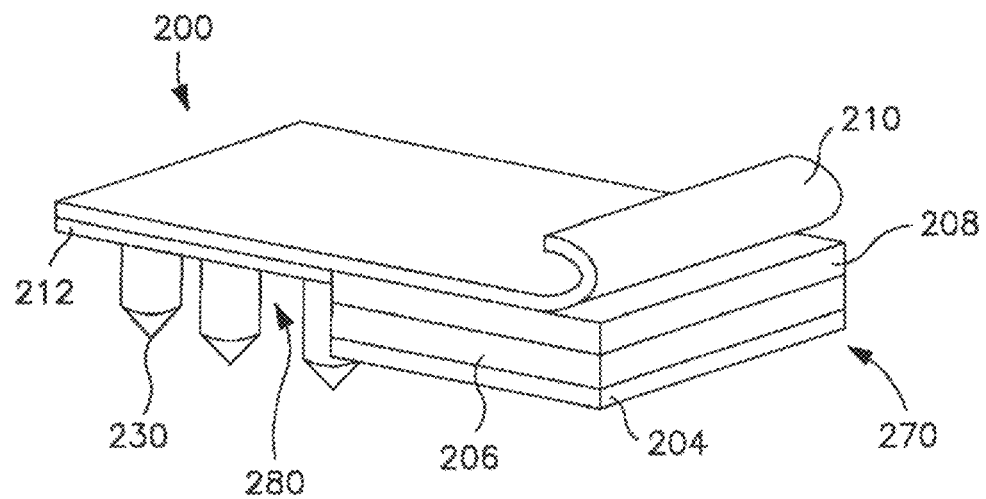
FIG. 21 is a perspective view of the patch of FIG. 19 in which the release member is partially peeled away from the patch.
Figure 22:
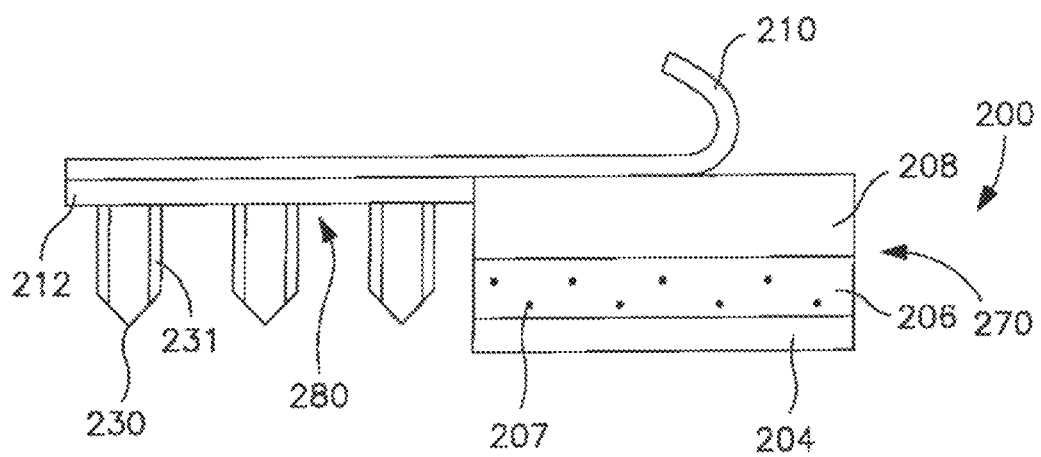
FIG. 22 is a front view of the patch of FIG. 21.
Figure 23:
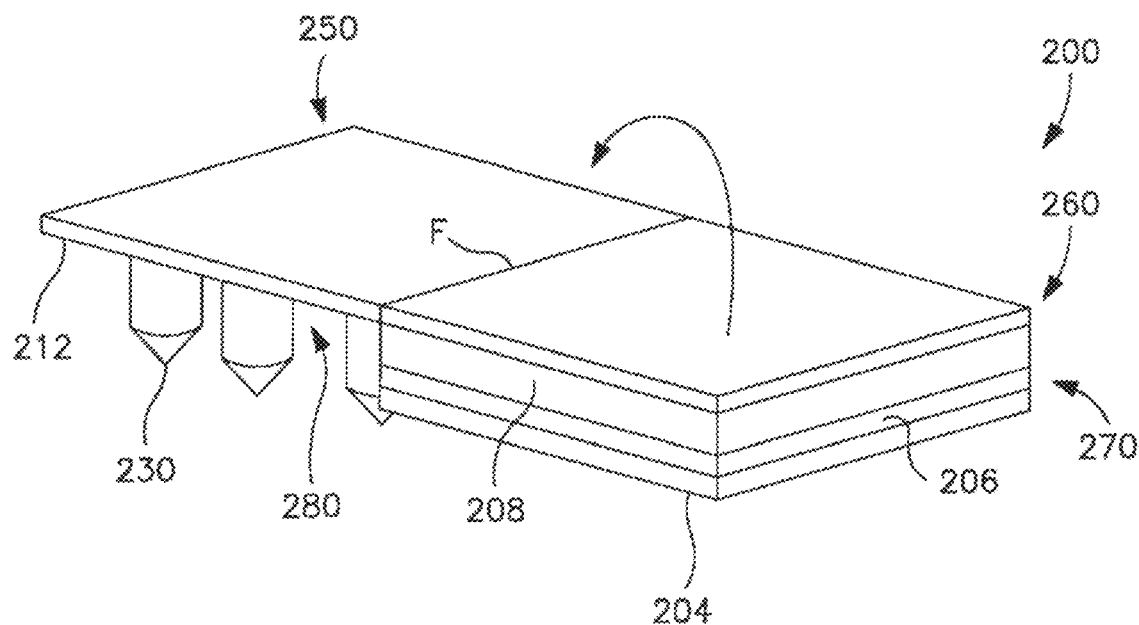
FIG. 23 is a perspective view of the patch of FIG. 19 in which the release member is completely peeled away from the patch.
Figure 24:
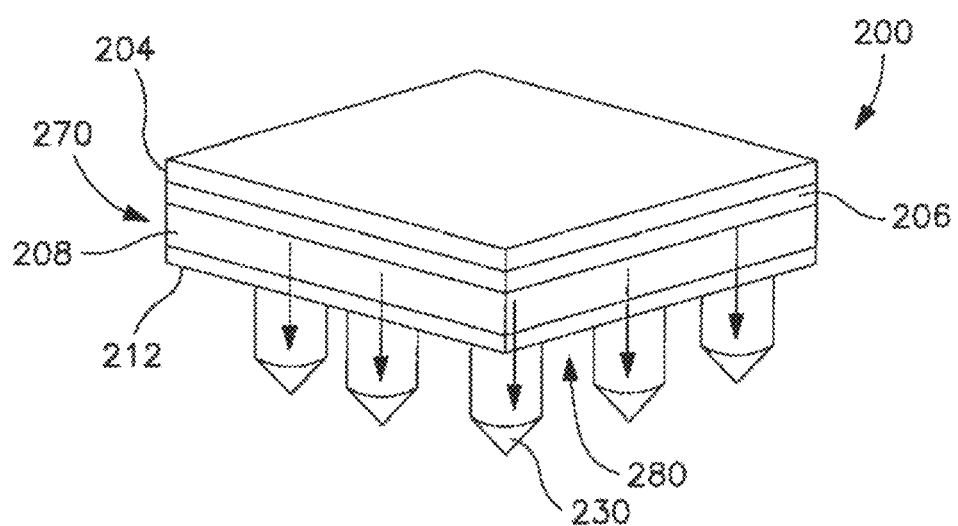
FIG. 24 is a perspective view of the transdermal patch of FIG. 19 after removal of the release member and during use.
Figure 27A:
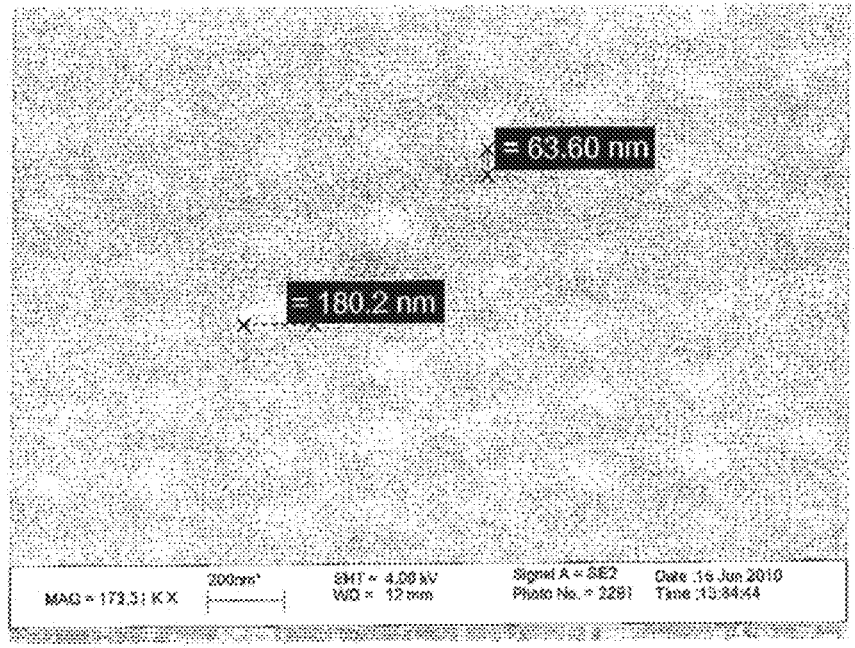
FIGS. 27A and 27B are two SEM of a film including another nanopatterned surface.
Figure 27B:
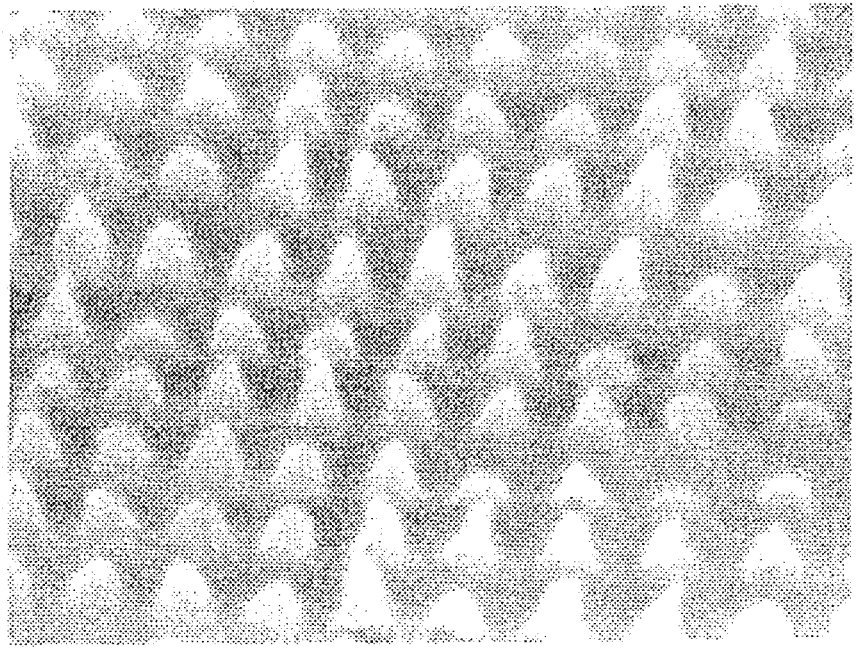
Figure 28:
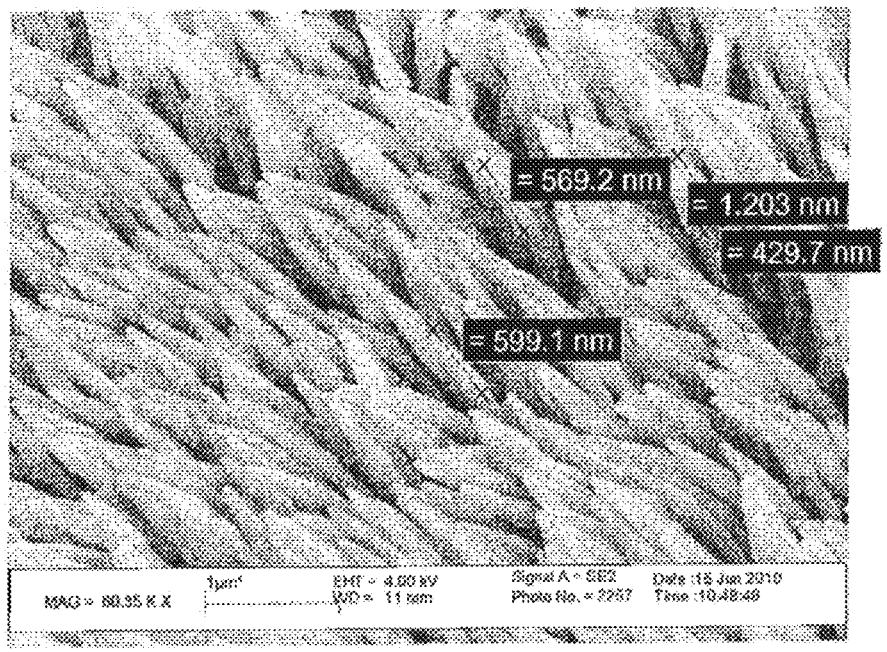
FIG. 28 is an SEM of a film including another nanopatterned surface.
Figure 29:
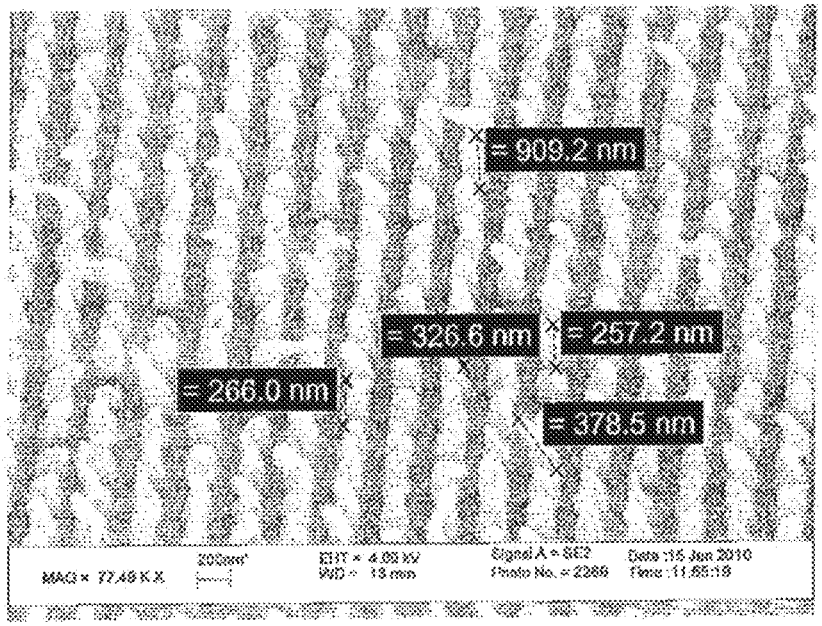
FIG. 29 is an SEM of a film including another nanopatterned surface.
Figure 30:
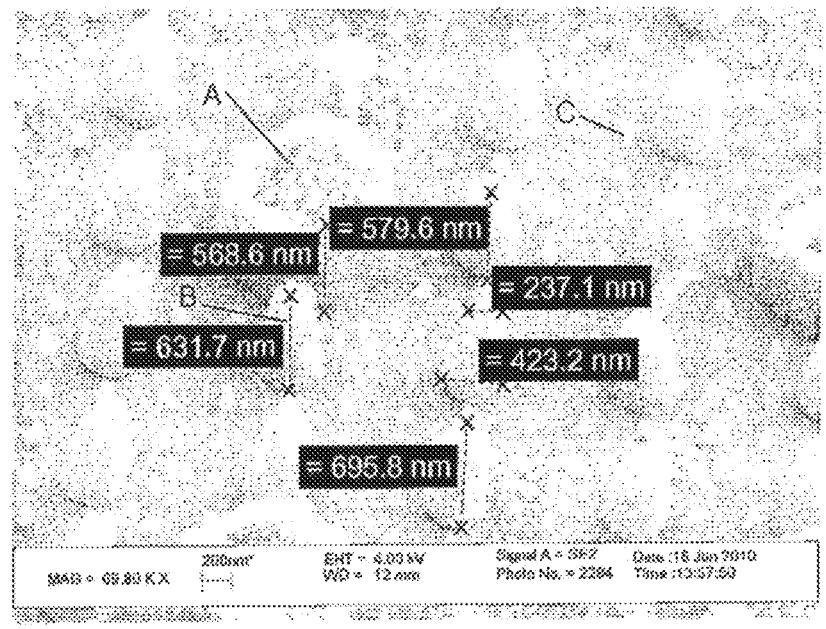
FIG. 30 is an SEM of a film including another nanopatterned surface.
Figure 31:
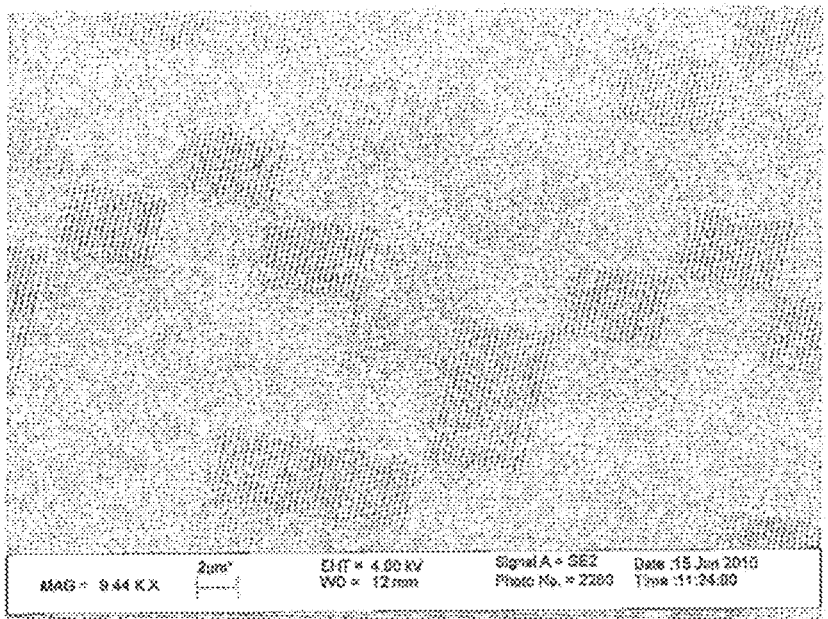
FIG. 31 is an SEM of a film including another nanopatterned surface.
Figure 32:
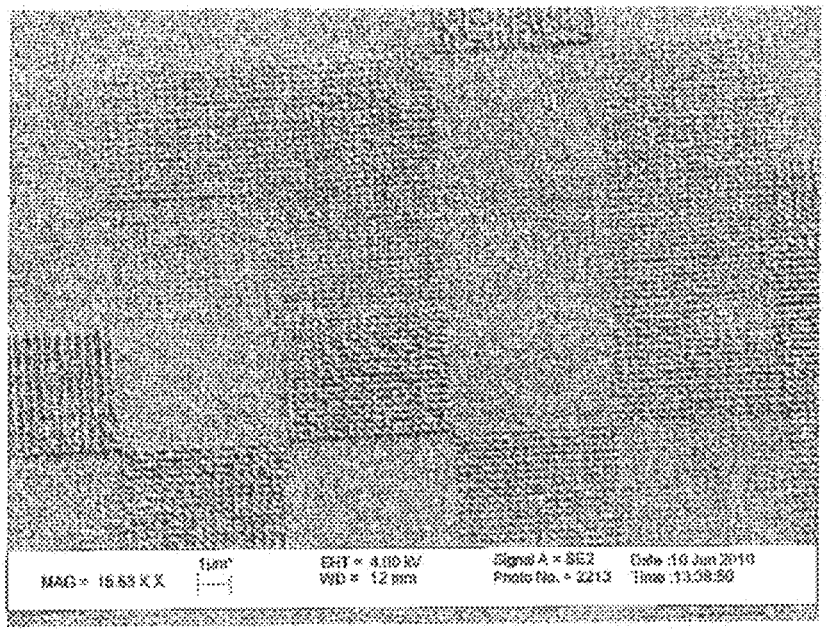
FIG. 32 is an SEM of a film including another nanopatterned surface.
Figure 33:
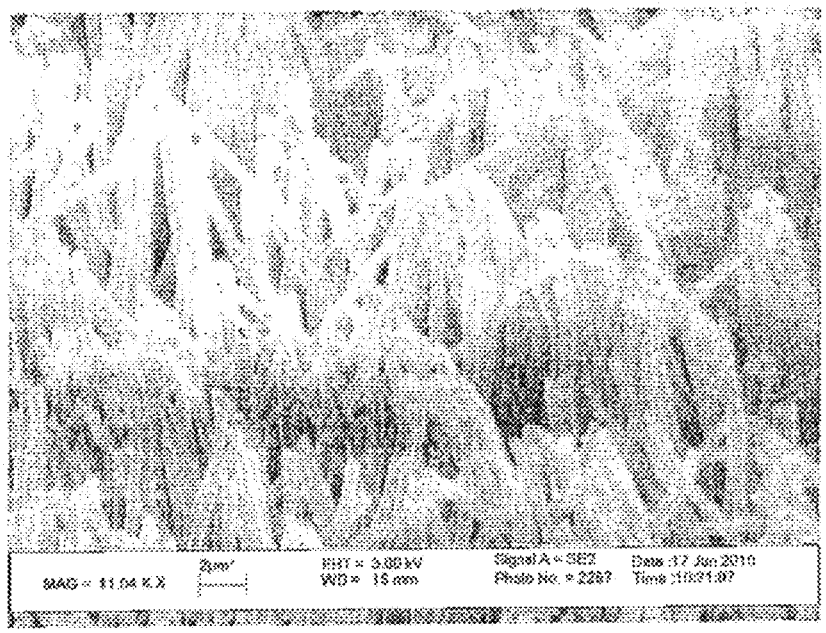
FIG. 33 is an SEM of a film including another nanopatterned surface.
Figure 34:
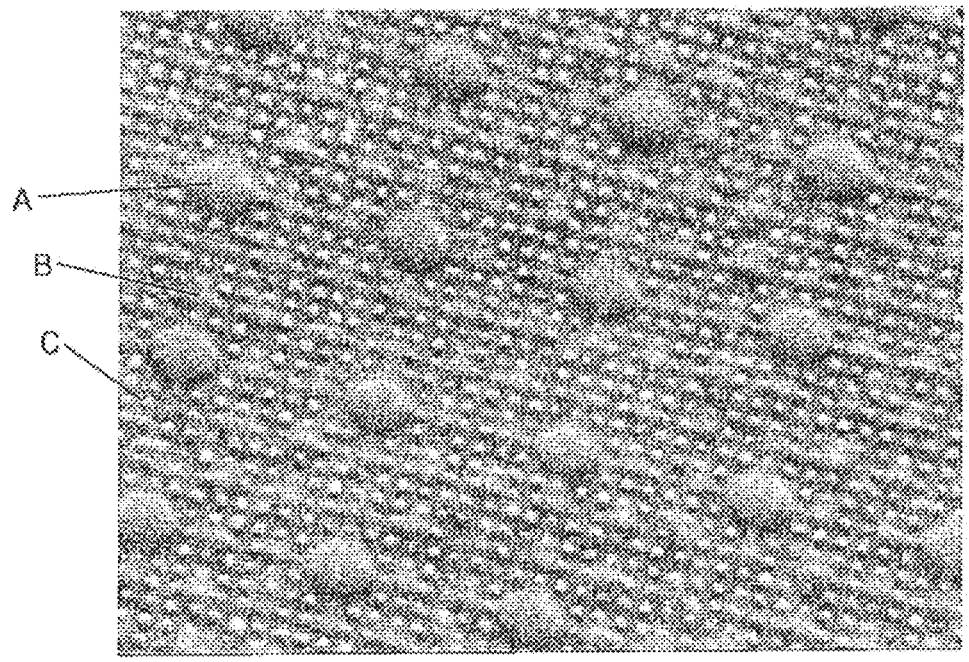
FIG. 34 is an SEM of a film including another nanopatterned surface.

In this embodiment, the support 212 and the rate control membrane 208 are initially positioned horizontally adjacent to each other, and a release member 210 extends over the support 212 and the rate control membrane 208. In this particular embodiment, it is generally desired that the release member 210 is releasably attached to the support 212 and the rate control membrane 208 with an adhesive (e.g., pressure-sensitive adhesive). In its "inactive" configuration as shown in FIGS. 19-20, the drug delivery assembly 270 of the patch 200 securely retains a drug compound 207 so that it does not flow to any significant extent into the microneedles 230. When it is desired to "activate" the patch, the release member 210 may be peeled away and removed, such as illustrated in FIGS. 21-22, to break the seal previously formed between the release member 210 and the aperture (not shown) of the support 212. Thereafter, the second section 260 may be folded about a fold line "F" as shown by the directional arrow in FIG. 23 so that the rate control membrane 208 is positioned vertically adjacent to the support 212 and in fluid communication therewith. Alternatively, the first section 250 may be folded. Regardless, folding of the sections 250 and/or 260 initiates the flow of a drug compound 207 from the drug delivery assembly 270 and into the channels 231 of the microneedles 230 via the support 212 (See FIG. 24).

The device may deliver an agent at a rate so as to be therapeutically useful. In accord with this goal, a transdermal device may include a housing with microelectronics and other micro-machined structures to control the rate of delivery either according to a preprogrammed schedule or through active interface with the patient, a healthcare professional, or a biosensor. The device may include a material at a surface having a predetermined degradation rate, so as to control release of an agent contained within the device. A delivery rate may be controlled by manipulating a variety of factors, including the characteristics of the formulation to be delivered (e.g., viscosity, electric charge, and/or chemical composition); the dimensions of each device (e.g., outer diameter and the volume of any openings); the number of microneedles on a transdermal patch; the number of individual devices in a carrier matrix; the application of a driving force (e.g., a concentration gradient, a voltage gradient, a pressure gradient); the use of a valve; and so forth.

Transportation of agents through the device may be controlled or monitored using, for example, various combinations of valves, pumps, sensors, actuators, and microprocessors. These components may be produced using standard manufacturing or microfabrication techniques. Actuators that may be useful with the device may include micropumps, microvalves, and positioners. For instance, a microprocessor may be programmed to control a pump or valve, thereby controlling the rate of delivery.

Flow of an agent through the device may occur based on diffusion or capillary action, or may be induced using conventional mechanical pumps or nonmechanical driving forces, such as electroosmosis or electrophoresis, or convection. For example, in electroosmosis, electrodes are positioned on a biological surface (e.g., the skin surface), a microneedle, and/or a substrate adjacent a microneedle, to create a convective flow which carries oppositely charged ionic species and/or neutral molecules toward or into the delivery site.

Flow of an agent may be manipulated by selection of the material forming the microneedle surface. For example, one or more large grooves adjacent the microneedle surface of the device may be used to direct the passage of drug, particularly in a liquid state. Alternatively, the physical surface properties of the device may be manipulated to either promote or inhibit transport of material along the surface, such as by controlling hydrophilicity or hydrophobicity.

The flow of an agent may be regulated using valves or gates as is known in the art. Valves may be repeatedly opened and closed, or they may be single-use valves. For example, a breakable barrier or one-way gate may be installed in the device between a reservoir and the patterned surface. When ready to use, the barrier may be broken or gate opened to permit flow through to the microneedle surface. Other valves or gates used in the device may be activated thermally, electrochemically, mechanically, or magnetically to selectively initiate, modulate, or stop the flow of molecules through the device. In one embodiment, flow is controlled by using a rate-limiting membrane as a "valve."

In general, any agent delivery control system, including reservoirs, flow control systems, sensing systems, and so forth as are known in the art may be incorporated with devices. By way of example, U.S. Pat. Nos. 7,250,037, 7,315,758, 7,429,258, 7,582,069, and 7,611,481 describe reservoir and control systems as may be incorporated in devices.

Agents as may be delivered by the device may be intended for the local area near the device or may be intended for wider distribution. For instance, in one embodiment, the device may deliver agents for pain management or inflammation management to a local area around a joint, for instance in treatment of osteoarthritis or rheumatoid arthritis.

The nanotopography of the device may improve delivery of agents while minimizing foreign body and immune response. This may prove particularly beneficial when considering delivery of oligonucleotides and other therapeutics to the nuclear envelope. In the past, delivery of materials (e.g., plasmids, siRNA, RNAi, and so forth), to the nuclear envelope has proven problematic because even when endocytosis is achieved, proper endosomal delivery to the nuclear envelope has proven difficult, most likely due to foreign body and immune response. Once in the cytoplasm, delivered material is often recycled via late endosomes or degraded in the lysosome. According to disclosed methods, interaction of a microneedle with the ECM may prevent foreign body response within a cell following endocytosis and encourage delivery of the materials to the nucleus.

Delivery of protein therapeutics has likewise proven problematic. For instance, delivery of high molecular weight agents such as protein therapeutics has proven difficult for transdermal delivery routes due to the natural barriers of the skin. The presence of the nanotopography on a microneedle may beneficially affect the thermodynamics of the ECM and improve efficiency of delivery and uptake of protein therapeutics. As utilized herein, the term 'protein therapeutics' generally refers to any biologically active proteinaceous compound including, without limitation, natural, synthetic, and recombinant compounds, fusion proteins, chimeras, and so forth, as well as compounds including the 20 standard amino acids and/or synthetic amino acids. For instance, the presence of the device in or near the stratum granulosum can open tight junctions and allow paracellular transport of high molecular weight agents. In one embodiment, the device may be utilized in transdermal delivery of high molecular weight agents (e.g., agents defining a molecular weight greater than about 400 Da, greater than about 10 kDa, greater than about 20 kDa, or greater than about 100 kDa, e.g., about 150 kDa). Additionally, variation of the surface area to volume ratio of the device may be utilized to alter protein adsorption at the surface of the device, which may in turn alter delivery and cellular uptake of materials. Thus, deliver of a particular material may be optimized through optimization of the surface area/volume ratio of the device.

Even when considering delivery of small molecular weight agents, the device may provide increased efficiency and improved uptake due to interaction of the device with components of the dermal connective tissue and accompanying decrease in foreign body response and improvement in localized chemical potential of the area.

Of course, devices are not limited to targeted delivery of agents. Systemic deliver of agents is also encompassed herein as is withdrawal of an agent from a subject via the device.

There is no particular limitation to agents as may be delivered by use of the device. Agents may include proteinaceous agents such as insulin, immunoglobulins (e.g., IgG, IgM, IgA, IgE), TNF-α, antiviral medications, and so forth; polynucleotide agents including plasmids, siRNA, RNAi, nucleoside anticancer drugs, vaccines, and so forth; and small molecule agents such as alkaloids, glycosides, phenols, and so forth. Agents may include anti-infection agents, hormones, drugs that regulate cardiac action or blood flow, pain control, and so forth. Still other substances which may be delivered in accordance with the present disclosure are agents useful in the prevention, diagnosis, alleviation, treatment, or cure of disease. A non-limiting listing of agents includes anti-Angiogenesis agents, anti-depressants, antidiabetic agents, antihistamines, anti-inflammatory agents, butorphanol, calcitonin and analogs, COX-II inhibitors, dermatological agents, dopamine agonists and antagonists, enkephalins and other opioid peptides, epidermal growth factors, erythropoietin and analogs, follicle stimulating hormone, glucagon, growth hormone and analogs (including growth hormone releasing hormone), growth hormone antagonists, heparin, hirudin and hirudin analogs such as hirulog, IgE suppressors and other protein inhibitors, immunosuppressives, insulin, insulinotropin and analogs, interferons, interleukins, leutenizing hormone, leutenizing hormone releasing hormone and analogs, monoclonal or polyclonal antibodies, motion sickness preparations, muscle relaxants, narcotic analgesics, nicotine, non-steroid anti-inflammatory agents, oligosaccharides, parathyroid hormone and analogs, parathyroid hormone antagonists, prostaglandin antagonists, prostaglandins, scopolamine, sedatives, serotonin agonists and antagonists, sexual hypofunction, tissue plasminogen activators, tranquilizers, vaccines with or without carriers/adjuvants, vasodilators, major diagnostics such as tuberculin and other hypersensitivity agents as described in U.S. Pat. No. 6,569,143 entitled "Method of Intradermally Injecting Substances", the entire content of which is incorporated herein by reference. Vaccine formulations may include an antigen or antigenic composition capable of eliciting an immune response against a human pathogen or from other viral pathogens.

In one preferred embodiment, the device may be utilized in treatment of a chronic condition, such as rheumatoid arthritis, to deliver a steady flow of an agent, to a subject in need thereof. RA drugs that can be delivered via disclosed devices can include symptom suppression compounds, such as analgesics and anti-inflammatory drugs including both steroidal and non-steroidal anti-inflammatory drugs (NSAID), as well as disease-modifying antirheumatic drugs (DMARDs).

The device can include and deliver symptom suppression compounds, such as analgesics and anti-inflammatory drugs, as well as DMARD compounds, including biological DMARDs. While not wishing to be bound to any particular theory, it is understood that the nanometer-scare structures fabricated on the surface of the device improve deliver of the compounds across the dermal barrier. Through utilization of the device, RA drugs can be delivered at a steady concentration over a sustained period. The device can prevent the initial burst of concentration common when utilizing previously known methods for delivery of RA drugs, including oral delivery and injection.

RA drugs as may be incorporated in the device can include, without limitation, one or more analgesics, anti-inflammatories, DMARDs, herbal-based drugs, and combinations thereof. Specific compounds can, of course, fall under one or more of the general categories described herein. For instance, many compounds function as both an analgesic and an anti-inflammatory; herbal-based drugs can likewise function as a DMARD as well as an anti-inflammatory. Moreover, multiple compounds that can fall under a single category can be incorporated in the device. For instance, the device can include multiple analgesics, such as acetaminophen with codeine, acetaminophen with hydrocodone (vicodin), and so forth.

Examples of analgesics and/or NSAIDs as may be incorporated in the devices include analgesics available over the counter (OTC) at relatively low dosages including acetamide (acetaminophen or paracetamol), acetylsalicylic acid (aspirin), ibuprofen, ketoprofen, naproxen and naproxen sodium, and the like. Prescription analgesics and/or anti-inflammatories as may be incorporated in the device can include, without limitation, OTC analgesics at concentrations requiring a prescription, celecoxib, sulindac, oxaprozin, salsalate, piroxicam, indomethacin, etodolac, meloxicam, nabumetone, keteroloc and ketorolac tromethamine, tolmetin, diclofenac, diproqualone, and diflunisal. Narcotic analgesics can include codeine, hydrocodone, oxycodone, fentanyl, and propoxyphene.

The device can include one or more steroidal anti-inflammatory compounds, primarily glucocorticoids, including, without limitation, cortisone, dexamethasone, prednisolone, prednisone, hydrocortisone, triamcinolone, and methylprednisolone, betamethasone, and aldosterone.

DMARDs as may be included in the device can encompass both small molecule drugs and biological agents. DMARDs may be chemically synthesized or may be produced through genetic engineering processes (e.g., recombinant techniques).

Chemically synthesized DMARDs encompassed herein include, without limitation, azathioprine, cyclosporine (cyclosporin, cyclosporine A), D-penicillamine, gold salts (e.g., auranofin, Na-aurothiomalate (Myocrism), chloroquine, hydroxychloroquine, leflunomide, methotrexate, minocycline, sulphasalazine (sulfasalazine), and cyclophosphamide. Biological DMARDs include, without limitation, TNF-α blockers such as etanercept (Enbrel®), infliximab (Remicade®), adalimumab (Humira®), certolizamab pego (Cimzia®) and golumumab (Simponi™); IL-1 blockers such as anakinra (Kineret®); monoclonal antibodies against B cells including rituximab (Rituxan®); T cell costimulation blockers such as abatacept (Orencia®), and IL-6 blockers such as tocilizumab (RoActemra®, Actemra®); a calcineurin inhibitor such as tacrolimus (Prograf®).

The device can incorporate one or more herbal-based or other naturally-derived drugs. For instance, Ayurvedic compounds such as boswellic acid (extract of *Boswellia serrata*) and curcumin (curcuminoids from *Curcuma longa*), as well as other naturally derived compounds such as glucosamine sulfate (produced by hydrolysis of crustacean exoskeletons or fermentation of a grain) can be incorporated in the device.

The device can incorporate multiple RA drugs. For instance, the device can include a combination of DMARDs in addition to an analgesic and/or an anti-inflammatory drug. Common combinations of DMARDs include, for example, methotrexate in combination with hydroxychloroquine, methotrexate in combination with sulfasalazine, sulfasalazine in combination with hydroxychloroquine, and all three of these DMARDs together, i.e., hydroxychloroquine, methotrexate, and sulfasalazine.

The devices can beneficially incorporate large and/or small molecular weight compounds. For instance, in the past, transdermal delivery of protein therapeutics has proven problematic due to the natural barriers of the skin. While not wishing to be bound to any particular theory, the presence of the nanotopography of a microneedle of the device may beneficially interact with cells and ECM of the dermal barrier and improve efficiency of delivery and uptake of protein therapeutics. For instance, the presence of the device in or near the stratum granulosum can open tight junctions and allow paracellular transport of high molecular weight agents. As utilized herein, the term high molecular weight agents generally refers to agents defining a molecular weight greater than about 400 Da, greater than about 10 kDa, greater than about 20 kDa, or greater than about 100 kDa.

Even when considering delivery of smaller molecular weight drugs, the device may provide increased efficiency and improved uptake due to interaction of the device with components of the dermal connective tissue and accompanying decrease in foreign body response and improvement in localized chemical potential of the area. In addition, the device can deliver the drugs at a steady concentration over a sustained period, which can be beneficial.

The present disclosure may be further understood with reference to the Examples provided below.

Example 1

Several different molds were prepared using photolithography techniques similar to those employed in the design and manufacture of electrical circuits. Individual process steps are generally known in the art and have been described Initially, silicon substrates were prepared by cleaning with acetone, methanol, and isopropyl alcohol, and then coated with a 258 nanometer (nm) layer of silicon dioxide according to a chemical vapor deposition process.

A pattern was then formed on each substrate via an electron beam lithography patterning process as is known in the art using a JEOL JBX-9300FS EBL system. The processing conditions were as follows:

Beam current=11 nA
Acceleration voltage=100 kV
Shot pitch=14 nm
Dose=260 µC/cm$^2$
Resist=ZEP520A, ~330 nm thickness
Developer=n-amyl acetate
Development=2 min. immersion, followed by 30 sec. isopropyl alcohol rinse.

A silicon dioxide etch was then carried out with an STS Advanced Oxide Etch (AOE). Etch time was 50 seconds utilizing 55 standard cubic centimeters per minute (sccm)

He, 22 sccm $CF_4$, 20 sccm $C_4F_8$ at 4 mTorr, 400 W coil, 200 W RIE and a DC Bias of 404-411 V.

Following, a silicon etch was carried out with an STS silicon oxide etch (SOE). Etch time was 2 minutes utilizing 20 sccm $Cl_2$ and 5 sccm Ar at 5 mTorr, 600 W coil, 50 W RIE and a DC Bias of 96-102 V. The silicon etch depth was 500 nanometers.

A buffered oxide etchant (BOE) was used for remaining oxide removal that included a three minute BOE immersion followed by a deionized water rinse.

An Obducat NIL-Eitre®6 nanoimprinter was used to form nanopatterns on a variety of polymer substrates. External water was used as coolant. The UV module utilized a single pulsed lamp at a wave length of between 200 and 1000 nanometers at 1.8 W/cm². A UV filter of 250-400 nanometers was used. The exposure area was 6 inches with a maximum temperature of 200° C. and 80 Bar. The nanoimprinter included a semi-automatic separation unit and automatic controlled demolding.

To facilitate the release of the nanoimprinted films from the molds, the molds were treated with Trideca-(1,1,2,2-tetrahydro)-octytrichlorosilane ($F_{13}$-TCS). To treat a mold, the silicon mold was first cleaned with a wash of acetone, methanol, and isopropyl alcohol and dried with a nitrogen gas. A Petri dish was placed on a hot plate in a nitrogen atmosphere and 1-5 ml of the $F_{13}$-TCS was added to the Petri dish. A silicon mold was placed in the Petri dish and covered for 10-15 minutes to allow the $F_{13}$-TCS vapor to wet out the silicon mold prior to removal of the mold.

Five different polymers as given in Table 2, below, were utilized to form various nanotopography designs.

TABLE 2

| Polymer | Glass Transition Temperature, $T_g$ (K) | Tensile Modulus (MPa) | Surface Tension (mN/m) @20° C. |
|---|---|---|---|
| Polyethylene | 140-170 | 100-300 | 30 |
| Polypropylene | 280 | 1,389 | 21 |
| PMMA | 322 | 3,100 | 41 |
| Polystyrene | 373 | 3,300 | 40 |
| Polycarbonate | 423 | 2,340 | 43 |

Several different nanotopography patterns were formed, schematic representations of which are illustrated in FIGS. 25A-25D and the associated images are seen in FIGS. 25A'-25D'. The nanotopography pattern illustrated in FIG. 25E was a surface of a flat substrate purchased from NTT Advanced Technology of Tokyo, Japan. The patterns were designated DN1 (FIGS. 25A and 25A'), DN2 (FIGS. 25B and 25B'), DN3 (FIGS. 25C and 25C'), DN4 (FIGS. 25D and 25D') and NTTAT2 (FIG. 25E). SEM images of the molds are shown in FIGS. 25A', 25B', and 25C', and images of the films are shown in FIGS. 25D' and 25E. FIG. 8 illustrates a nanopatterned film formed by use of the mold of FIGS. 25A and 25A' (DN1). In this particular film, the polymer features were drawn by temperature variation as previously discussed. The surface roughness of the pattern of FIG. 25E was found to be 34 nanometers.

The pattern illustrated in FIGS. 7C and 7D was also formed according to this nanoimprinting process. This pattern included the pillars 72 and pillars 62, as illustrated. Larger pillars 72 were formed with a 3.5 micrometer (μm) diameter and 30 μm heights with center-to-center spacing of 6.8 Pillars 62 were 500 nanometers in height and 200 nanometers in diameter and a center-to-center spacing of 250 nanometers.

The nanoimprinting process conditions used with polypropylene films are provided below in Table 3.

TABLE 3

| Time (s) | Temperature (C.) | Pressure (Bar) |
|---|---|---|
| 10 | 50 | 10 |
| 10 | 75 | 20 |
| 10 | 100 | 30 |
| 420 | 160 | 40 |
| 180 | 100 | 40 |
| 180 | 50 | 40 |
| 180 | 25 | 40 |

Example 2

Films were formed as described above in Example 1 including various different patterns and formed of either polystyrene (PS) or polypropylene (PP). The underlying substrate varied in thickness. Patterns utilized were DN2, DN3, or DN4 utilizing formation processes as described in Example 1. The pattern molds were varied with regard to hole depth and feature spacing to form a variety of differently-sized features having the designated patterns. Sample no. 8 (designated BB1) was formed by use of a 0.6 μm millipore polycarbonate filter as a mold. A 25 μm polypropylene film was laid over the top of the filter and was then heated to melt such that the polypropylene could flow into the pores of the filter. The mold was then cooled and the polycarbonate mold dissolved by use of a methylene chloride solvent.

SEMs of the formed films are shown in FIGS. 26-34 and the characteristics of the formed films are summarized in Table 4, below.

TABLE 4

| Sample No. | FIG. | Pattern | Material | Film thickness (μm) | Pattern Feature[1] | Cross Sectional Dimension[2] | Feature height[3] | Aspect Ratio | Surface Roughness (nm) | Fractal Dimension | Water Contact Angle |
|---|---|---|---|---|---|---|---|---|---|---|---|
| 1 | 26 | DN3 | PS | 75 | A | 1100 nm | 520 nm | 0.47 | 150 | 2.0 | 100° |
|  |  |  |  |  | B | 400 nm | 560 nm | 1.4 |  |  |  |
|  |  |  |  |  | C | 200 nm | 680 nm | 3.4 |  |  |  |
| 2 | 27A, 27B | DN2 | PP | 5.0 | n/a | 200 nm | 100 nm | 0.5 | 16 | 2.15 | 91° |
| 3 | 28 | DN2 | PS | 75 | n/a | 200 nm | 1.0 μm | 5 | 64 | 2.2 | 110° |
| 4 | 29 | DN2 | PP | 25.4 | n/a | 200 nm | 300 nm | 1.5 | 38 | 1.94 | 118° |
| 5 | 30 | DN3 | PS | 75 | A | 1100 nm | 570 nm | 0.52 | 21.1 | 1.98 | 100° |
|  |  |  |  |  | B | 400 nm | 635 nm | 1.6 |  |  |  |
|  |  |  |  |  | C | 200 nm | — | — |  |  |  |
| 6 | 31 | DN4 | PS | 75 | n/a | 200 nm | — | — | 30.6 | 2.04 | 80° |
| 7 | 32 | DN4 | PP | 25.4 | n/a | 200 nm | — | — | 21.4 | 2.07 | 112° |

TABLE 4-continued

| Sample No. | FIG. | Pattern | Material | Film thickness (μm) | Pattern Feature[1] | Cross Sectional Dimension[2] | Feature height[3] | Aspect Ratio | Surface Roughness (nm) | Fractal Dimension | Water Contact Angle |
|---|---|---|---|---|---|---|---|---|---|---|---|
| 8 | 33 | BB1 | PP | 25.4 | n/a | 600 nm | 18 μm | 30 | 820 | 2.17 | 110° |
| 9 | 34 | DN3 | PP | 5 | A | 1100 nm | 165 nm | 0.15 | 50 | 2.13 | — |
|   |    |     |    |   | B | 400 nm | 80 nm | 0.2 |    |      |   |
|   |    |     |    |   | C | 200 nm | 34 nm | 0.17 |   |      |   |

[1]Pattern Features as shown on the FIGS.
[2]Cross sectional dimension values were derived from the mold as an approximation of the maximum dimension of the structures, although it should be understood that the actual dimension of any given structure may vary slightly as may be seen in the FIGS.
[3]Feature heights are provided as the average of several individually determined feature heights.

For each sample AFM was utilized to characterize the film. Characterizations included formation of scanning electron micrograph (SEM), determination of surface roughness, determination of maximum measured feature height, and determination of fractal dimension.

The atomic force microscopy (AFM) probe utilized was a series 16 silicon probe and cantilever available from μMasch. The cantilever had a resonant frequency of 170 kHz, a spring constant of 40 N/m, a length of 230±5 μm, a width of 40±3 μm, and a thickness of 7.0±0.5 μm. The probe tip was an n-type phosphorous-doped silicon probe, with a typical probe tip radius of 10 nanometers, a full tip cone angle of 40°, a total tip height of 20-25 μm, and a bulk resistivity 0.01-0.05 ohm-cm.

The surface roughness value given in Table 4 is the arithmetical mean height of the surface area roughness parameter as defined in the ISO 25178 series.

The Fractal Dimension was calculated for the different angles by analyzing the Fourier amplitude spectrum; for different angles the amplitude Fourier profile was extracted and the logarithm of the frequency and amplitude coordinates calculated. The fractal dimension, D, for each direction is then calculated as $$D=(6+s)/2,$$

where s is the (negative) slope of the log-log curves. The reported fractal dimension is the average for all directions.

The fractal dimension can also be evaluated from 2D Fourier spectra by application of the Log Log function. If the surface is fractal, the Log Log graph should be highly linear, with a negative slope (see, e.g., Fractal Surfaces, John C. Russ, Springer-Verlag New York, LLC, July, 2008).

Example 3

HaCaT human skin epithelial cells were grown in DMEM, 10% FBS, 1% penicillin/streptomycin at 37° C., 5% $CO_2$ for 24 hours at a concentration of 25,000 cell/cm² in 6 well plates. Plates either had polypropylene nanopatterned films formed as described above in Example 1 and designate DN1, DN2 (Sample 4 of Table 4), DN3 or untreated surface at the bottom of the well. Nanopatterned films were adhered in place with cyanoacrylate.

Cells were detached from the surfaces with 1 mL of trypsin per well for 10 minutes, quenched with 1 mL growth medium (same as above), then transferred to a microfuge tube and pelleted at 1200 rpm for 7 minutes.

RNA was isolated from pelleted cells using the RNeasy miniprep kit from Qiagen using the manufacturer's protocol. Briefly, cells were lysed, mixed with ethanol and spun down in a column. Lysates were then washed 3 times, treated with DNase and eluted in 40 μl volumes.

cDNA was created from the RNA isolated using the RT first strand kit from SA Biosciences. Briefly, RNA was treated with DNase again at 42° C. for 5 minutes. Random primers and reverse transcriptase enzyme was then added and incubated at 42° C. for 15 minutes, then incubated at 95° C. for 5 minutes to stop reaction.

qPCR was then performed on the cDNA samples using RT profiler custom PCR array from SA Biosciences with primers for IL1-β, IL6, IL8, IL10, IL1R1, TNFα, TGFβ-1, PDGFA, GAPDH, HDGC, RTC and PPC. Briefly, cDNA was mixed with SYBR green and water, and then added to a PCR plate pre-fixed with the correct sense and antisense primer pair for the gene of interest. The plate was then run on an ABI StepOnePlus PCR machine heated to 95° C. for 10 minutes, then for 45 cycles of: 15 seconds at 95° C. and 1 minute at 60° C.

Delta delta $C_T$ analysis was performed using GAPDH as the internal control. HDGC, RTC and PPC levels were used as additional internal controls for activity and genomic DNA contamination.

One-way ANOVA and Tukey's 2-point tests were then used to determine statistical significance in the differences between surfaces.

Table 5, below, presents the protein expressions obtained as the fold change in expression on nanoimprinted structures produced on polypropylene films versus expression on an unstructured film.

TABLE 5

| Mold | IL1-β | IL6 | IL8 | IL10 | IL1R1 | TNFα | TGFβ1 | PDGFA |
|---|---|---|---|---|---|---|---|---|
| DN1 | 2.24 | 3.33 | 0.36 | 1.17 | 0.6 | 0.57 | 0.37 | 1.37 |
| DN2 | 3.18 | 3.2 | 0.46 | 0.43 | 0.36 | 0.57 | 0.42 | 1.23 |
| DN3 | 3.36 | 2.7 | 0.47 | 5.83 | 1.6 | 0.37 | 0.35 | 0.64 |

Example 4

Methods as described in Example 3 were utilized to examine the expression level for several different cytokines from HaCaT human skin epithelial cells when the cells were allowed to develop on a variety of different polypropylene (PP) or polystyrene (PS) films, formed and patterned as described above. The expression level for each cytokine was compared to that from the same cell type cultured on standard tissue culture polystyrene (TCPS) and induced with lipopolysaccharide (LPS). Results are shown in Table 6, below.

Cells developed on a polypropylene film nanopatterned with a DN2 pattern, as described above (Sample 4 of Table 4), were found to upregulate expression of IL-1β, IL-1ra, IL-10, and MIP-1β downregulate expression of IL-4, IL-13, MIG, KC, IL-2, MIP-1, TNF-α, IL-12, IL-16, and IL-1α as compared to TCPS.

Several other films were examined for effect on cellular expression of different cytokines. Films were designated as follows:

1—DN2 pattern on a 75 μm polystyrene film (Sample 3 of Table 4)
2—DN3 pattern on a 75 μm polystyrene film (Sample 1 of Table 4)
3—DN4 pattern on a 75 μm polystyrene film (Sample 6 of Table 4)
4—unimprinted 75 μm polystyrene film
5—DN2 pattern on a 25.4 μm polypropylene film (Sample 4 of Table 4)
6—DN4 pattern on a 25.4 μm polypropylene film (Sample 7 of Table 4)
7—DN2 pattern on a 5 μm polypropylene film (Sample 2 of Table 4)
8—BB1 polypropylene film (Sample 8 of Table 4)
9—unimprinted 25.4 μm polypropylene film
10—unimprinted 5 μm polypropylene film Results are illustrated in Table 6, below. Results are provided as follows:
-- expression level was below the testing threshold
- expression level was lower than that for TCPS
= expression level was similar to that for TCPS
+ expression level was above that for TCPS, but below that when induced with LPS
++ expression level was similar to that for induction with LPS
+++ expression level was above that for induction with LPS

TABLE 6

| | Film | | | | | | | | | |
|---|---|---|---|---|---|---|---|---|---|---|
| | 1 | 2 | 3 | 4 | 5 | 6 | 7 | 8 | 9 | 10 |
| IL-1α | -- | -- | -- | -- | -- | -- | -- | -- | -- | -- |
| IL-1β | ++ | -- | -- | ++ | -- | -- | -- | -- | -- | -- |
| IL-12 | = | = | = | = | = | = | = | = | = | = |
| TNF-α | =+ | = | = | = | = | = | = | =+ | = | = |
| MCP-1 | =+ | = | = | = | = | = | = | =+ | = | = |
| IL-2 | = | =— | =+ | = | = | = | = | = | -- | = |
| KC | -- | --— | = | = | = | = | = | = | — | — |
| M1P-1α | -- | -- | -- | +++ | -- | -- | + | -- | +++ | +++ |
| MIP-1b | ++ | + | = | = | = | + | = | --- | --- | = |
| MIG | = | -- | = | + | --- | --- | -- | --- | --- | = |
| GM-CSI | -- | -- | -- | -- | -- | -- | -- | -- | -- | -- |
| IL-4 | -- | -- | -- | -- | -- | -- | -- | -- | -- | -- |
| IL-13 | -- | -- | -- | ++ | -- | -- | -- | -- | -- | -- |
| IL-10 | — | — | = | = | = | = | = | = | = | = |

Example 5

HaCaT human skin epithelial cells were grown in DMEM, 10% FBS, 1% penicillin/streptomycin at 37° C., 5% $CO_2$ for 24 hours at a concentration of 25,000 cell/cm$^2$ in 6 well plates. Plates either had a polypropylene film formed as described above in Example 1 with designation DN1, DN2 (Sample 4 of Table 4), DN3 or an untreated surface at the bottom of the well. Films were adhered in place with cyanoacrylate.

Media was collected from each well and analyzed for cytokine production with a Milliplex Map Kit from Millipore. Beads to detect IL-1β, IL-1ra, IL-6, IL-8, IL-10, PDGF-AA, PGGF-AB/BB and TNF-α were used. Readings were done on a BioRad BioPlex machine. Briefly, media was placed into microplate wells with filters. Primary beads were added and incubated at room temperature for 1 hour with shaking. The plates were then washed and incubated with detection antibodies for 30 minutes at room temperature with shaking. Strepavidin-phycoerythrin was then added and incubated at room temperature for an additional 30 minutes. Plates were then washed, beads were resuspended in assay buffer and median fluorescent intensity was analyzed on the BioPlex.

Example 6

The permeability effects of films patterned as described herein were determined on a monolayer of Caco-2 cells (human epithelial colorectal adenocarcinoma cells).

Films formed as described above in Example 1 and Example 2 were utilized including polypropylene (PP) or polystyrene (PS) films formed with patterns designated as DN2, DN3, and DN4. A fourth film, designated as BB1 (described in Example 2, above) was also used. The protocol was run with multiple examples of each film type.

The general protocol followed for each film was as follows: Materials

Cell culture inserts 0.4 μm pore size HDPET membrane (BD Falcon)
24 well plate (BD Falcon)
Caco-2 media
Nanostructured membranes as described above
IgG-FITC (Sigma Aldrich)
BSA-FITC (Sigma Aldrich)
Minimum Essential Medium no phenol red (Invitrogen)
TEER voltmeter
Warmed PBS
Black 96-well plate
Aluminum foil Protocol 1. Seed Caco-2 cells on collagen coated well inserts 2 weeks before permeability assay is to be performed. Collagen coated plates are made by making a 1:1 volume of 100% ethanol to collagen. Dry surfaces in sterile hood overnight until dry.

2. Make 0.1 mg/mL solution of FITC-conjugated molecule (BSA, IgG, etc) of interest in phenol red free Alpha MEM media. Wrap in aluminum foil to protect from light.

3. Check for confluency of Caco-2 cells by measuring the resistance.
Resistance should be above ~600 Ohms for confluency.

4. Aspirate old media from cell culture inserts on apical and basolateral sides. Rinse with PBS to remove any residual phenol-red dye.

5. Add 0.5 mL of FITC-conjugated solution on apical side of each insert.

6. In another 24 well plate with cell culture inserts, add 0.5 mL of warmed PBS.

7. Transfer inserts to the plate with PBS. Blot the bottom of the insert on a Kim wipe to remove residual phenol red.

8. t=0-time point: sample 75 μL from the basolateral side of insert and transfer to a black-bottom 96-well plate. Replace the volume with 75 μL of warmed PBS. Record the resistance of each well using the "chopstick" electrodes.

9. Carefully add the membrane to the appropriately labeled well. Controls are the unimprinted membranes and the cells alone. Check under a microscope that the membranes make direct contact to the cells. You should be able to see a sharp circle, indicating contact with the cells.

10. t=0 time point: repeat step 7 and then place in the incubator for 1 hour 11. t=1 time point: repeat step 7 and then place in the incubator for 1 hour 12. t=2 time point: repeat step 7

13. Measure fluorescence signal using a spectrofluorometer plate reader. FITC (excitation=490 nanometers, emission=520 nanometers)

Results

Films utilized and results obtained are summarized in Table 7, below.

TABLE 7

| | Sample No. (see Table 4) | | | | | | |
|---|---|---|---|---|---|---|---|
| | 2 | 3 | 4 | 5 | 6 | 7 | 8 |
| Pattern | DN2 | DN2 | DN2 | DN3 | DN4 | DN4 | BB1 |
| Material | PP | PS | PP | PS | PS | PP | PP |
| Effective Compression Modulus (MPa) | 5.3 | 16.3 | 0.29 | 10.4 | 32.3 | 4.8 | 7.8 |
| Effective Shear Modulus (MPa) | 5.32 | 58.9 | 218 | 319 | 77.8 | 4.4 | 26.7 |
| BET Surface Area (m$^2$/g) | — | 0.11 | — | 0.44 | — | 4.15 | — |
| BSA permeability increase at 120 min. (MW 66 kDa) | — | 2 | 1.9 | 3.3 | 2 | 1.4 | 1 |
| IgG permeability increase at 120 min. (MW 150 kDa) | — | 1 | — | 1 | 3.5 | — | — |

Moduli were determined according to standard methods as are known in the art as described by Schubert, et al. (Sliding induced adhesion of stiff polymer microfiber arrays: 2. Microscale behaviour, Journal Royal Society, Interface, Jan. 22, 2008. 10.1098/rsif.2007.1309)

The contact angles were measured by placing a drop of water on the surface according to standard practice. (See, e.g., Woodward, First Ten Angstroms, Portsmouth, Va.).

Figure 35:
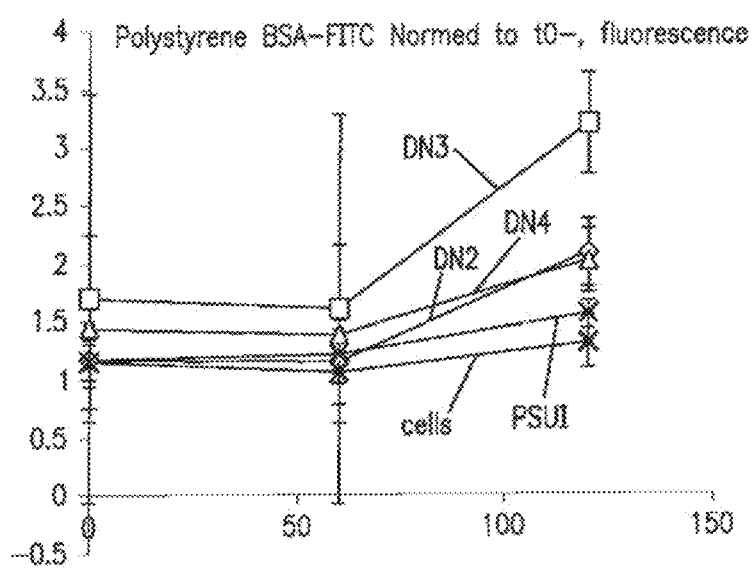
FIG. 35 graphically illustrates the effects on permeability to bovine serum albumin (BSA) in a monolayer of cells on polystyrene films patterned with nanopatterns as described herein.

FIG. 35 graphically illustrates the effects on permeability to bovine serum albumin (BSA) in a monolayer of cells on polystyrene films patterned with nanopatterns as described herein. The film patterns included a DN2 pattern (sample no. 3), a DN3 pattern (sample no. 5), and a DN4 pattern (sample no. 6), as indicated. Also shown are results for a non-patterned PS film (marked PSUI on FIG. 35) and a layer of cells with no adjacent film (marked 'cells' on FIG. 35). The results are illustrated as fold increase in permeability as a function of time measured in hours.

Figure 36A:
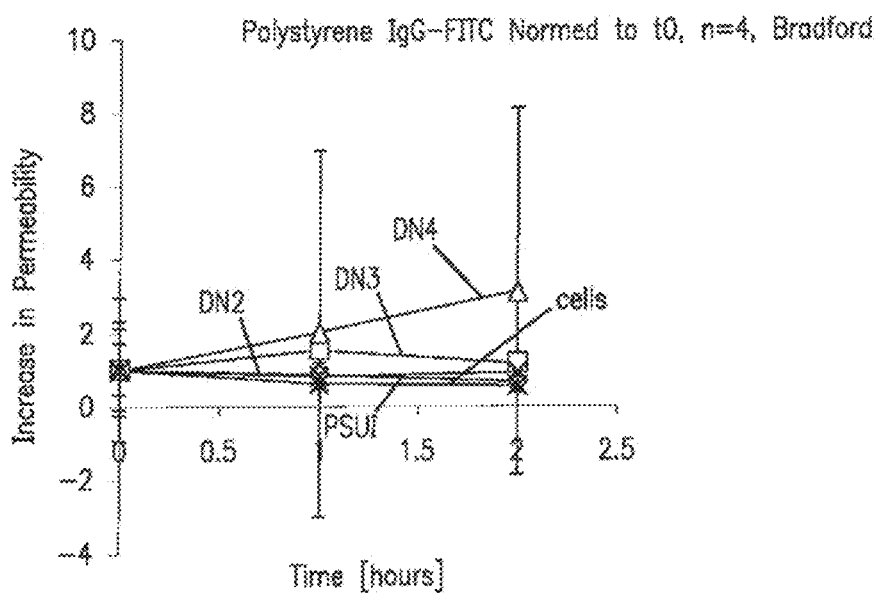
FIGS. 36A and 36B graphically illustrate the effects on permeability to immunoglobulin-G (IgG) in a monolayer of cells on polystyrene films patterned with nanopatterns as described herein.
Figure 36B:
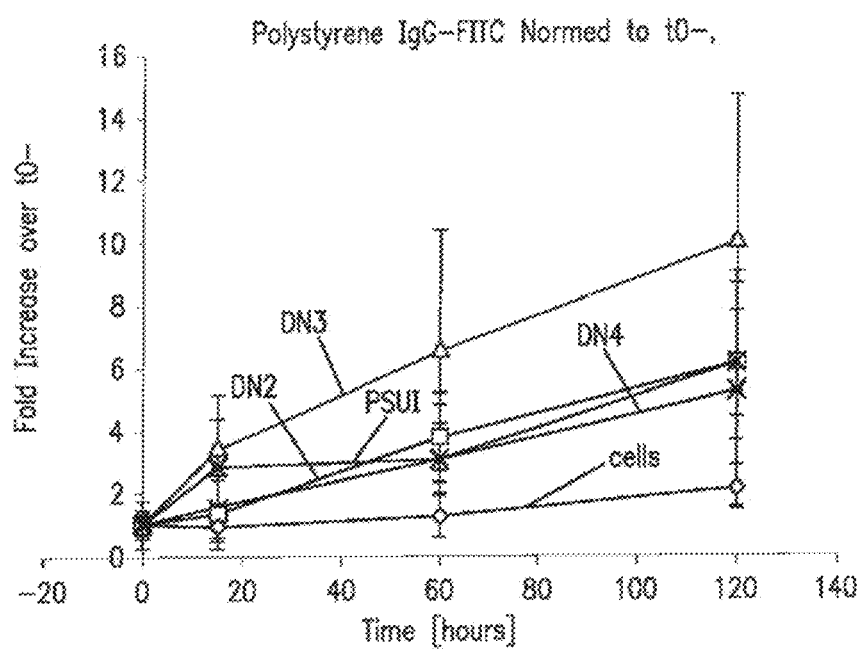

FIG. 36A and FIG. 36B graphically illustrate the effects on permeability to immunoglobulin-G (IgG) in a monolayer of cells on polystyrene films patterned with nanopatterns as described herein. The film patterns included a DN2 pattern (sample no. 3), a DN3 pattern (sample no. 5), and a DN4 pattern (sample no. 6), as indicated. Also shown are results for a non-patterned film (marked PSUI on FIGS. 36A and 36B) and a layer of cells with no adjacent film (marked 'cells' on FIGS. 36A and 36B). The two figures show the data over two different time scales.

The BSA signal was read on a fluorometer and the IgG signal was read on a spectrophotometer.

Figure 37A:
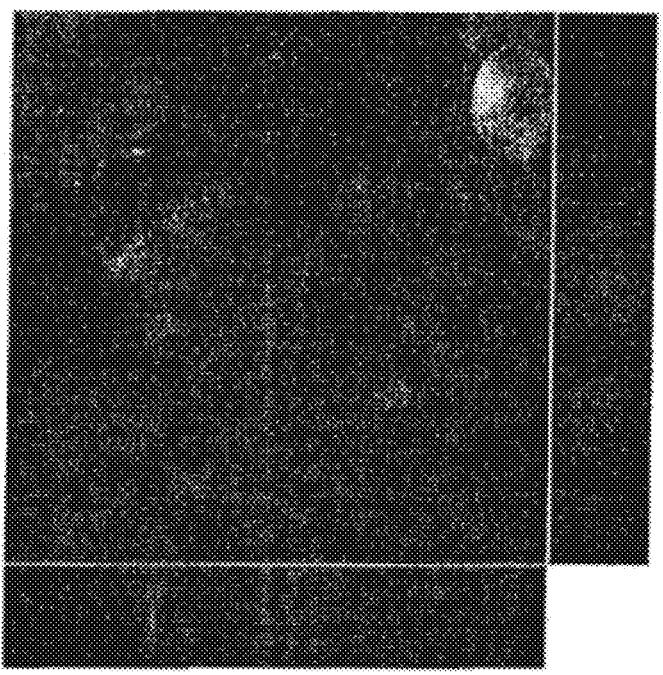
FIGS. 37A and 37B are 3D live/dead flourescein staining images showing paracellular and transcellular transport of IgG across a monolayer of cells on a polystyrene patterned surface as described herein.
Figure 37B:
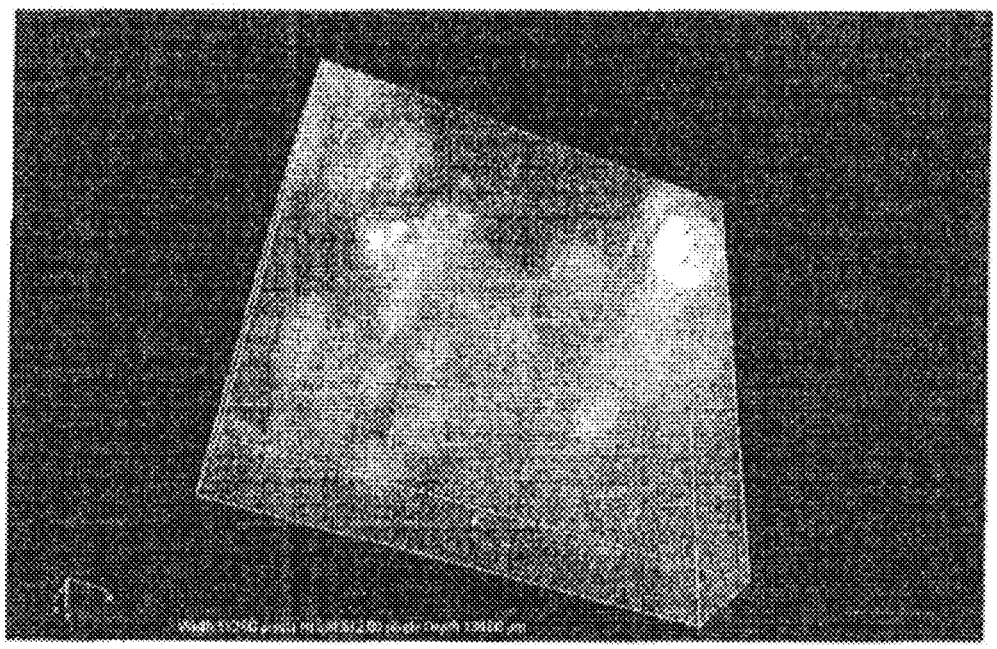

FIGS. 37A and 37B are 3D live/dead flourescein staining images showing paracellular and transcellular transport of IgG across a monolayer of cells on a polystyrene DN4 patterned surface (sample no. 6).

Figure 38:
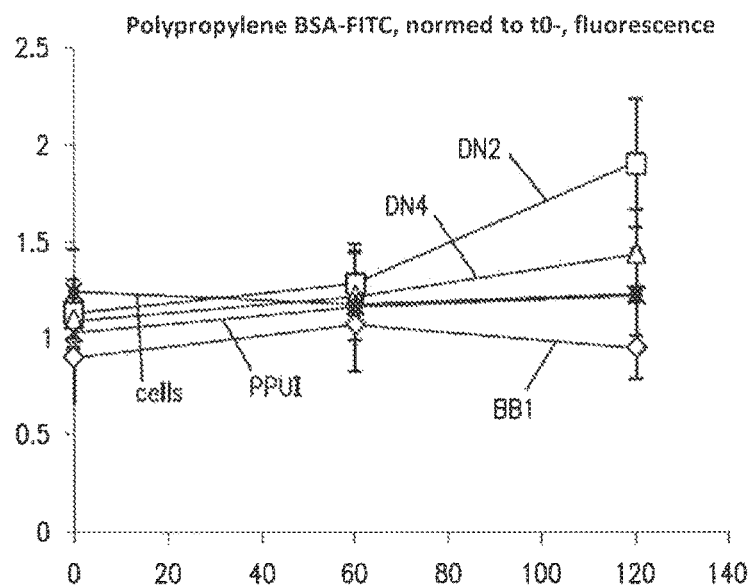
FIG. 38 graphically illustrates the effects on permeability to BSA in a monolayer of cells on polypropylene films patterned with nanopatterns as described herein.

FIG. 38 graphically illustrates the effects on permeability to BSA in a monolayer of cells on polypropylene films patterned with nanopatterns as described herein. Patterns included BB1 (sample no. 8), DN2 (sample no. 4), and DN4 (sample no. 7), as indicated. Also shown are results for a non-patterned film (marked PPUI on FIG. 38) and a layer of cells with no adjacent film (marked 'cells' on FIG. 38).

Figure 39:
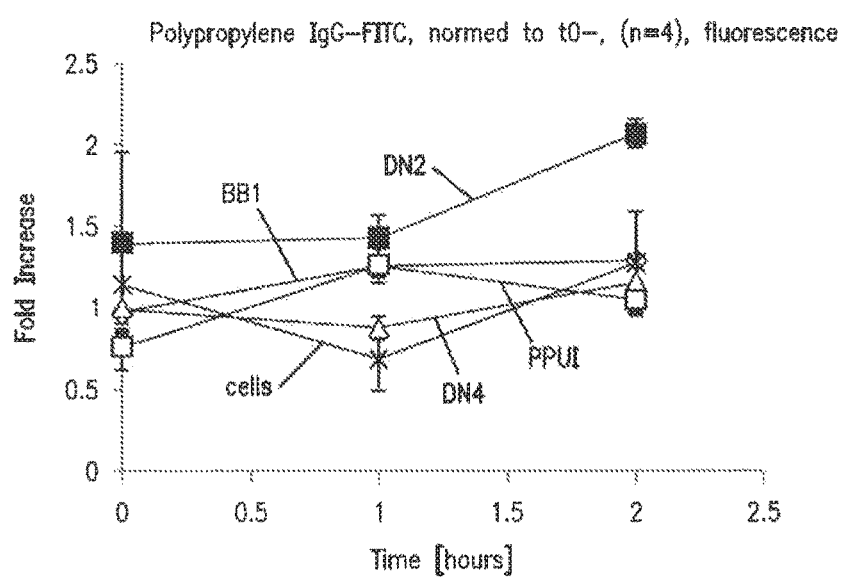
FIG. 39 graphically illustrates the effects on permeability to IgG in a monolayer of cells on polypropylene films patterned with nanopatterns as described herein.

FIG. 39 graphically illustrates the effects on permeability to IgG in a monolayer of cells on polypropylene films patterned with nanopatterns as described herein. Patterns included BB1 (sample no. 8), DN2 (sample no. 4), and DN4 (sample no. 7), as indicated. Also shown are results for a non-patterned film (marked PSUI on FIG. 39) and a layer of cells with no adjacent film (marked 'cells' on FIG. 39).

Figure 40A:
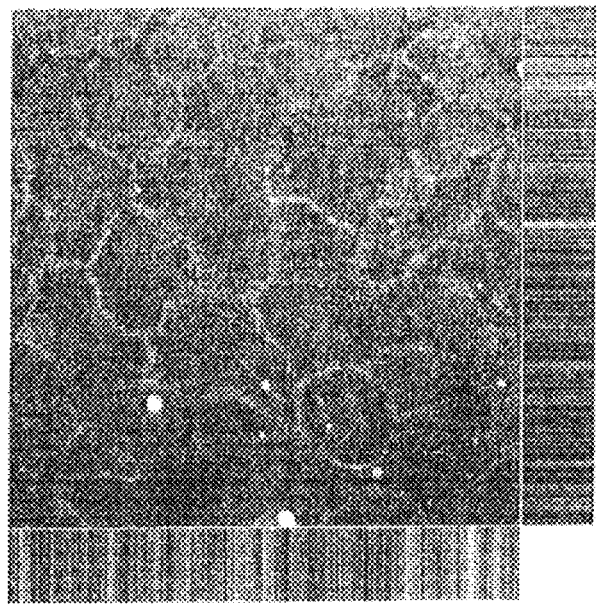
FIGS. 40A and 40B are 3D live/dead flourescein staining images showing paracellular transport of IgG across a monolayer of cells on a polypropylene patterned surface as described herein.
Figure 40B:
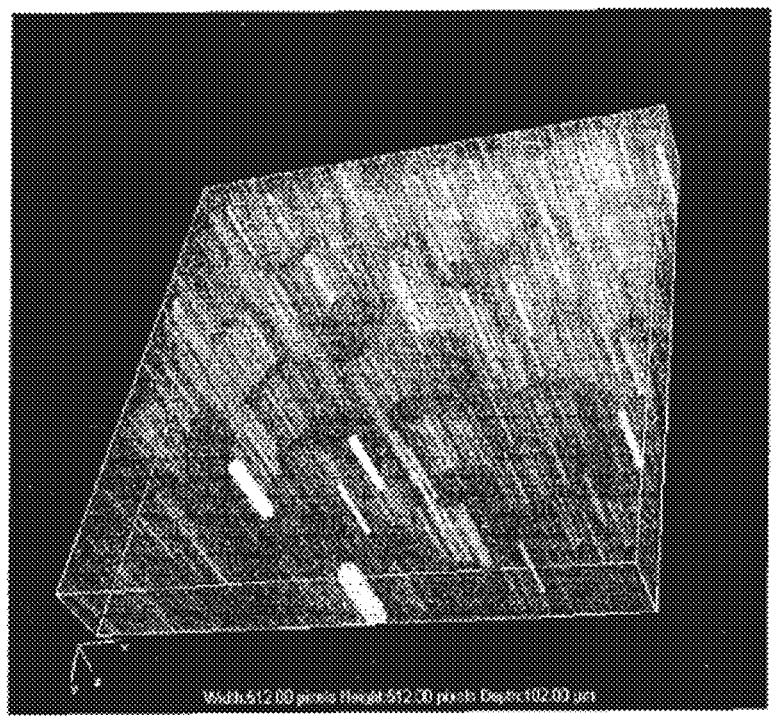

FIGS. 40A and 40B are 3D live/dead flourescein staining images showing paracellular transport of IgG across a monolayer of cells on a polypropylene DN2 patterned surface (sample no. 4).

FIGS. 41A-41F are scanning electron microscopy (SEM) images of Caco-2 cells cultured on nanopatterned surfaces. Specifically, FIGS. 41A and 41B illustrate Caco-2 cells on a flat polystyrene control film. FIGS. 41C and 41D illustrate Caco-2 cells on a polystyrene film patterned with a DN2 pattern (sample no. 3) as described above, and FIGS. 41E and 41F illustrate Caco-2 cells on a polystyrene film patterned with a DN3 pattern (sample no. 5) as described above.

Example 7

Figure 43:
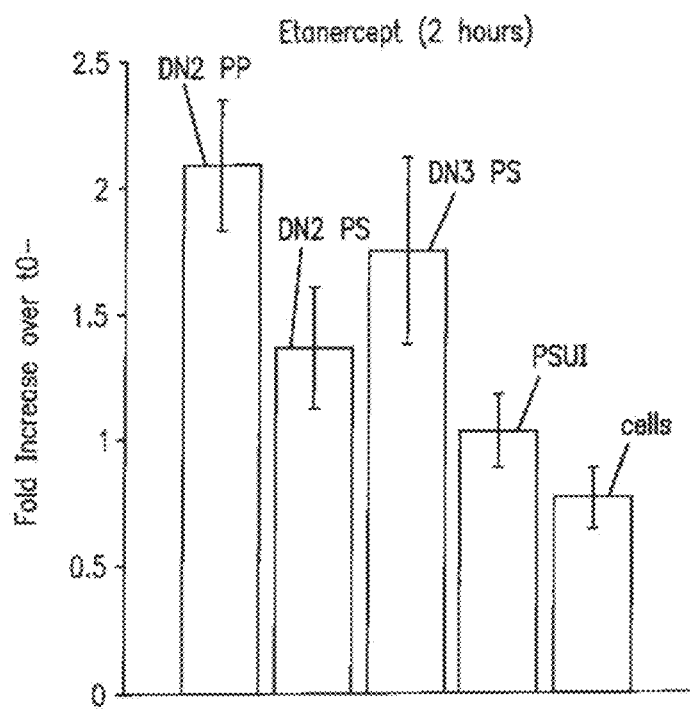
FIG. 43 illustrates the increase in permeability to etanercept of a cellular layer following two hours of contact with a polypropylene or polystyrene films patterns with nanopatterns as described herein.

A method as described in Example 6 was utilized to examine the permeability of a monolayer of Caco-2 cells to the fusion protein therapeutic etanercept (marketed under the trade name as Enbrel®). FIG. 42 graphically illustrates the results for cell layers grown on several different patterned substrates including both polypropylene (DN2 PP—Sample 4 of Table 4) and polystyrene (DN2 PS—Sample 3 of Table 4 and DN3 PS—Sample 1 of Table 4) as well as an unimprinted polystyrene membrane (PSUI) and a layer of cells with no membrane (cells). Results are shown as a fold change from initial permeability with time. FIG. 43 illustrates the fold increase in permeability from initial t=0 at two hours (t=2) following addition of the membrane to the well for the substrates and cellular layer of FIG. 42.

Example 8

An array of microneedles including a nanopatterned surface was formed. Initially, an array of microneedles as illustrated in FIG. 2 was formed on a silicon wafer via a photolithography process. Each needle included two oppositely placed side channels, aligned with one through-die hole in the base of the needle (not visible on FIG. 2).

Microneedles were formed according to a typical micromachining process on a silicon based wafer. The wafers were layered with resist and/or oxide layers followed by selective etching (oxide etching, DRIE etching, iso etching), resist stripping, oxide stripping, and lithography techniques (e.g., iso lithography, hole lithography, slit lithography) according to standard methods to form the array of microneedles.

Following formation of the microneedle array, a 5 μm polypropylene film including a DN2 pattern formed thereon as described above in Example 1, the characteristics of which are described at sample 2 in Table 4, was laid over the microneedle array. The wafer/film structure was held on a heated vacuum box (3 in. $H_2O$ vacuum) at elevated temperature (130° C.) for a period of one hour to gently pull the film over the surface of the microneedles while maintaining the nanopatterned surface of the film.

Figure 44:
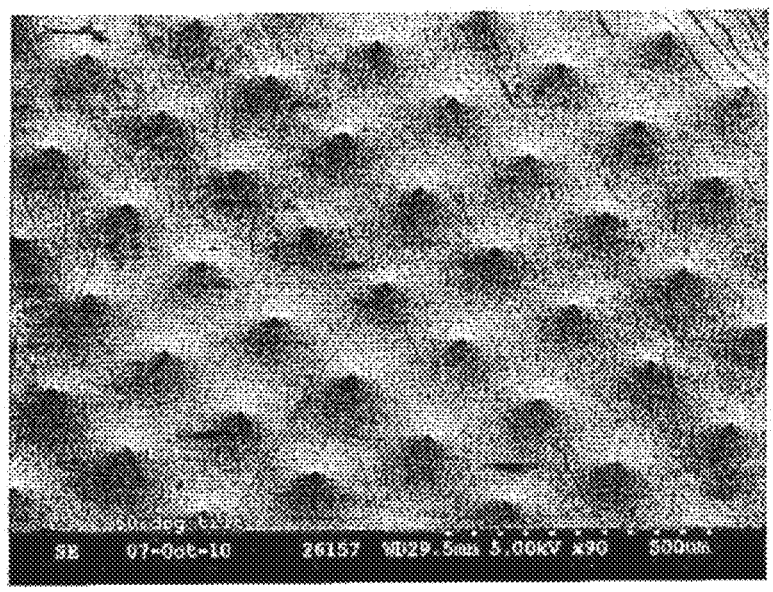
FIG. 44 is an array of microneedles including a surface layer defining a pattern of nanostructures thereon.
Figure 45:
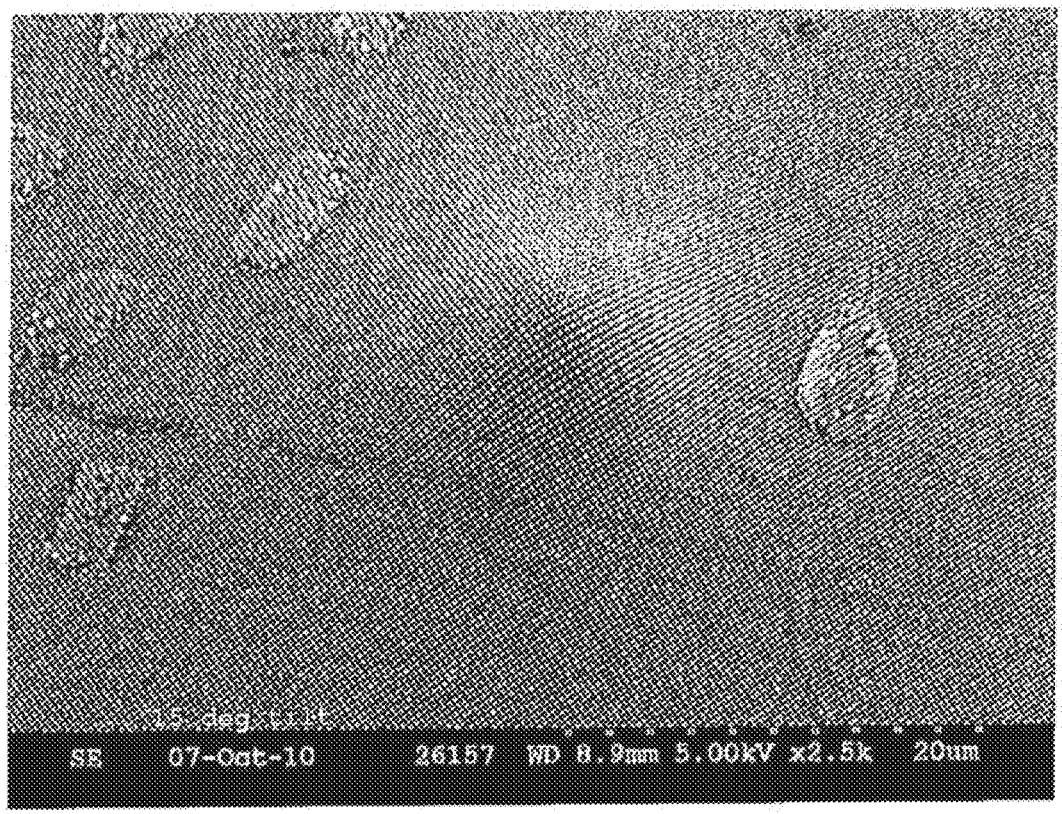
FIG. 45 is a single microneedle of the array of FIG. 44.

FIG. 44 illustrates the film over the top of the array of microneedles, and FIG. 45 is a closer view of a single needle of the array including the nanopatterned film overlaying the top of the needle.

Example 9

Transdermal patches including microneedle arrays formed as described in Example 8 were formed. Patches were formed with either a DN2 pattern or a DN3 pattern on the microneedle array. The films defining the patterns that were applied to the microneedles are described in Table 8, below. Film 1 is equivalent to sample no. 2 of Table 4 and Film 2 is equivalent to sample no. 9 of Table 4.

TABLE 8

| Property | Film 1 | Film 2 |
|---|---|---|
| Pattern | DN2 | DN3 |
| Material | polypropylene | polypropylene |
| Film Thickness | 5 μm | 5 μm |
| Height of structures | 100 nm | 165 nm, 80 nm, 34 nm |
| Aspect ratio of structures | 0.5 | 0.15, 0.2, 0.17 |
| Average Surface Roughness $R_A$ | 16 nm | 50 nm |
| Fractal Dimension | 2.15 | 2.13 |

Control patches were also formed that had no pattern formed on the film and subsequently applied to the array of microneedles. Transdermal and subcutaneous formulations of etanercept (Enbrel®) were prepared according to instructions from the drug supplier. The subcutaneous dose formulation (for the positive control) was prepared to facilitate a 4 mg/kg subcutaneous drug dose. The concentration of Enbrel® for transdermal delivery was adjusted such that an intended dosing of 200 mg/kg was achieved in a 24 hr period.

A total of 10 BALB/C mice (assigned designations #1-#10) were used in the study, 8 were transdermally dosed with Enbrel® (group 1) and 2 were subcutaneously dosed with Enbrel® (group 2) as described in Table 9, below. The transdermal patches were applied to shaved skin areas and holes formed near the microneedle tips upon application of the patch to the skin.

TABLE 9

| Group No. | Test Article | Drug | Dose Route | Dose Level | Dose volume | Blood Collection Time Points | Animal Number |
|---|---|---|---|---|---|---|---|
| 1 | Transdermal patch | Enbrel ® | Transdermal | 5 mg/subject | 0.2 ml | Pre-patch | #1, #5 |
|  |  |  |  |  |  | 0.5 h | #2, #6 |
|  |  |  |  |  |  | 2 h | #3, #7 |
|  |  |  |  |  |  | 6 h | #4, #8 |
|  |  |  |  |  |  | 24 h | #2, #6 |
|  |  |  |  |  |  | 72 h | #3, #7 |
| 2 | Subcutaneous delivery | Enbrel ® | Subcutaneous | 4 mg/kg | 0.1 ml | 24 h | #9, #10 |

Transdermal patches used included both those defining a nanotopography on the surface (DN2 and DN3 patterns, as described above), as well as patches with no pattern of nanotopography.

Samples of whole blood were collected at the time points indicated in Table 8. Approximately 100 to 200 μl blood was taken via mandibular bleeding and then centrifuged at approximately 1300 rpm for 10 minutes in a refrigerated centrifuge (set at 4° C.). The resulting serum was aspirated and transferred within 30 minutes of blood collection/centrifugation to appropriately labeled tubes. The tubes were frozen and stored in the dark at ≤−70° C. until they were analyzed for levels of Enbrel® using Human sTNF-receptor ELISA kit (R&D Systems cat #DRT200). The space time between two blood samplings on the same subject was 24 hours, to prevent unnecessary stress placed on the subject.

Figure 46:
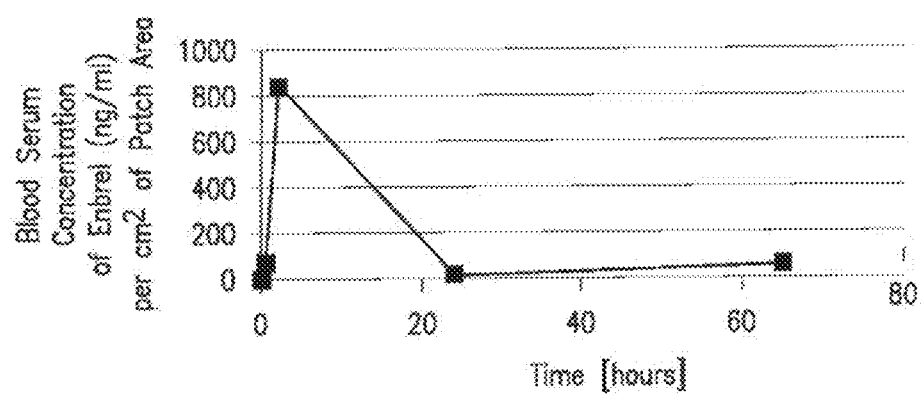
FIG. 46 graphically illustrates the PK profile of a protein therapeutic delivered with a device as described herein.

FIG. 46 graphically illustrates the average PK profile of the transdermal patches that defined a nanotopography thereon. An average of the results for all patches including nanotopography were used to represent the overall effect of incorporating a nanotopography in conjunction with a microneedle transdermal patch. As can be seen, the blood serum level rose rapidly to over 800 ng/mL/cm² of patch area within the first two hours of attachment. Following, the blood serum level gradually declined to negligible within 24 hours of attachment. The data used to develop FIG. 46 is provided below in Table 10.

TABLE 10

| Time (hr) | Blood serum concentration (ng/ml) |
|---|---|
| 0 | 0 |
| 0.5 | 192.1 |
| 2 | 249.25 |
| 6 | 24.4 |
| 24 | 7.2 |
| 65 | 4.0875 |

Figure 47A:
FIGS. 47A and 47B are cross sectional images of skin following transdermal delivery of a protein therapeutic across the skin.
Figure 47B:

FIGS. 47A and 47B illustrate electron microscopy cross sectional views of the skin that was held in contact with the patches. The images were taken after the patches were removed (72 hours post-attachment). The sample of FIG. 47A was in contact with a patch including a nanotopography on the surface. Specifically, a DN2 pattern, as described above, was formed on the surface of the patch. The sample of FIG. 47B was held in contact with a transdermal patch that did not define a pattern of nanotopography on the surface. As can be seen, the sample of FIG. 47B shows signs of inflammation and a high density of macrophage presence.

Example 10

Transdermal patches including microneedle arrays formed as described in Example 8 were formed. Patches were formed with either a DN2 pattern or a DN3 pattern on the microneedle array as described in Table 8 of Example 9. Control patches were also formed that had no pattern formed on the film subsequently applied to the array of microneedles. Transdermal and subcutaneous formulations of etanercept (Enbrel®) were prepared according to instructions from the drug supplier.

Figure 48:
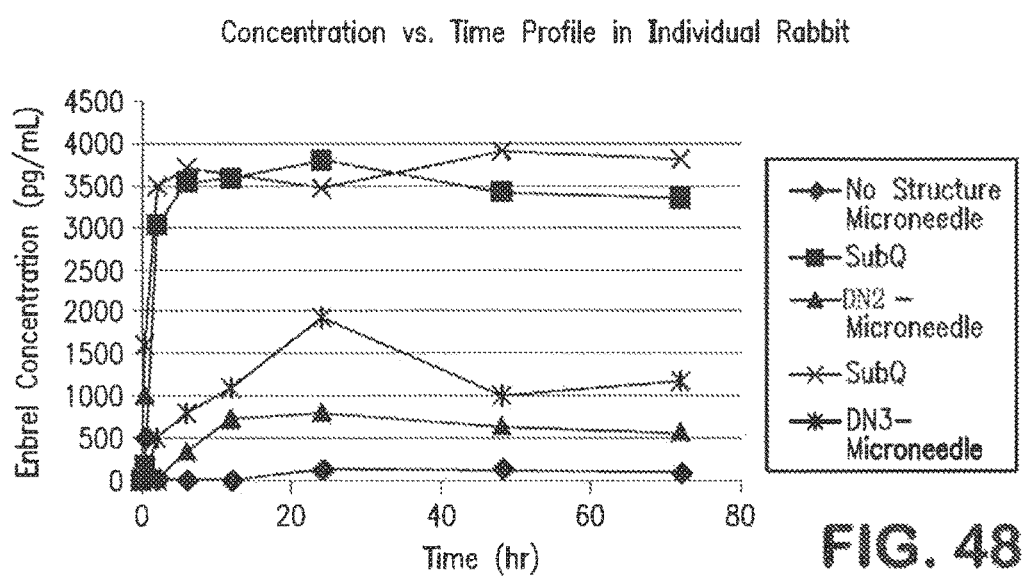
FIG. 48 graphically illustrates the blood serum concentration of a protein therapeutic delivered with a device as described herein.

Test subjects (rabbits) were transdermally dosed with Enbrel® or were subcutaneously (SubQ) dosed with Enbrel®. Results are illustrated graphically in FIG. 48, which provides the blood serum concentration in pg/ml as a function of time. The data used to develop FIG. 48 is provided below in Table 11, below.

TABLE 11

| Time | No structure microneedle | Subcutaneous | DN2 | Subcutaneous | DN3 |
| --- | --- | --- | --- | --- | --- |
| 0 | 0.00 | 0.00 | 0.00 | 0.00 | 0.00 |
| 0.5 | 0.00 | 157.49 | 0.00 | 1611.21 | 0.00 |
| 2 | 0.00 | 3029.07 | 0.00 | 3504.92 | 497.17 |
| 6 | 0.00 | 3545.14 | 338.23 | 3699.24 | 796.64 |
| 12 | 0.00 | 3577.13 | 731.22 | 3571.80 | 1080.60 |
| 24 | 116.78 | 3778.71 | 785.49 | 3464.70 | 1924.24 |
| 48 | 134.23 | 3416.73 | 638.18 | 3885.31 | 1006.95 |
| 72 | 88.68 | 3356.64 | 572.77 | 3803.42 | 1172.67 |

While the subject matter has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of the appended claims and any equivalents thereto.

What is claimed is:

1. A medical device for delivering a drug compound through a stratum corneum and to a subdermal location, the medical device comprising:
   a support having an aperture;
   an array of microneedles that extend outwardly from the support, wherein at least one microneedle contains a shaft extending from the support, the shaft including a tip configured to penetrate the stratum corneum, the shaft defining a channel extending from the support to the tip, the channel being in at least partial alignment with the aperture of the support, wherein at least some of the microneedles of the array of microneedles each have a cross-sectional dimension of from about 1 micrometer to about 1 millimeter;
   a plurality of nanostructures associated with each microneedle of the array of microneedles, at least some of the nanostructures of the plurality of nanostructures having a cross-sectional dimension less than about 500 nanometers and greater than about 5 nanometers and an aspect ratio of from about 0.2 to about 5; and
   a reservoir wherein the drug compound is retained, the reservoir being in fluid communication with the aperture of the support and the channel of the microneedle for delivery of the drug compound to the subdermal location.

2. The medical device of claim 1, wherein the at least some of the nanostructures have a cross-sectional dimension less than about 300 nanometers, and greater than about 100 nanometers.

3. The medical device of claim 1, wherein each of the plurality of nanostructures has approximately the same cross-sectional dimension as one another.

4. The medical device of claim 1 further comprising a plurality of microstructures associated with each microneedle of the array of microneedles, wherein each of the plurality of nanostructures has a cross-sectional dimension smaller than each of the plurality of microstructures.

5. The medical device of claim 4, wherein each of the plurality of microstructures has a cross-sectional dimension greater than about 500 nanometers and less than about 10 micrometers, and wherein each of the plurality of nanostructures has a cross-sectional dimension less than about 300 nanometers.

6. The medical device of claim 4, further comprising a plurality of second nanostructures, each second nanostructure of the plurality of second nanostructures having a cross-sectional dimension less than the cross-sectional dimension of each of the plurality of microstructures and greater than the cross-sectional dimension of each nanostructure of the plurality of nanostructures.

7. The medical device of claim 4, wherein the at least some of the nanostructures have a cross-sectional dimension from about 20 nanometers to about 400 nanometers, and wherein at least some of the microstructures have a cross-sectional dimension from about 600 nanometers to about 1.5 micrometers.

8. The medical device of claim 1, wherein the at least some of the nanostructures have a center-to-center spacing from about 50 nanometers to about 1 micrometer.

9. The medical device of claim 1, wherein a ratio of an average of a cross-sectional dimension of two adjacent nanostructures to a center-to-center spacing between the two adjacent nanostructures is between about 1:1 and about 1:4.

10. The medical device of claim 1, wherein each nanostructure of the plurality of nanostructures has a height from about 10 nanometers to about 1 micrometer.

11. The medical device of claim 1, wherein the at least some of the nanostructures have an aspect ratio from about 0.5 to about 3.5.

12. The medical device of claim 1 further comprising a nanopatterned film disposed on each microneedle of the array of microneedles, the nanopatterned film including the plurality of nanostructures.

13. A medical device for delivering a drug compound through a stratum corneum and to a subdermal location, the medical device comprising:
   a support having an aperture;
   an array of microneedles that extend outwardly from the support, wherein at least one microneedle contains a shaft extending from the support, the shaft including a tip configured to penetrate the stratum corneum, the shaft defining a channel extending from the support to the tip, the channel being in at least partial alignment with the aperture of the support, wherein at least some of the microneedles of the array of microneedles each have a cross-sectional dimension of from about 1 micrometer to about 1 millimeter;

a plurality of nanostructures associated with each microneedle of the array of microneedles, the plurality of nanostructures arranged in a pattern having a fractal dimension greater than about 1, wherein at least some of the nanostructures of the plurality of nanostructures have a cross-sectional dimension less than about 500 nanometers and greater than about 5 nanometers and an aspect ratio of from about 0.2 to about 5; and a reservoir wherein the drug compound is retained, the reservoir being in fluid communication with the aperture of the support and the channel of the microneedle for delivery of the drug compound to the subdermal location.

14. The medical device of claim 13, wherein the pattern has a fractal dimension from about 1.5 to about 2.5.

15. The medical device of claim 13, wherein the pattern has a fractal dimension of about 2.5.

16. The medical device of claim 13, further comprising a nanopatterned film disposed on each microneedle of the array of microneedles, the nanopatterned film including the plurality of nanostructures.

17. A medical device for delivering a drug compound through a stratum corneum and to a subdermal location, the medical device comprising:

a microneedle having an exterior surface, wherein the microneedle contains a shaft defining a channel extending therethrough;

a nanopatterned film disposed on the exterior surface of the microneedle, the nanopatterned film comprising a plurality of nanostructures, each nanostructure of the plurality of nanostructures having (i) a cross-sectional dimension less than about 500 nanometers and greater than about 5 nanometers and (ii) an aspect ratio from about 0.2 to about 5; and a reservoir wherein the drug compound is retained, the reservoir being in fluid communication with the channel of the microneedle for delivery of the drug compound to the subdermal location.

18. The medical device of claim 17, wherein the plurality of nanostructures are arranged in a pattern having a fractal dimension greater than about 1.

19. The medical device of claim 17, wherein the nanopatterned film further comprises a plurality of microstructures, wherein each of the plurality of nanostructures has a cross-sectional dimension smaller than each of the plurality of microstructures.

20. The medical device of claim 19, wherein the plurality of nanostructures defines a plurality of first nanostructures, wherein the nanopatterned film further comprises a plurality of second nanostructures, wherein each second nanostructure of the plurality of second nanostructures has a cross-sectional dimension less than the cross-sectional dimension of each microstructure of the plurality of microstructures and greater than the cross-sectional dimension of each nanostructure of the plurality of first nanostructures.

* * * * *